(12) United States Patent
Pereira et al.

(10) Patent No.: US 12,102,327 B2
(45) Date of Patent: Oct. 1, 2024

(54) SYSTEMS AND METHODS FOR TREATING ANEURYSMS

(71) Applicant: GALAXY THERAPEUTICS, INC., Milpitas, CA (US)

(72) Inventors: Edgard Luiz Ramos Pereira, Boca Raton, FL (US); Osama O. Zaidat, Lambertville, MI (US); Brett Follmer, Santa Clara, CA (US); Thomas J. Wolfe, Shorewood, WI (US); Arturo Rosqueta, San Jose, CA (US); Aamir Badruddin, Bolingbrook, IL (US); Richard Lilly, San Jose, CA (US)

(73) Assignee: Galaxy Therapeutics, Inc., Milpitas, CA (US)

( * ) Notice: Subject to any disclaimer, the term of this patent is extended or adjusted under 35 U.S.C. 154(b) by 0 days.

(21) Appl. No.: 17/614,242

(22) PCT Filed: May 25, 2020

(86) PCT No.: PCT/US2020/034450
§ 371 (c)(1),
(2) Date: Nov. 24, 2021

(87) PCT Pub. No.: WO2020/243039
PCT Pub. Date: Dec. 3, 2020

(65) Prior Publication Data

US 2022/0211383 A1 Jul. 7, 2022
US 2023/0200817 A9 Jun. 29, 2023
US 2023/0380840 A9 Nov. 30, 2023

Related U.S. Application Data

(63) Continuation-in-part of application No. 16/840,415, filed on Apr. 5, 2020, now Pat. No. 11,202,636, and
(Continued)

(51) Int. Cl.
*A61B 17/12* (2006.01)
*A61B 17/00* (2006.01)
*A61B 90/00* (2016.01)

(52) U.S. Cl.
CPC .. *A61B 17/12031* (2013.01); *A61B 17/00234* (2013.01); *A61B 17/12113* (2013.01);
(Continued)

(58) Field of Classification Search
CPC ........ A61B 17/12031; A61B 17/12113; A61B 17/12172
See application file for complete search history.

(56) References Cited

U.S. PATENT DOCUMENTS 5,250,071 A 10/1993 Palermo
5,282,806 A 2/1994 Haber et al.
(Continued)

FOREIGN PATENT DOCUMENTS

CN 102871700 B 4/2015
CN 103006285 B 6/2015
(Continued)

OTHER PUBLICATIONS

Shapiro, M., Raz, E., Becske, T., Nelson, P., "Variable Porosity of the Pipeline Embolization Device in Straight and Curved Vessels: A Guide for Optimal Deployment Strategy", Original Research Interventional, Sep. 26, 2013, 6 pages, 10.3174/ajnr.A3742, American Society of Neuroradiology, Oak Brook, USA.
(Continued)

*Primary Examiner* — Sarah A Long
*Assistant Examiner* — Raihan R Khandker
(74) *Attorney, Agent, or Firm* — BLAIR WALKER IP SERVICES, LLC

(57) ABSTRACT

An apparatus for treating an aneurysm includes an occlusion element configured to be releasably coupled to an elongate
(Continued)

delivery shaft and having a distal end, a proximal end, and a longitudinal axis extending between the distal end and the proximal end, the occlusion element configured to be delivered in a collapsed configuration and further configured to expand to an expanded configuration, the occlusion element comprising an inverted mesh tube having an outer layer and an inner layer, the outer layer transitioning to the inner layer at an inversion fold located at or adjacent the distal end of the occlusion element, the inversion fold defining an inner diameter, the occlusion element further comprising a maximum outer diameter, wherein the inner diameter is between about 35% to about 85% of the maximum outer diameter, and wherein an outer diameter of the occlusion element increases along the longitudinal axis to the maximum outer diameter.

20 Claims, 45 Drawing Sheets

Related U.S. Application Data a continuation-in-part of application No. 16/840,412, filed on Apr. 5, 2020, now Pat. No. 10,856,880, and a continuation-in-part of application No. 16/840,421, filed on Apr. 5, 2020, now Pat. No. 11,166,731, and a continuation-in-part of application No. 16/840,410, filed on Apr. 5, 2020, now Pat. No. 11,058,431.

(60) Provisional application No. 62/852,988, filed on May 25, 2019, provisional application No. 62/914,442, filed on Oct. 12, 2019, provisional application No. 62/975,741, filed on Feb. 12, 2020, provisional application No. 62/975,744, filed on Feb. 12, 2020.

(52) U.S. Cl.
CPC .. *A61B 17/12122* (2013.01); *A61B 17/12172* (2013.01); *A61B 17/12177* (2013.01); *A61B 2017/00526* (2013.01); *A61B 2017/00867* (2013.01); *A61B 2017/12059* (2013.01); *A61B 2017/12063* (2013.01); *A61B 2017/12068* (2013.01); *A61B 2090/3966* (2016.02)

(56) References Cited

U.S. PATENT DOCUMENTS

| | | |
|---|---|---|
| 5,304,195 A | 4/1994 | Twyford, Jr. et al. |
| 5,556,390 A | 9/1996 | Hicks |
| 5,795,331 A | 8/1998 | Cragg et al. |
| 5,935,148 A | 8/1999 | Villar et al. |
| 6,086,577 A | 7/2000 | Ken et al. |
| 6,093,199 A | 7/2000 | Brown et al. |
| 6,152,144 A | 11/2000 | Lesh et al. |
| 6,391,037 B1 | 5/2002 | Greenhalgh |
| 6,454,780 B1 | 9/2002 | Wallace |
| 6,506,204 B2 | 1/2003 | Mazzochi |
| 6,544,163 B2 | 4/2003 | Wallace et al. |
| 6,613,074 B1 | 9/2003 | Mitelberg et al. |
| D493,223 S | 7/2004 | Solymar |
| 6,936,055 B1 | 8/2005 | Ken et al. |
| 6,994,689 B1 | 2/2006 | Zadno-Azizi et al. |
| 7,128,736 B1 | 10/2006 | Abrams et al. |
| 7,195,636 B2 | 3/2007 | Avellanet et al. |
| 7,229,461 B2 | 6/2007 | Chin et al. |
| 7,367,985 B2 | 5/2008 | Mazzochi et al. |
| 7,410,482 B2 | 8/2008 | Murphy et al. |
| 7,569,066 B2 | 8/2009 | Gerberding et al. |
| 7,749,242 B2 | 7/2010 | Tran et al. |
| 8,142,456 B2 | 3/2012 | Rosqueta et al. |
| 8,333,796 B2 | 12/2012 | Tompkins et al. |
| 8,388,650 B2 | 3/2013 | Gerberding et al. |
| 8,398,670 B2 | 3/2013 | Amplatz et al. |
| 8,551,132 B2 | 10/2013 | Eskridge et al. |
| 8,597,320 B2 | 12/2013 | Sepetka et al. |
| 8,728,117 B1 | 5/2014 | Janardhan et al. |
| 8,777,979 B2 | 7/2014 | Shrivastava et al. |
| D713,527 S | 9/2014 | Heipl |
| 8,820,207 B2 | 9/2014 | Marchand et al. |
| 8,826,791 B2 | 9/2014 | Thompson et al. |
| 8,864,790 B2 | 10/2014 | Strauss et al. |
| 8,864,791 B2 | 10/2014 | Bloom et al. |
| 8,940,015 B2 | 1/2015 | Kariniemi |
| D727,500 S | 4/2015 | Heipl |
| D727,501 S | 4/2015 | Heipl |
| D728,102 S | 4/2015 | Heipl |
| 8,998,947 B2 | 4/2015 | Aboytes et al. |
| 9,060,777 B1 | 6/2015 | Wallace et al. |
| 9,107,670 B2 | 8/2015 | Hannes et al. |
| 9,113,890 B2 | 8/2015 | Dasnukar et al. |
| 9,179,899 B2 | 11/2015 | Freudenthal |
| 9,198,668 B2 | 12/2015 | Theobald et al. |
| 9,259,337 B2 | 2/2016 | Cox et al. |
| 9,314,326 B2 | 4/2016 | Wallace et al. |
| 9,510,811 B2 | 12/2016 | Akpinar |
| 9,585,670 B2 | 3/2017 | Hines |
| 9,597,087 B2 | 3/2017 | Marchand et al. |
| 9,636,117 B2 | 5/2017 | Bachman et al. |
| 9,669,188 B2 | 6/2017 | Echarri et al. |
| 9,855,052 B2 | 1/2018 | Aboytes et al. |
| 9,877,726 B2 | 1/2018 | Liu et al. |
| 9,918,720 B2 | 3/2018 | Marchand et al. |
| 9,980,733 B2 | 5/2018 | Badruddin et al. |
| 10,111,670 B2 | 10/2018 | Lorenzo et al. |
| 10,123,805 B2 | 11/2018 | Ayres et al. |
| 10,136,896 B2 | 11/2018 | Hewitt et al. |
| 10,149,676 B2 | 12/2018 | Mirigian et al. |
| 10,478,195 B2 | 11/2019 | Aboytes et al. |
| 10,751,065 B2 | 8/2020 | Soto del Valle et al. |
| 10,792,045 B2 | 10/2020 | Wang et al. |
| 11,026,694 B2 | 6/2021 | Wang et al. |
| 11,278,292 B2 | 3/2022 | Gorochow et al. |
| 11,413,046 B2 | 8/2022 | Xu et al. |
| 11,497,504 B2 | 11/2022 | Xu et al. |
| 11,559,309 B2 | 1/2023 | Rangwala et al. |
| 11,583,282 B2 | 2/2023 | Gorochow et al. |
| 11,596,412 B2 | 3/2023 | Xu et al. |
| 11,602,350 B2 | 3/2023 | Gorochow et al. |
| 2002/0169473 A1 | 11/2002 | Sepetka et al. |
| 2002/0188314 A1 | 12/2002 | Anderson et al. |
| 2003/0171770 A1 | 9/2003 | Kusleika et al. |
| 2003/0176884 A1 | 9/2003 | Berrada et al. |
| 2003/0195553 A1 | 10/2003 | Wallace et al. |
| 2004/0034386 A1 | 2/2004 | Fulton et al. |
| 2004/0044391 A1 | 3/2004 | Porter |
| 2004/0172056 A1 | 9/2004 | Guterman et al. |
| 2004/0199201 A1 | 10/2004 | Kellett et al. |
| 2005/0033409 A1 | 2/2005 | Burke et al. |
| 2005/0107823 A1 | 5/2005 | Leone et al. |
| 2005/0171478 A1 | 8/2005 | Selmon et al. |
| 2005/0277978 A1 | 12/2005 | Greenhalgh |
| 2006/0064151 A1 | 3/2006 | Guterman et al. |
| 2006/0106417 A1 | 5/2006 | Tessmer et al. |
| 2006/0155323 A1 | 7/2006 | Porter et al. |
| 2007/0167980 A1 | 7/2007 | Figulla et al. |
| 2007/0173928 A1 | 7/2007 | Morsi |
| 2007/0208376 A1 | 9/2007 | Meng |
| 2007/0225760 A1 | 9/2007 | Moszner et al. |
| 2007/0225794 A1 | 9/2007 | Thramann et al. |
| 2007/0270902 A1 | 11/2007 | Slazas et al. |
| 2008/0045997 A1 | 2/2008 | Balgobin et al. |
| 2008/0097495 A1 | 4/2008 | Feller, III et al. |
| 2008/0147100 A1 | 6/2008 | Wallace |
| 2008/0281350 A1 | 11/2008 | Sepetka et al. |
| 2008/0319533 A1 | 12/2008 | Lehe |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0177261 A1 | 7/2009 | Teoh et al. |
| 2009/0264978 A1 | 10/2009 | Dieck et al. |

(56) References Cited

U.S. PATENT DOCUMENTS

| | | |
|---|---|---|
| 2009/0287291 A1 | 11/2009 | Becking et al. |
| 2009/0318941 A1 | 12/2009 | Sepetka et al. |
| 2010/0179583 A1 | 7/2010 | Carpenter et al. |
| 2011/0046719 A1 | 2/2011 | Frid |
| 2011/0144669 A1 | 6/2011 | Becking et al. |
| 2011/0202085 A1 | 8/2011 | Loganathan et al. |
| 2012/0065667 A1 | 3/2012 | Javois et al. |
| 2012/0071911 A1 | 3/2012 | Sadasivan et al. |
| 2012/0143317 A1 | 6/2012 | Cam et al. |
| 2012/0245675 A1 | 9/2012 | Molaei et al. |
| 2012/0259244 A1 | 10/2012 | Roberts et al. |
| 2012/0283768 A1 | 11/2012 | Cox et al. |
| 2012/0303052 A1 | 11/2012 | Connor |
| 2012/0310270 A1 | 12/2012 | Murphy et al. |
| 2012/0330347 A1 | 12/2012 | Becking et al. |
| 2013/0066357 A1 | 3/2013 | Abotes et al. |
| 2013/0073026 A1 | 3/2013 | Russo et al. |
| 2013/0190800 A1 | 7/2013 | Murphy et al. |
| 2013/0211495 A1* | 8/2013 | Halden ............ A61B 17/12109 623/1.12 |
| 2014/0005714 A1 | 1/2014 | Quick et al. |
| 2014/0012303 A1 | 1/2014 | Heipl |
| 2014/0052233 A1 | 2/2014 | Cox et al. |
| 2014/0172001 A1 | 6/2014 | Becking et al. |
| 2014/0257360 A1 | 9/2014 | Keillor |
| 2014/0277013 A1 | 9/2014 | Sepetka et al. |
| 2014/0343602 A1 | 11/2014 | Cox et al. |
| 2015/0005811 A1 | 1/2015 | Lubock et al. |
| 2015/0133989 A1 | 5/2015 | Lubock et al. |
| 2015/0250628 A1 | 9/2015 | Monstadt et al. |
| 2015/0272589 A1 | 10/2015 | Lorenzo |
| 2015/0272590 A1* | 10/2015 | Aboytes ........... A61B 17/12168 606/200 |
| 2015/0313605 A1 | 11/2015 | Griffin |
| 2016/0022445 A1 | 1/2016 | Ruvalcava et al. |
| 2016/0030050 A1 | 2/2016 | Franano et al. |
| 2016/0120551 A1 | 5/2016 | Connor |
| 2016/0278749 A1 | 9/2016 | Javois et al. |
| 2016/0317277 A1 | 11/2016 | Carpenter et al. |
| 2017/0014114 A1 | 1/2017 | Radfiee et al. |
| 2017/0079661 A1 | 3/2017 | Bardsley et al. |
| 2017/0156734 A1 | 6/2017 | Griffin |
| 2017/0224350 A1 | 8/2017 | Shimizu et al. |
| 2017/0224355 A1* | 8/2017 | Bowman ................ B29C 71/02 |
| 2017/0348014 A1 | 12/2017 | Wallace et al. |
| 2017/0367708 A1 | 12/2017 | Mayer et al. |
| 2017/0367713 A1 | 12/2017 | Greene, Jr. et al. |
| 2018/0049731 A1 | 2/2018 | Hardy et al. |
| 2018/0242979 A1 | 8/2018 | Lorenzo |
| 2019/0008522 A1 | 1/2019 | Lorenzo |
| 2019/0053810 A1 | 2/2019 | Griffin |
| 2019/0110796 A1 | 4/2019 | Jayaraman |
| 2019/0192165 A1 | 6/2019 | Greene, Jr. et al. |
| 2019/0192167 A1 | 6/2019 | Lorenzo |
| 2019/0192168 A1 | 6/2019 | Lorenzo |
| 2019/0223876 A1 | 7/2019 | Badruddin et al. |
| 2019/0223878 A1 | 7/2019 | Lorenzo et al. |
| 2019/0223881 A1 | 7/2019 | Hewitt et al. |
| 2019/0357914 A1* | 11/2019 | Gorochow ....... A61B 17/12031 |
| 2020/0113576 A1 | 4/2020 | Gorochow et al. |
| 2020/0305885 A1 | 10/2020 | Soto Del Valle et al. |
| 2020/0367900 A1 | 11/2020 | Pedroso et al. |
| 2020/0367906 A1 | 11/2020 | Xu et al. |
| 2021/0128160 A1 | 5/2021 | Li et al. |
| 2021/0128161 A1 | 5/2021 | Nageswaran et al. |
| 2021/0128162 A1 | 5/2021 | Rhee et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0153872 A1 | 5/2021 | Nguyen et al. |
| 2021/0169499 A1 | 6/2021 | Merritt et al. |
| 2021/0275184 A1 | 9/2021 | Hewitt et al. |
| 2021/0282789 A1 | 9/2021 | Vu et al. |
| 2021/0338247 A1 | 11/2021 | Gorochow |
| 2021/0346032 A1 | 11/2021 | Patterson et al. |
| 2022/0125567 A1 | 4/2022 | Center et al. |
| 2022/0192679 A1* | 6/2022 | Zhang .............. A61B 17/12109 |
| 2022/0202425 A1 | 6/2022 | Gorochow et al. |
| 2022/0249098 A1 | 8/2022 | Milhous et al. |
| 2022/0257258 A1 | 8/2022 | Hewitt et al. |
| 2022/0304696 A2 | 9/2022 | Rhee et al. |
| 2022/0304699 A1 | 9/2022 | Gorochow |
| 2022/0378435 A1 | 12/2022 | Dholakia et al. |
| 2023/0017191 A1 | 1/2023 | Gorochow et al. |

FOREIGN PATENT DOCUMENTS

| | | |
|---|---|---|
| DE | 102012016555 A1 | 2/2014 |
| DE | 102013006503 A1 | 7/2014 |
| EP | 0832607 A1 | 4/1998 |
| EP | 3146916 A1 | 3/2017 |
| EP | 2647343 B1 | 7/2017 |
| WO | WO1999/05977 A1 | 2/1999 |
| WO | WO2002/00139 A1 | 1/2002 |
| WO | WO2005107650 A2 | 11/2005 |
| WO | WO2008156464 A1 | 12/2008 |
| WO | WO2009055782 A1 | 4/2009 |
| WO | WO2009132045 A2 | 10/2009 |
| WO | WO2012009675 A2 | 1/2012 |
| WO | WO2013138615 A2 | 9/2013 |
| WO | WO2015057796 A1 | 4/2015 |
| WO | WO2015168249 A1 | 11/2015 |
| WO | WO2017/102804 A1 | 6/2017 |
| WO | WO2017/153603 A1 | 9/2017 |
| WO | WO2017/220400 A1 | 12/2017 |
| WO | WO2018/156962 A1 | 8/2018 |
| WO | WO2019038293 A1 | 2/2019 |

OTHER PUBLICATIONS

Perez, M., Henkes, H., Bouillot, P., Brina, O., Slater, L., Pereira, V., "Intra-aneurysmal hemodynamics: evaluation of pCONus and pCANvas bifurcation aneurysm devices using DSA optical flow imaging", Journal of NeuroInterventional Surgery, Dec. 23, 2015, 6 pages, 10.1136/neurintsurg-2015-011927, Society of NeuroInterventional Surgery, Fairfax, USA.

Torii, R., Oshima, M., Kobayashi, T., Takagi, K., Tezduyar, T., "Fluid-structure interaction modeling of a patient-specific cerebral aneurysm: influence of structural modeling." Computational Mechanics 43: 151-159 (2008).

Control, etc. http://www.asianjns.org/articles/2012/7/4/images/AsianJNeurosurg_2012_7_4_159_106643_f7.jpg downloaded from internet Apr. 3, 2020.

Cerus https://neuronewsinternational-wpengine.netdna-ssl.com/wp-content/uploads/sites/3/2016/07/Cerus-Endovascular-Contour-300x194.jpg downloaded from internet Apr. 3, 2020.

Contour https://neuronewsinternational-wpengine.netdna-ssl.com/wp-content/uploads/sites/3/2017/06/Contour-e1497957260381-300x194.png downloaded from internet Apr. 3, 2020.

Medtronic https://evtoday.com/images/articles/2017-02/0217-endovascular-fig1.png downloaded from internet Apr. 3, 2020.

Bhogal, P., Udani, S., Cognard, C., Piotin, M., Brouwer, P., Sourour, N., Andersson, T., Makalanda, L., Wong, K., Fiorella, D., Arthur, A., Yeo, L., Soderman, M., Henkes, H., Pierot, L., "Endovascular flow disruption: where are we now?" Journal of Neurointerventional Surgery 11: 1024-1035 (2019).

PCT International Search Report and Written Opinion for PCT/US2020/034450, Galaxy Therapeutics, Inc., Forms PCT/ISA/220, 210, and 237 dated Aug. 1, 2020 (11 pages).

Extended European Search Report dated Nov. 11, 2022, in EP App. No. 20815001.1 filed May 25, 2020 (8 pages).

* cited by examiner

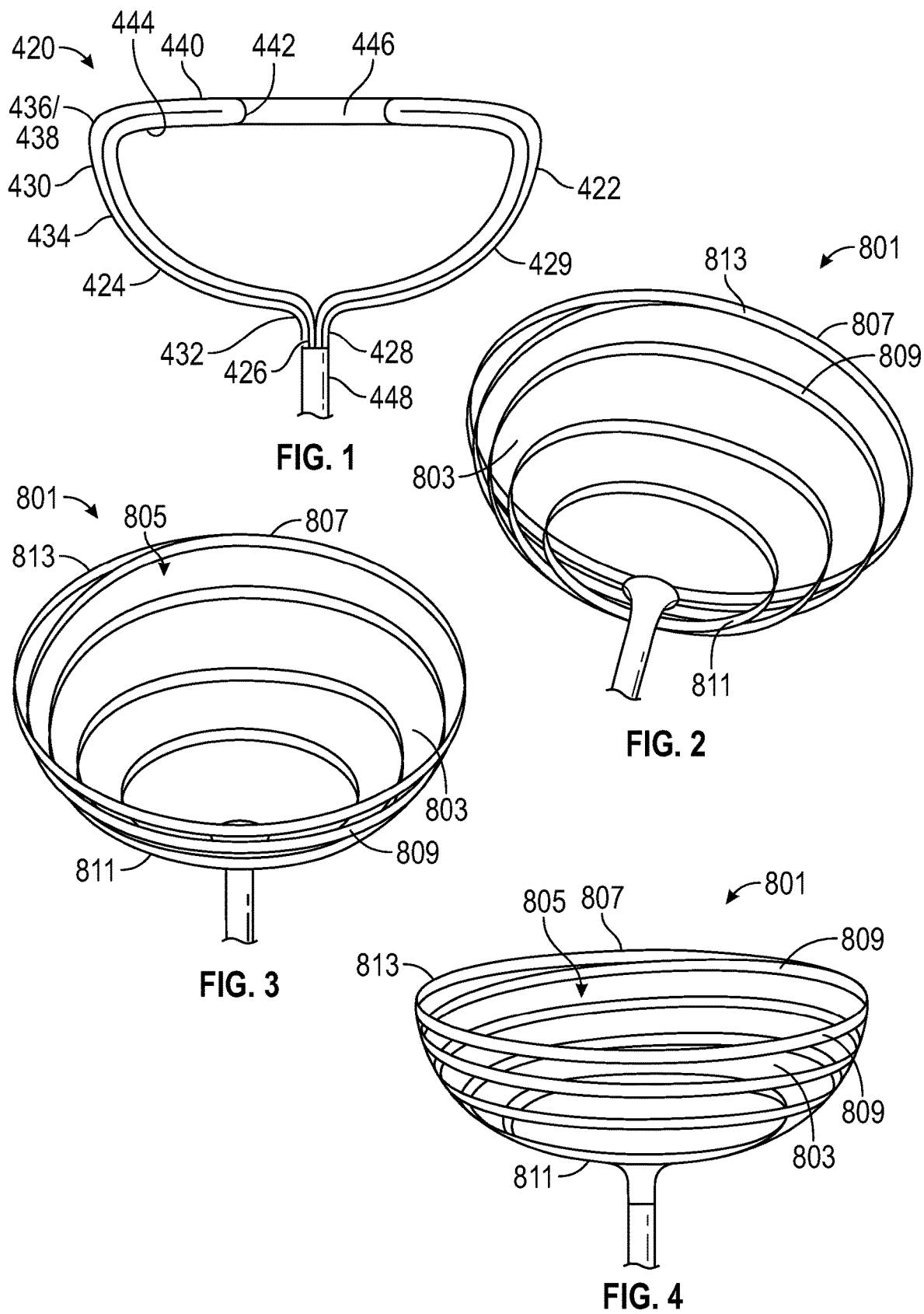

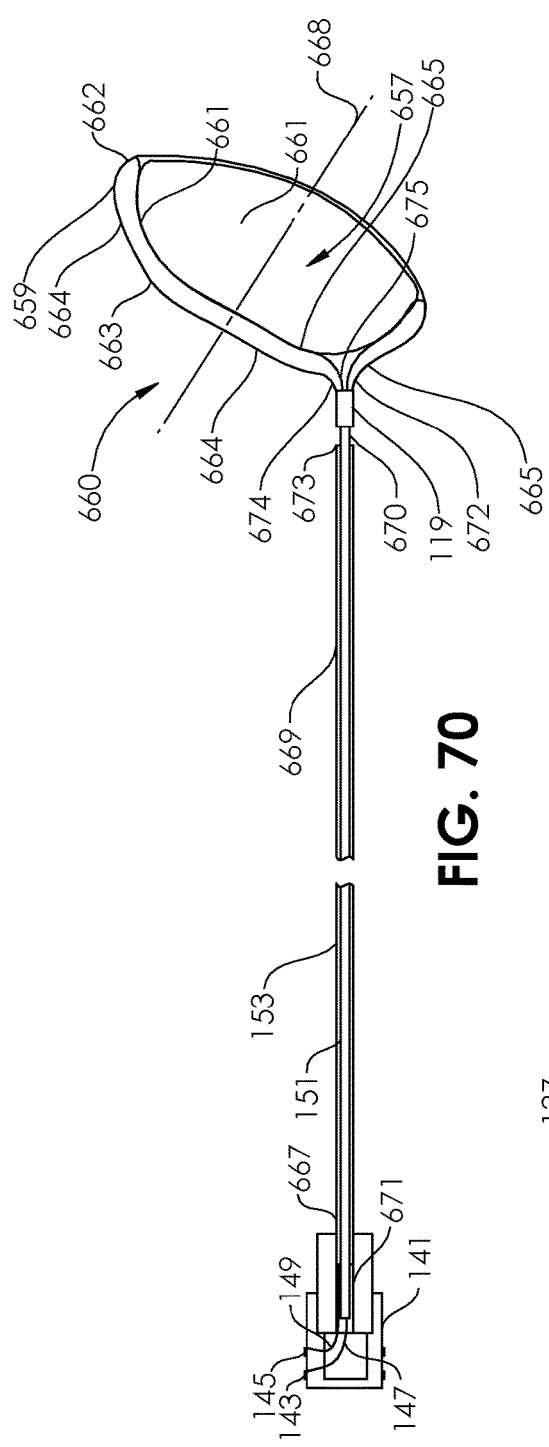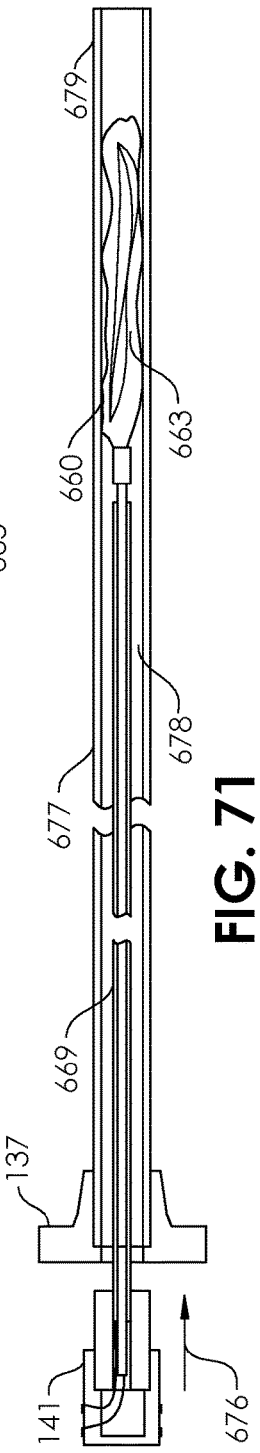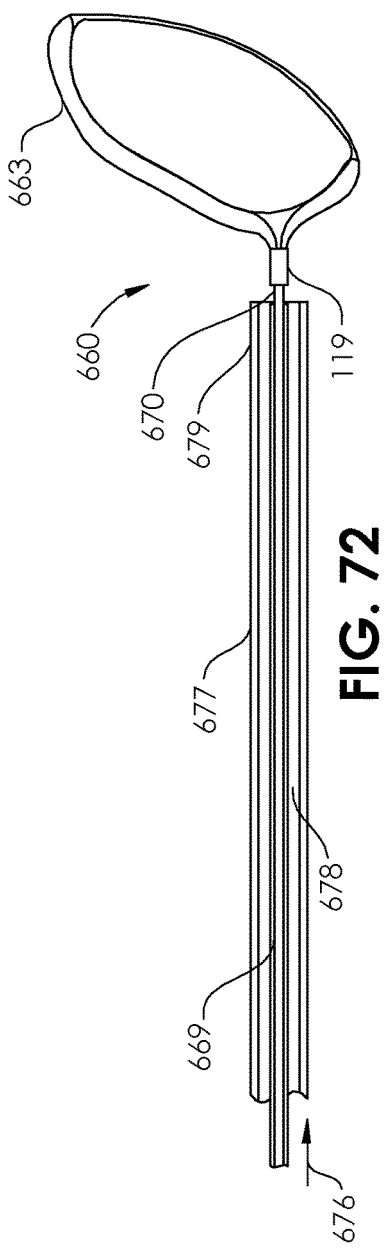

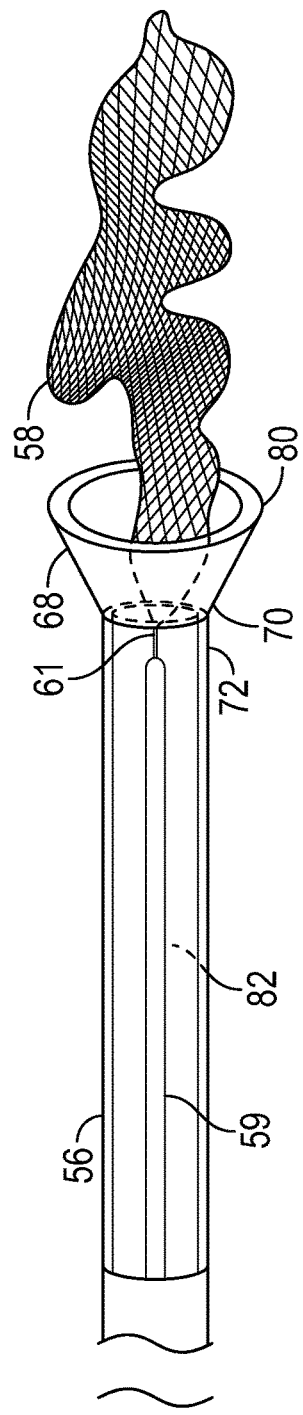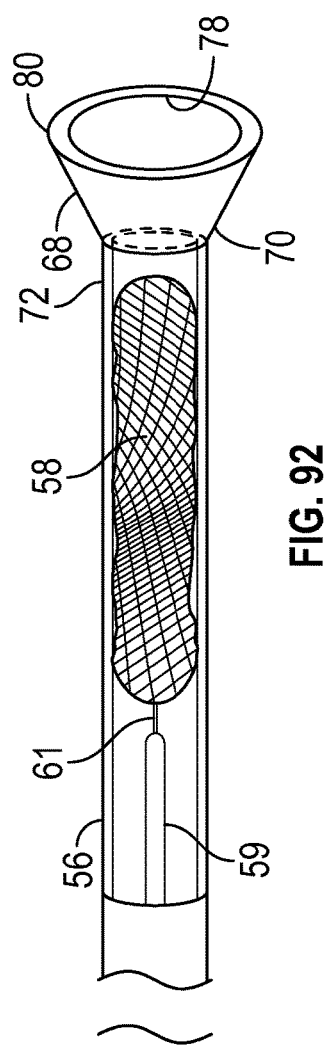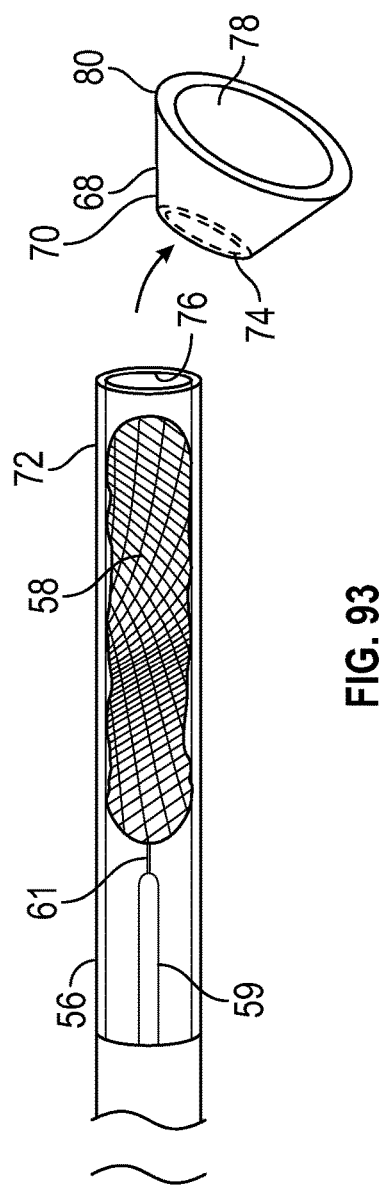

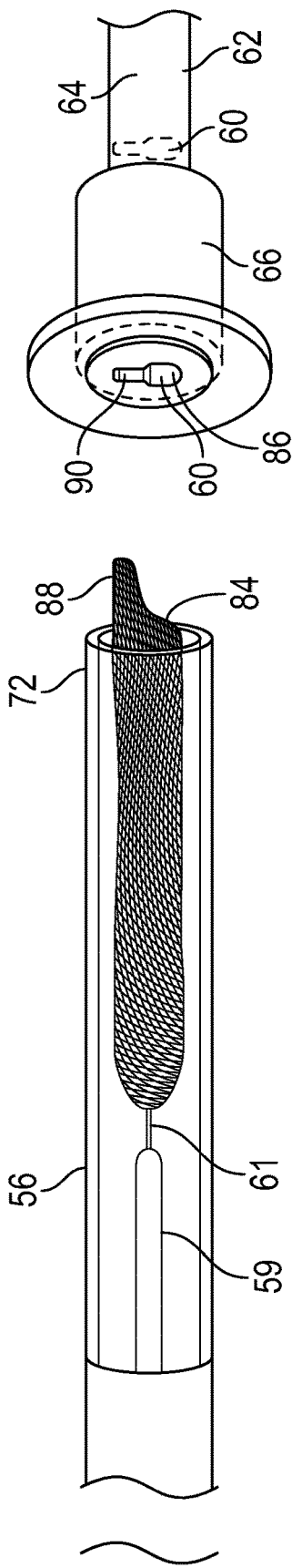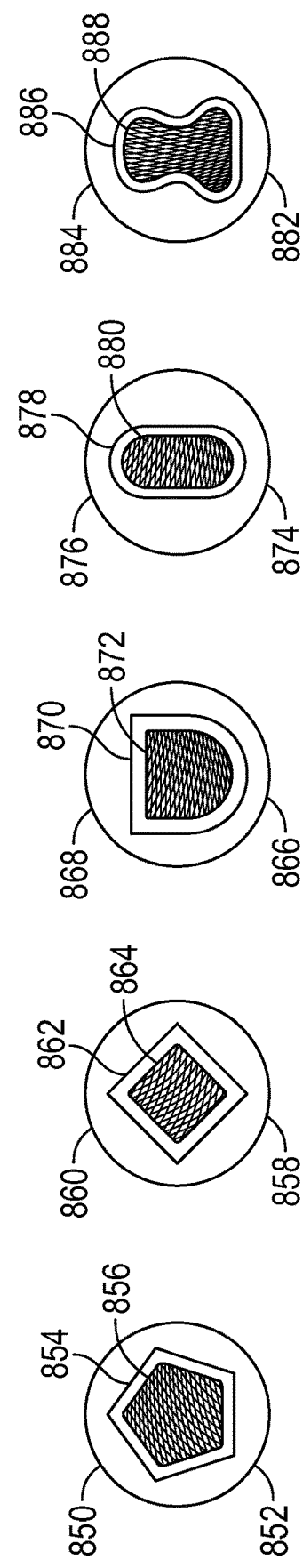
FIG. 94
FIG. 95A
FIG. 95B
FIG. 95C
FIG. 95D
FIG. 95E

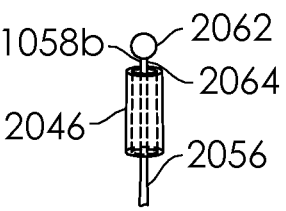
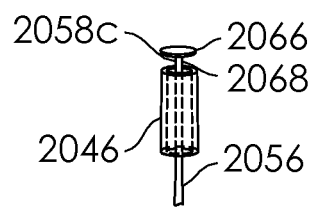
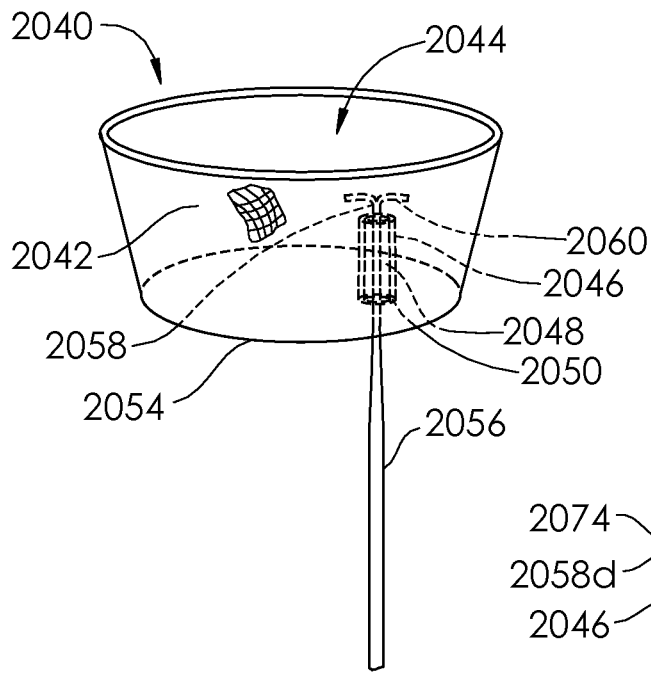
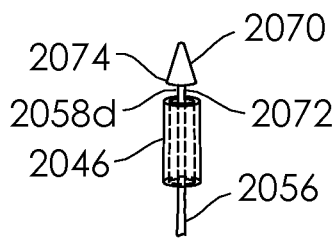
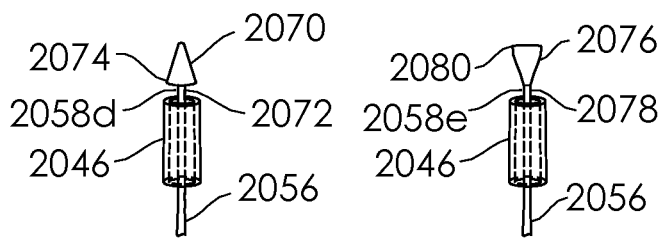
FIG. 96B
FIG. 96C
FIG. 96A
FIG. 96D
FIG. 96E
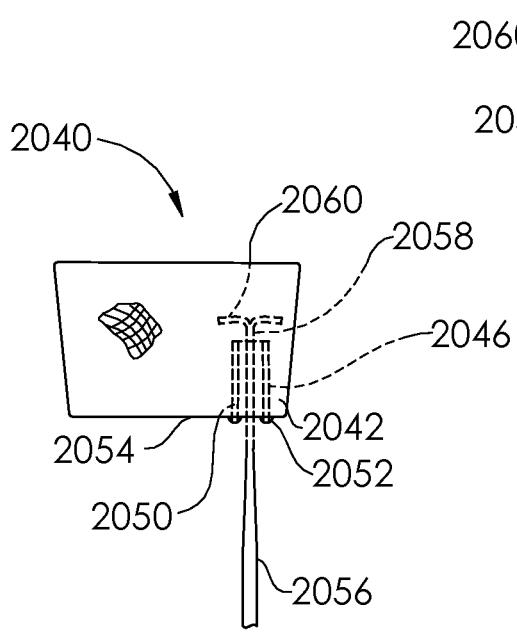
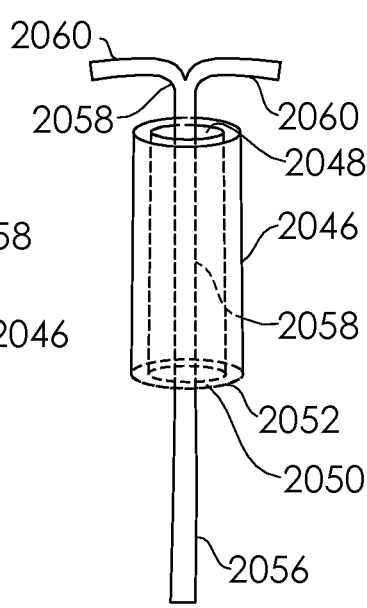
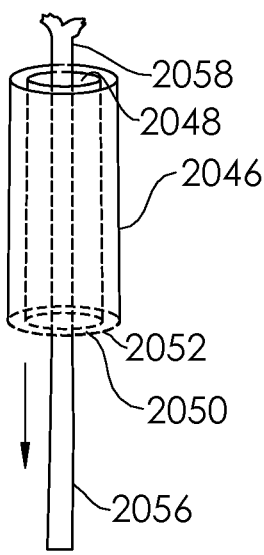
FIG. 97A
FIG. 97B
FIG. 97C

SYSTEMS AND METHODS FOR TREATING ANEURYSMS

BACKGROUND OF THE INVENTION

Field of the Invention

The field of the invention generally relates to embolic devices for filling spaces in the vascular system, including cerebral aneurysms or left atrial appendages. In some cases, the embolic devices may be used to embolize native vessels.

Description of the Related Art

An embolic device may be used as a stand-alone device to occlude and aneurysm, or may be used with an adjunctive device or material.

SUMMARY OF THE INVENTION

In one embodiment of the present disclosure, an apparatus for treating an aneurysm in a blood vessel includes an occlusion element configured to be releasably coupled to an elongate delivery shaft and having a distal end, a proximal end and a longitudinal axis extending between the distal end and the proximal end, the occlusion element including an inverted mesh tube having an outer layer and an inner layer, the outer layer transitioning to the inner layer at an inversion fold, the inversion fold defining a first inner diameter, the inner layer defining a maximum inner diameter, and the outer layer defining a maximum outer diameter, the maximum inner diameter and the maximum outer diameter both residing within a first plane transverse to the longitudinal axis, the first inner diameter residing within a second plane transverse to the longitudinal axis.

In another embodiment of the present disclosure, an apparatus for treating an aneurysm in a blood vessel includes an occlusion element configured to be releasably coupled to an elongate delivery shaft and having a distal end, a proximal end, and a longitudinal axis extending between the distal end and the proximal end, a occlusion element configured to be delivered in a collapsed configuration through an inner lumen of a delivery catheter, the inner lumen having a proximal end and a distal end, the occlusion element further configured to expand to an expanded configuration when advanced out of the distal end of the inner lumen of the delivery catheter and into the aneurysm, the occlusion element including an inverted mesh tube having an outer layer and an inner layer, the outer layer transitioning to the inner layer at an inversion fold located at or adjacent the distal end of the occlusion element, the inversion fold defining an inner diameter, the occlusion element further including a maximum outer diameter, wherein the inner diameter is between about 35% to about 85% of the maximum outer diameter, and wherein an outer diameter of the occlusion element increases along the longitudinal axis to the maximum outer diameter.

In another embodiment of the present disclosure, an apparatus for treating an aneurysm in a blood vessel includes an occlusion element configured to be releasably coupled to an elongate delivery shaft, the occlusion element including a cover having a mesh material and configured to be delivered in a collapsed configuration through an inner lumen of a delivery catheter, the inner lumen having a proximal end and a distal end, the cover further configured to expand to an expanded configuration when advanced out of the distal end of the inner lumen of the delivery catheter and into the aneurysm, wherein the cover includes a diameter that is greater than the diameter or maximum transverse dimension of a neck portion of the aneurysm, and wherein the cover includes a distal concavity configured to face away from the neck portion of the aneurysm, and a first tubular mesh having a first end, a second end, a wall and a lumen, the first end and the second end of the first tubular mesh coupled to a central portion of the cover such that an intermediate portion of the first tubular mesh between the first end and the second end includes a substantially 180 degree turn, the intermediate portion of the first tubular mesh extending from the distal concavity of the cover, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm.

In another embodiment of the present disclosure, an apparatus for treating an aneurysm in a blood vessel includes an occlusion element configured to be releasably coupled to an elongate delivery shaft, the occlusion element including a cover having a mesh material and configured to be delivered in a collapsed configuration through an inner lumen of a delivery catheter, the inner lumen having a proximal end and a distal end, the cover further configured to expand to an expanded configuration when advanced out of the distal end of the inner lumen of the delivery catheter and into the aneurysm, wherein the cover includes a diameter that is greater than the diameter or maximum transverse dimension of a neck portion of the aneurysm, a first tubular mesh having a first end, a second end, a wall and a lumen, the first end and the second end of the first tubular mesh coupled to a central portion of the cover such that an intermediate portion of the first tubular mesh between the first end and the second end includes a substantially 180 degree turn, the intermediate portion of the first tubular mesh extending from the distal concavity of the cover, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm, and a second tubular mesh having a first end, a second end, a wall and a lumen, the first end and the second end of the second tubular mesh coupled to a central portion of the cover such that an intermediate portion of the second tubular mesh between the first end and the second end includes a substantially 180 degree turn, the intermediate portion of the second tubular mesh extending from the distal concavity of the cover, wherein the intermediate portion of the second tubular mesh has a collapsed configuration configured to be delivered through the inner lumen of the delivery catheter, and wherein the intermediate portion of the second tubular mesh is configured to expand to an expanded configuration when advanced out of the distal end of the inner lumen of the delivery catheter an into the aneurysm.

In yet another embodiment of the present disclosure, an apparatus for treating an aneurysm in a blood vessel includes an occlusion element configured to be releasably coupled to an elongate delivery shaft, the occlusion element including a cover having a mesh material and configured to be delivered in a collapsed configuration through an inner lumen of a delivery catheter, the inner lumen having a proximal end and a distal end, the cover further configured to expand to an expanded configuration when advanced out of the distal end of the inner lumen of the delivery catheter and into the aneurysm, wherein the cover in its expanded configuration has a transverse dimension that is greater than a maximum transverse dimension of a neck portion of the aneurysm, and a first tubular mesh having a first end, a second end, a wall and a lumen, the first end and the second end of the first tubular mesh coupled to a central portion of the cover such that an intermediate portion of the first tubular mesh between the first end and the second end includes a substantially 180 degree turn, the intermediate portion of the first tubular mesh extending distally from the central portion of the cover, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm.

In still another embodiment of the present disclosure, an apparatus for treating an aneurysm in a blood vessel includes an occlusion element configured to be releasably coupled to an elongate delivery shaft, the occlusion element including a first tubular mesh having a first end, a second end, a wall and a lumen, the first end and the second end of the first tubular mesh coupled together at a proximal end of the occlusion element such that an intermediate portion of the first tubular mesh between the first end and the second end includes a substantially 180 degree turn, the intermediate portion of the first tubular mesh extending distally from the proximal end of the occlusion element, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm. In some embodiments, the apparatus further includes a second tubular mesh having a first end, a second end, a wall and a lumen, the first end and the second end of the second tubular mesh coupled to the proximal end of the occlusion element such that an intermediate portion of the second tubular mesh between the first end and the second end includes a substantially 180 degree turn, the intermediate portion of the second tubular mesh extending distally from the proximal end of the occlusion element, wherein the intermediate portion of the second tubular mesh has a collapsed configuration configured to be delivered through the inner lumen of the delivery catheter, and wherein the intermediate portion of the second tubular mesh is configured to expand to an expanded configuration when advanced out of the distal end of the inner lumen of the delivery catheter an into the aneurysm.

In another embodiment of the present disclosure, an apparatus for treating an aneurysm in a blood vessel includes an occlusion element configured to be releasably coupled to an elongate delivery shaft, the occlusion element including a mesh body configured to be delivered in a collapsed configuration through an inner lumen of a delivery catheter, the inner lumen having a proximal end and a distal end, the body further configured to expand to an expanded configuration when advanced out of the distal end of the inner lumen of the delivery catheter and into the aneurysm, wherein the body includes a proximal portion having a proximal maximum transverse dimension A and a distal maximum transverse dimension B and a frustoconical portion extending between the proximal maximum transverse dimension A and the distal maximum transverse dimension B, and wherein the body further includes distal portion having a maximum transverse dimension C and a waist portion between the proximal portion and the distal portion, and wherein the dimension A is between about 50% and about 100% of dimension B.

In another embodiment of the present disclosure, an apparatus for treating an aneurysm in a blood vessel includes an occlusion element configured to be releasably coupled to an elongate delivery shaft, the occlusion element including an inverted mesh tube having an outer layer and an inner layer, the outer layer transitioning to the inner layer at an inversion fold, wherein at least the outer layer is formed into an expanded shape having a proximal section having a first diameter, a distal section having a second diameter, and a waist portion having a third diameter, wherein the third diameter is less than the first diameter and the third diameter is less than the second diameter.

In yet another embodiment of the present disclosure, an apparatus for treating an aneurysm in a blood vessel includes an occlusion element configured to be releasably coupled to an elongate delivery shaft, the occlusion element including an inverted mesh tube having an outer layer and an inner layer, the outer layer transitioning to the inner layer at an inversion fold, wherein at least the outer layer is formed into an expanded shape having a proximal section having a first diameter, a distal section having a second diameter, and a first waist portion having a third diameter, a middle section having a fourth diameter, and a second waist portion having a fifth diameter, wherein the first diameter, the second diameter, and the fourth diameter are each greater than the third diameter, and wherein the first diameter, the second diameter, and the fourth diameter are each greater than the fifth diameter.

In still another embodiment of the present disclosure, a method for forming an apparatus for treating an aneurysm in a blood vessel includes forming a mesh tube, inverting the mesh tube to form an outer layer and an inner layer, the outer layer transitioning to the inner layer at an inversion fold, forming at least the outer layer into an expanded shape having a proximal section having a first diameter and a distal section having a second diameter, and etching the distal section to decrease its stiffness.

In yet another embodiment of the present disclosure, an apparatus for treating an aneurysm in a blood vessel includes an occlusion element configured to be releasably coupled to an elongate delivery shaft, the occlusion element including an inverted mesh tube having an outer layer and an inner layer, the outer layer transitioning to the inner layer at an inversion fold, the occlusion element configured to be delivered in a collapsed configuration through an inner lumen of a delivery catheter, the inner lumen having a proximal end and a distal end, the occlusion element further configured to expand to an expanded configuration when advanced out of the distal end of the inner lumen of the delivery catheter and into the aneurysm, wherein in the expanded configuration, at least the outer layer of the inverted mesh tube is formed into an expanded shape including a proximal section having a first transverse dimension, a distal section having a second transverse dimension, and a waist portion having a third transverse dimension, wherein the third transverse dimension is less than the first transverse dimension, and the third transverse dimension is less than the second transverse dimension, and wherein in the expanded configuration, the waist portion is configured to be deformed by an externally applied force such that a distance between the distal section and the proximal section is decreased.

In another embodiment of the present disclosure, a vaso-occlusive system configured for embolizing an aneurysm, the aneurysm having a neck and a sac, the system including an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal face configured to seat against a lower wall portion of the sac of the aneurysm against the neck of the aneurysm and a concavity, opposite the proximal face, and having a perimeter extending into the sac and away from the neck of the aneurysm, the concavity arranged around a longitudinal axis, and wherein the vaso-occlusive device is configured to be releasably coupled to the distal end of the pusher at a releasable joint, the distal end of the pusher extending from the releasable joint at an angle formed with the central longitudinal axis of between about 30 degrees and about 120 degrees.

In another embodiment of the present disclosure, a vaso-occlusive system configured for embolizing an aneurysm, the aneurysm having a neck and a sac, the system including an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal face configured to seat against a lower wall portion of the sac of the aneurysm against the neck of the aneurysm and a concavity, opposite the proximal face, and having a perimeter extending into the sac and away from the neck of the aneurysm, the concavity arranged around a longitudinal axis, and wherein the vaso-occlusive device is configured to be releasably coupled to the distal end of the pusher at a releasable joint, and wherein the releasable joint is coupled at a location on the proximal face of the vaso-occlusive device that is radially offset from the central longitudinal axis.

In yet another embodiment of the present disclosure, a vaso-occlusive system configured for embolizing an aneurysm, the aneurysm having a neck and a sac, the system including an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal face configured to seat against a lower wall portion of the sac of the aneurysm against the neck of the aneurysm and a concavity, opposite the proximal face, and having a perimeter extending into the sac and away from the neck of the aneurysm, the concavity arranged around a longitudinal axis, and wherein the vaso-occlusive device is configured to be releasably coupled to the distal end of the pusher at a releasable joint, and wherein the releasable joint has a characteristic chosen from the list consisting of: (1) the distal end of the pusher extends from the releasable joint at an angle formed with the central longitudinal axis of between about 30 degrees and about 120 degrees, and (2) the releasable joint is coupled at a location on the proximal face of the vaso-occlusive device that is radially offset from the central longitudinal axis.

In still another embodiment of the present disclosure, a system for embolizing an aneurysm includes an expandable implant configured for placement within an aneurysm, the implant having a collapsed configuration and an expanded configuration, the expanded configuration having an asymmetric shape in relation to a longitudinal axis, and a delivery catheter having a proximal end and a distal end and a lumen extending from the proximal end to the distal end, the lumen having a non-circular cross-section at least at a distal region adjacent the distal end of the delivery catheter, wherein expandable implant in its collapsed configuration is configured to fit into the lumen in the distal region in a keyed manner, such that the expandable implant is deliverable from the lumen at the distal end of the delivery catheter in a particular rotational position in relation to the longitudinal axis.

In yet another embodiment of the present disclosure, a method for inserting an expandable implant includes providing an introducer having a proximal end and a distal end and an introducer lumen extending between the proximal end of the introducer and the distal end of the introducer, the introducer lumen configured to hold an expandable implant in its collapsed configuration while the expandable implant is introduced into the lumen of the delivery catheter at its proximal end, wherein the lumen of the delivery catheter has a non-circular shape, and wherein the expandable implant in its collapsed configuration has a substantially non-circular shape, pushing the expandable implant out of the introducer lumen and into the lumen of the delivery catheter such that the substantially non-circular shape of the expandable implant in its collapsed configuration is oriented in a keyed manner with the non-circular shape of the lumen of the delivery catheter, and advancing the expandable implant such that it is entirely within the lumen of the delivery catheter.

In still another embodiment of the present disclosure, a vaso-occlusive system configured for embolizing an aneurysm, the aneurysm having a neck and a sac, the system includes an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal end configured to seat against the aneurysm adjacent the neck of the aneurysm, a distal end configured to extend in the sac and away from the neck of the aneurysm, and a central longitudinal axis, and wherein the vaso-occlusive device is configured to be releasably coupled to the distal end of the pusher at a releasable joint, wherein the releasable joint includes either one or both of the configurations in the list consisting of: (1) the distal end of the pusher extends from the releasable joint at an angle formed with the central longitudinal axis of between about 30 degrees and about 120 degrees, and (2) the releasable joint is coupled at a location on the proximal end of the vaso-occlusive device that is radially offset from the central longitudinal axis.

BRIEF DESCRIPTION OF THE DRAWINGS

FIG. 1 is a sectional view of an occlusion device according to an embodiment of the present disclosure.

FIG. 2 is a perspective view of an occlusion device according to an embodiment of the present disclosure.

FIG. 3 is a perspective view of the occlusion device of FIG. 2.

FIG. 4 is a perspective view of the occlusion device of FIG. 2.

FIG. 70 is a sectional view of the occlusion device according to an embodiment of the present disclosure.

FIG. 71 is a sectional view of the occlusion device of FIG. 70 being delivered within a microcatheter.

FIG. 72 is a sectional view of the occlusion device of FIG. 70 being deployed from a microcatheter.

FIG. 91 is a perspective view of a loading sheath according to an embodiment of the present disclosure.

FIG. 92 is a perspective view of the loading sheath of FIG. 91 with an occlusion device restrained in its collapsed configuration.

FIG. 93 is a perspective view of the loading sheath of FIG. 91 being changed to another configuration.

FIG. 94 is a perspective of the loading sheath of FIG. 91 being used to load an occlusion device into a proximal end of a delivery catheter.

FIGS. 95A-95E are alternate configurations of the lumen of a delivery catheter, according to embodiments of the present disclosure.

FIG. 96A is a perspective view of an occlusion device according to an embodiment of the present disclosure.

FIG. 96B is a detail view of an alternative distal end of the occlusion device of FIG. 96A, according to an embodiment of the present disclosure.

FIG. 96C is a detail view of an alternative distal end of the occlusion device of FIG. 96A, according to an embodiment of the present disclosure.

FIG. 96D is a detail view of an alternative distal end of the occlusion device of FIG. 96A, according to an embodiment of the present disclosure.

FIG. 96E is a detail view of an alternative distal end of the occlusion device of FIG. 96A, according to an embodiment of the present disclosure.

FIG. 97A is a side view of the occlusion device of FIG. 96A.

FIG. 97B is a detail view of the detachment portion of the occlusion device of FIG. 96A, prior to detachment.

FIG. 97C is a detail view of the detachment portion of the occlusion device of FIG. 96A, during detachment.

DETAILED DESCRIPTION OF THE ILLUSTRATED EMBODIMENTS

Figure 5:
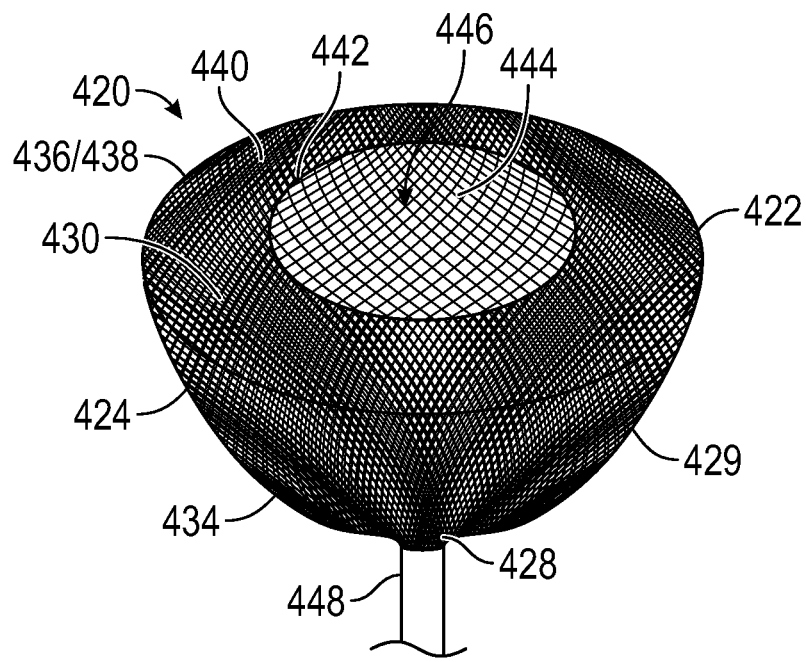
FIG. 5 is a perspective view of the occlusion device of FIG. 1.

Aneurysms are abnormal bulging or weakening of a blood vessel, often an artery, and can have many complications. A bulging of the blood vessel can disrupt or put pressure on surrounding tissues. Cerebral aneurysms can result in a variety of side effects, such as impaired vision, impaired speech, impaired balance, etc. Further, the aneurysm creates a volume that is not along the main flow path of the blood through the blood vessel. It therefore can serve as a location for blood to become stagnant and, due to swirling eddy currents, can contribute to the formation of a thromboembolism. If an aneurysm ruptures, it can cause severe internal bleeding, which in cerebral arteries can often become fatal.

Aneurysms can be treated externally with open surgery. Such procedures typically involve closing off the entrance or "neck" of the aneurysm with a device such as vascular clip, clamp or a ligature. However, such open surgical procedures can be highly invasive and may lead to trauma to the adjacent tissue and other side effects.

Aneurysms can also be treated through endovascular procedures. In one procedure, detachable lengths of wires (e.g., coils) are inserted into the interior volume of the aneurysm using a catheter. The coils are intended to fill the volume of the aneurysm to decrease the flow of blood into the aneurysm, inducing stagnation of flow and stimulate clotting within the aneurysm. In settings of large cerebral aneurysms, filling of the aneurysm with multiple coils can lead to mass effect that may induce brain swelling and be an independent cause for new symptoms. In another procedure, for aneurysms with a relatively large neck, the adjunctive use of stents assists with the retention of the coils within the aneurysm. This approach may have a contraindication to being used when treating ruptured aneurysm, due to the need for additional anti-thrombotic medications. In another procedure, the coils are held in the volume of the aneurysm with a temporary balloon that is inflated in the blood vessel. The balloon is deflated and removed once the mass of coils is secured. In still another procedure, a stent device is placed in the artery to promote flow of blood past the aneurysm. This leads to stagnation of the blood within the aneurysm and thrombosis inside the aneurysm volume. However, a side branch of a main artery in which the stent device is placed may become trapped or "jailed," which can impede access to the side branch. In other instances, the side branch can become clotted off, possibly causing a stroke. Additionally, such a procedure generally requires the use additional anti-thrombotic medications, which limits the use of such devices in the setting of treatment of ruptured aneurysms. The stent device is often formed with a relatively tight weave. While the tight weave increases the effectiveness of the stent device in diverting the blood flow, it also impedes or prevents access to the volume of the aneurysm or the jailed artery. In the event that the aneurysm fails to clot, the obstruction of the aneurysm by the stent device prevents the possibility of placing embolic devices inside the aneurysm. Additional procedures such as the placement of additional stents or open surgery may then be required to treat the residual.

Procedures that involve packing the volume of the aneurysm can suffer from several common shortcomings. First, it can take many coils of wire to fill the volume of the aneurysm, which is time consuming and increases the time it takes to complete the procedure. Further, the coils may be compacted over time to occupy a smaller percentage of the total volume of the aneurysm. A great enough compaction of the coils can be considered a recurrence of the aneurysm and may require further treatment.

FIGS. 1 and 5 illustrate an occlusion device 420 having a dual layer mesh, and comprising a single D-shaped element 422 having a D-shaped longitudinal section. the occlusion device 420 is constructed from an inverted mesh tube 424 having a first end 426, a second end 428, and a wall 429. The inverted mesh tube 424 extends on an outer layer 430 from the second end 428 past a proximal end 432 of the D-shaped element 422 and along a hemisphere shape 434 to a maximum outer diameter portion 436 having an acute angulation 438. From the maximum outer diameter portion 436, the outer layer 430 extends radially inward along a substantially flattened portion 440 substantially overlaying a transverse plane, to an inversion fold 442 from the outer layer 430 to an inner layer 444 which follows the contours of the outer layer 430 from a distal orifice 446 to the first end 426. The occlusion device 420 is fabricated as an inverted mesh tube 424 having a simple straight elongate configuration, and is subsequently formed into the shape shown in FIGS. 1 and 5, and heat set into this shape. For example, the inverted mesh tube 424 may be constructed as a single layer mesh tube formed of at least some nickel-titanium alloy filaments, and then inverted on itself. The inverted mesh tube 424 may then be placed into a die or mold comprising one or more pieces, to hold it in the shape of the D-shaped element 422. Then, the D-shaped element 422 may be subjected to an elevated temperature and then cooled, to lock in the shape, resulting in a D-shaped element 422 having at least some superelastic properties. The occlusion device 420, like all of the occlusion devices described herein, is configured to be delivered in a compressed configuration through the lumen of a delivery catheter and out of the distal end of the lumen into an aneurysm. When the occlusion device 420 is released from the constraints of the lumen, it self-expands to an expanded configuration within the aneurysm. A marker band 448 holds the first end 426 and the second end 428 together, and can comprise a radiopaque material such as platinum or a platinum alloy such as 90% platinum and 10% iridium, or 80% platinum and 20% iridium, or 75% platinum and 25% iridium. The D-shaped element 422 is configured to cover a neck portion of an aneurysm. The maximum outer diameter portion 436 can be configured to engage a wall portion of the aneurysm to maintain the occlusion device 420 in place. For example, the diameter of the maximum outer diameter portion 436 can be oversized in relation to the target aneurysm diameter, e.g., 10% greater, 20% greater, etc. In some embodiments, the occlusion device 420 in its expanded configuration has a general cross-sectional isosceles trapezoidal shape in a plane containing the longitudinal axis. In some embodiments, the occlusion device 420 in its expanded configuration has a general cross-sectional triangular shape in a plane containing the longitudinal axis.

The distal orifice 446 can be sized to control the overall width of the substantially flattened portion 440. The smaller the distal orifice 446, the thicker the width (on each side of the orifice 446) in the substantially flattened portion 440. The thicker the width of this portion, the more radial force (aneurysm gripping force) can be placed on the aneurysm wall by the maximum outer diameter portion 436. In some embodiments, the inner diameter of the orifice 446 is between about 35% to about 85% the diameter of the maximum outer diameter portion 436. In some embodiments, the inner diameter of the orifice 446 is between about 45% to about 75% the diameter of the maximum outer diameter portion 436. In some embodiments, the inner diameter of the orifice 446 is between about 50% to about 70% the diameter of the maximum outer diameter portion 436. In some embodiments, the inner diameter of the orifice 446 is between about 55% to about 65% the diameter of the maximum outer diameter portion 436. In some embodiments, the orifice 446 is on the same plane as the maximum outer diameter portion 436. In other embodiments, the orifice 446 is on a plane that is distal to a plane generally carrying the maximum outer diameter portion 436. In other embodiments, the orifice 446 is on a plane that is proximal to a plane generally carrying the maximum outer diameter portion 436.

Figure 6:
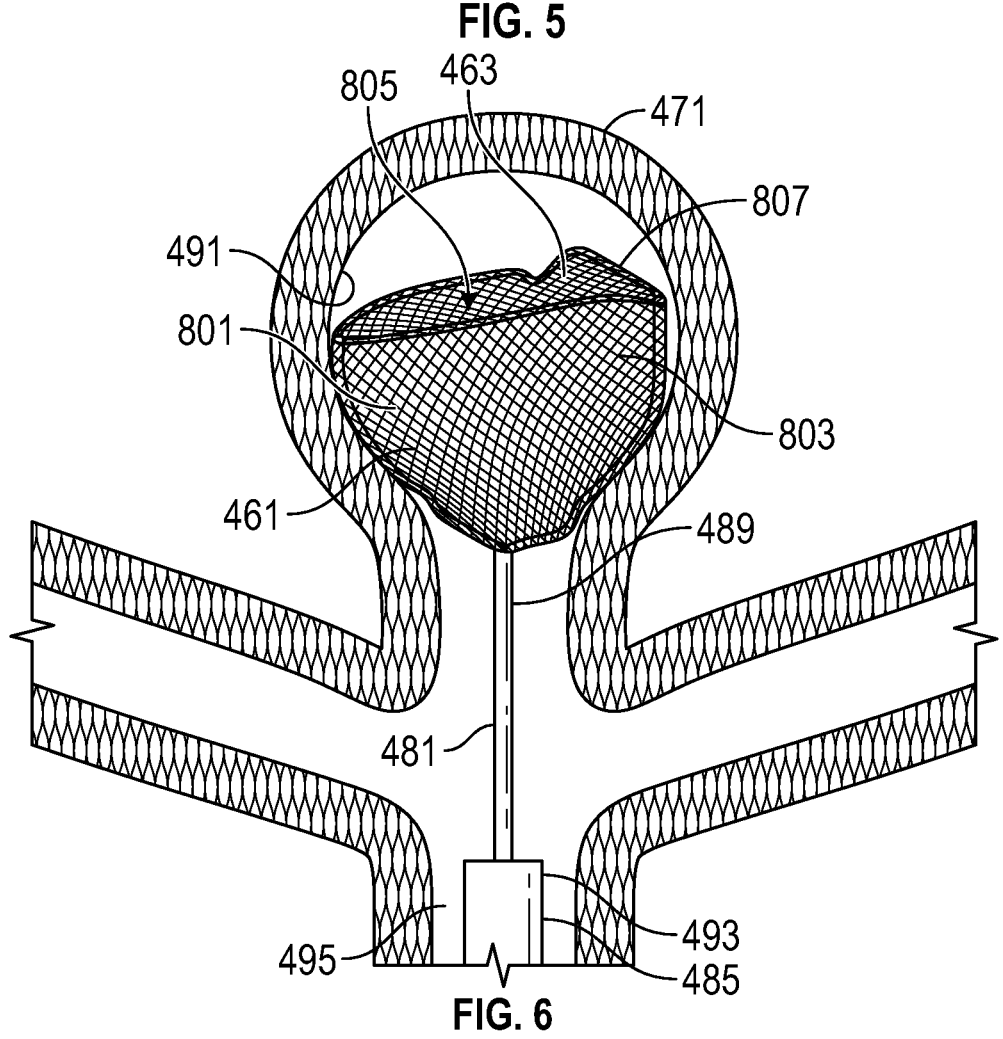
FIG. 6 is a partial sectional view of the occlusion device of FIG. 2 delivered into a terminal aneurysm.

FIGS. 2-4 illustrate a bowl-shaped occlusion device 801 constructed from an inverted mesh tube 803 and having a concavity 805 at its distal end 807. A laser-cut tapering coil 809 may be constructed from nickel-titanium sheet material or nickel titanium tubing. The inverted mesh tube 803 is not shown in FIGS. 2-4 in order to show the detail of the coil 809. The inverted mesh tube 803 is shown covering the coil 809 in FIG. 6, with the occlusion device 801 deployed in a terminal aneurysm 471. In some embodiments, the coil 809 is between an outer layer 461 and an inner layer 463 of the inverted mesh tube 803, and applies an outward radial force on the outer layer 461 and thereby on the aneurysm 471. In other embodiments, the coil 809 is within both the outer layer 461 and the inner layer 463 of the inverted mesh tube 803 and applies an outward radial force on the inner layer 463 and outer layer 461 together, and on thereby on the aneurysm 471. The coil 809 has a small diameter end 811 and a large diameter end 813, tapering or varying in diameter between the two ends 811, 813, thus to match the bowl-shape of the occlusion device 801. In some embodiments, the coil 809 at least partially forces the bowl shape into the outer layer 461, or into the inner layer 463 and outer layer 461. In some embodiments, the coil 809 may even be outside of both the inner layer 463 and the outer layer 461, and may be coupled to one or both of the inner layer 463 or outer layer 461 by adhesive bonding, epoxy bonding, hot melt, tying, sewing, weaving, welding, soldering, stapling, brazing, or other manners. Thus, the outward radial force applied by the coil 809 pulls the outer layer 461 and or the inner layer 463 outwardly. The maximum diameter of the occlusion device 801 (e.g., at the large diameter end 813) can be configured to engage a wall portion 491 of the aneurysm 471 to maintain the occlusion device 801 in place. For example, the maximum diameter can be oversized in relation to the target aneurysm diameter, e.g., 10% greater, 20% greater, etc. In some embodiments, the occlusion device 801 in its expanded configuration has a general cross-sectional isosceles trapezoidal shape in a plane containing the longitudinal axis. In some embodiments, the occlusion device 801 in its expanded configuration has a general cross-sectional triangular shape in a plane containing the longitudinal axis.

The occlusion device 801 is coupled to a pusher wire 481 and is delivered through a microcatheter 485 that is placed through the main artery 495. After being deployed in the desired position, the occlusion device 801 is released from the pusher wire 481 by detachment at a detachable joint 489. A detachable joint 489 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. During delivery, the pusher wire 481 is held on its proximal end (not shown) by a user and pushed in a forward longitudinal direction, in order to advance the occlusion device 801 to the distal end 493 of the delivery catheter (microcatheter) 485.

Figure 7:
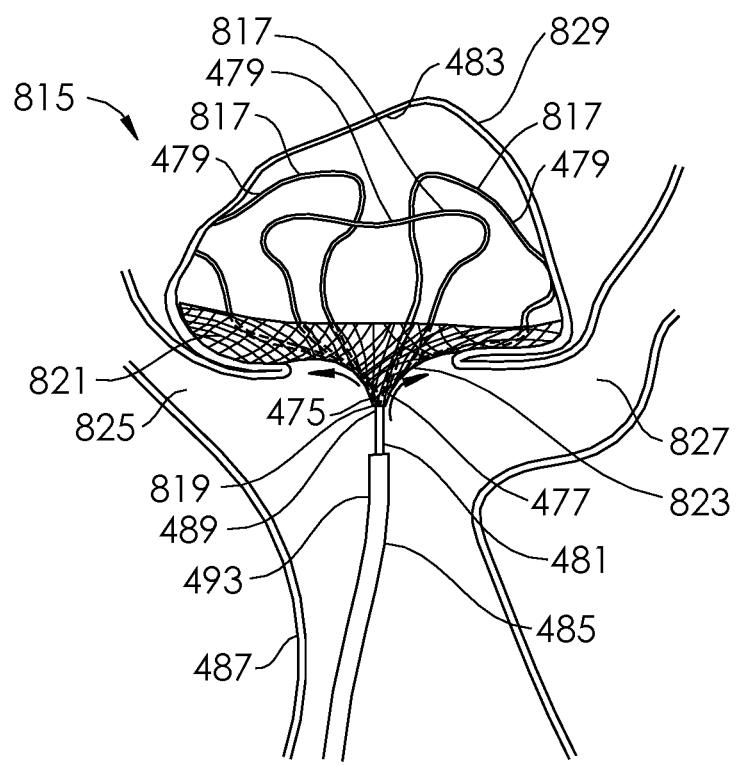
FIG. 7 illustrates an occlusion device delivered into a terminal aneurysm, according to an embodiment of the present disclosure.

FIG. 7 illustrates an occlusion device 815 deployed within an aneurysm and having several wire forms 817 (three shown) that loop back and attach to a proximal end 819 of the occlusion device 815 at each of their ends (first end 475, second end 477). The loop portions 479 of the wire forms 817 are configured to grip within the aneurysm 829 by interfacing with the aneurysm wall 483. A proximal mesh 821 includes a circumferentially-extending concave portion 823 that is configured to divert or steer blood flow toward side arteries 825, 827 as shown in curved arrows. The occlusion device 815 is shown in FIG. 7 within a terminal aneurysm 829 (e.g., basilar tip or other terminal aneurysm,). The occlusion device 815 is delivered through a microcatheter 485 that is placed through the basilar artery 487, and after being deployed in the desired position, is released from the pusher wire 481 by detachment at a detachable joint 489. A detachable joint 489 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. During delivery, the pusher wire 481 is held on its proximal end (not shown) by a user and pushed in a forward longitudinal direction, in order to advance the occlusion device 815 to the distal end 493 of the delivery catheter (microcatheter) 485.

Figure 8:
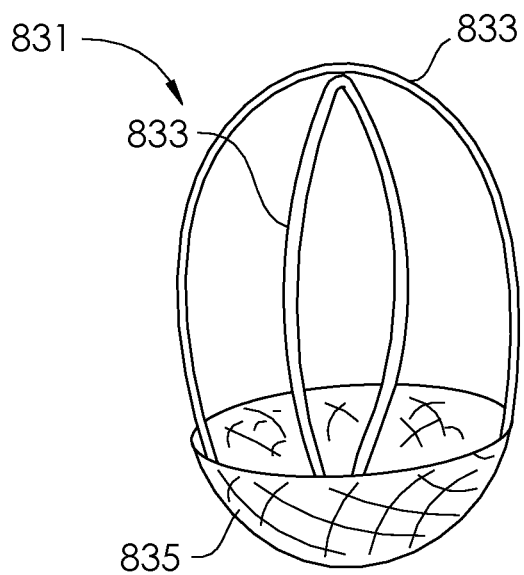
FIG. 8 is a perspective view of an occlusion device according to an embodiment of the present disclosure.

FIG. 8 is a perspective view of a basket-shaped occlusion device 831, having the general structure of the occlusion device 815 of FIG. 7, but having rounded wire forms 833 configured to conform to a dome of an aneurysm, and also to force the proximal mesh portion 835 against the neck portion of the aneurysm.

Figure 9:
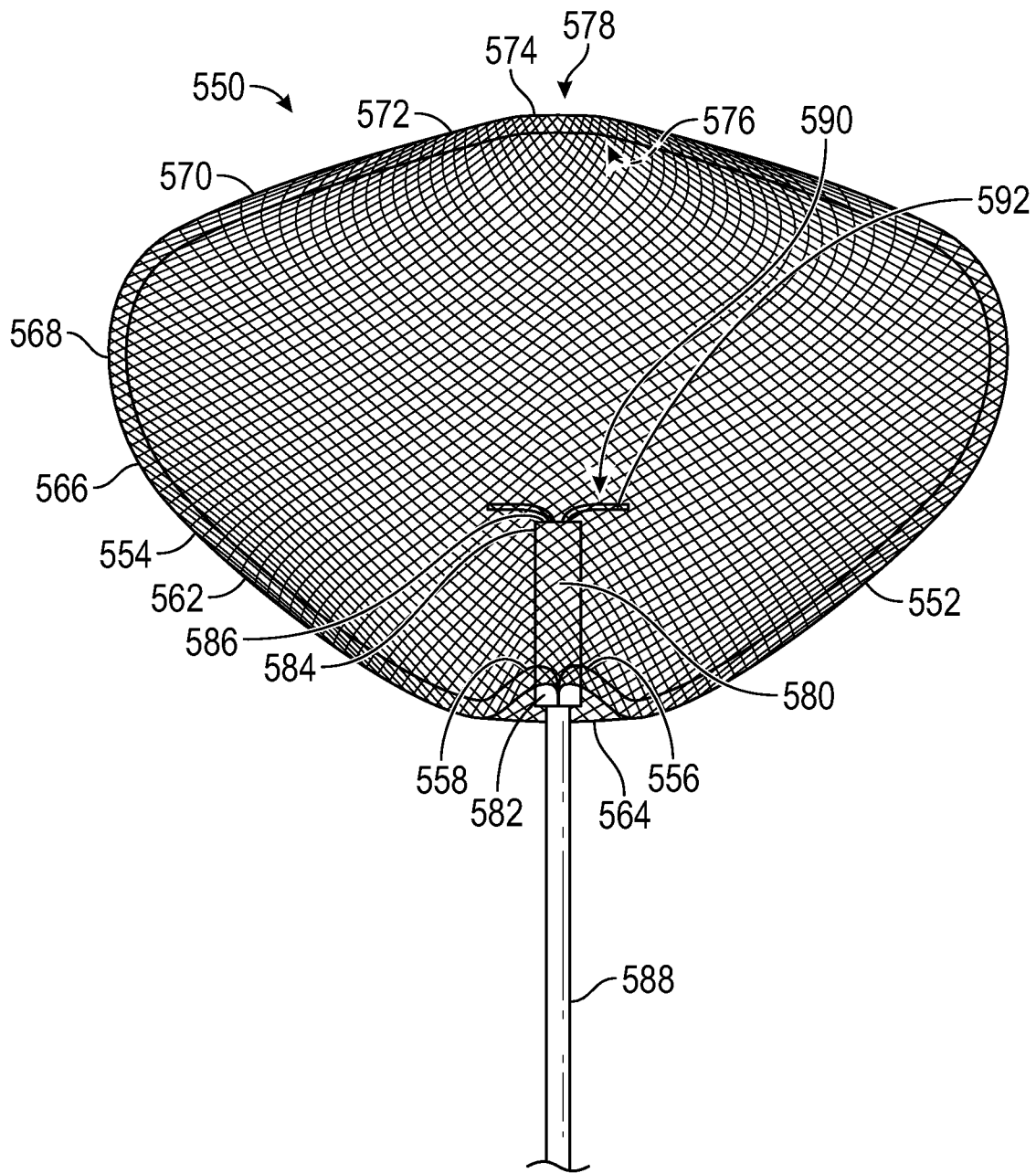
FIG. 9 is a perspective view of an occlusion device according to an embodiment of the present disclosure.

FIG. 9 illustrates an occlusion device 550 having a dual layer mesh, and comprising a disk-shaped element 552 having a disk-shaped longitudinal section. the occlusion device 550 is constructed from an inverted mesh tube 554 having a first end 556 and a second end 558, and a wall 560. The inverted mesh tube 554 extends on an outer layer 562 from the second end 558 past a proximal end 564 of the disk-shaped element 552 and along a hemisphere shape 566 to a maximum diameter portion 568. From the maximum diameter portion 568, the outer layer 562 extends radially inward and distally along a frustoconical portion 570 and along and adjacent radiused portion 572, to an inversion fold 574 from the outer layer 562 to an inner layer 576 which follows the contours of the outer layer 562 from a distal orifice 578 to the first end 556. The occlusion device 550 is fabricated as an inverted mesh tube 554 having a simple straight elongate configuration, and is subsequently formed into the shape shown in FIG. 9, and heat set into this shape. For example, the inverted mesh tube 554 may be constructed as a single layer mesh tube formed of at least some nickel-titanium alloy filaments, and then inverted on itself. The inverted mesh tube 554 may then be placed into a die or mold comprising one or more pieces, to hold it in the shape of the disk-shaped element 552. Then, the disk-shaped element 552 may be subjected to an elevated temperature and then cooled, to lock in the shape, resulting in a disk-shaped element 552 having at least some superelastic properties. An internal marker band 580 is attached at its proximal end 582 to the first end 556 and the second end 558, and can comprise a radiopaque material such as platinum or a platinum alloy such as 90% platinum and 10% iridium, or 80% platinum and 20% iridium, or 75% platinum and 25% iridium. The internal marker band 580 has a distal end 584 and a hollow lumen 586. A pusher wire 588 is inserted through the lumen 586 of the internal marker band 580 and has a distal end 590 having radially-extending protrusions 592. The disk-shaped element 552 is configured to cover a neck portion of an aneurysm. The maximum diameter portion 568 can be configured to engage a wall portion of the aneurysm to maintain the occlusion device 550 in place. For example, the diameter of the maximum diameter portion 568 can be oversized in relation to the target aneurysm diameter, e.g., 10% greater, 20% greater, etc.

FIGS. 10A and 11A-11C illustrate an occlusion device 1040 comprising a mesh cover 1042 including a distal concavity 1044. An internal tube 1046 having a lumen 1048 and an outer wall 1050 is secured within the mesh cover 1042, such that its proximal end 1052 is flush or closely adjacent to a proximal end 1054 of the mesh cover 1042. A pusher 1056 comprises a wire having a distal end 1058 including a plurality of radially-extending fingers 1060 which extend from the distal end 1058. The fingers 1060 are configured to be meltable, detachable, unbendable, breakable, ablatable, deformable, or otherwise changeable. Prior to detachment, the radially-extending fingers 1060 create a maximum diameter that is larger than the diameter of the lumen 1048 of the internal tube 1046, such that traction on the wire of the pusher 1056 causes the fingers 1060 to pull on the distal end of the outer wall 1050 of the internal tube 1046, and thus the pull the entire occlusion device 1040. For example, the occlusion device 1040 may be advanced into an aneurysm, and if the user does not believe the fit or configuration of the occlusion device 1040 within the aneurysm is desirable, the user may pull on the pusher 1056 to pull the occlusion device 1040 out of the aneurysm and into the lumen of the delivery catheter. However, then the occlusion device 1040 has been delivered into the aneurysm in an acceptable manner, the user may detach by any detachment manner (to deform, damage, or destroy the fingers 1060), via modes including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. In one embodiment, mechanical detachment is achieved by pushing the distal end of the microcatheter against the proximal end 1054 of the mesh cover 1042 while pulling on the pusher 1056, thus bending the fingers 1060, and removing the pusher 1056 from the occlusion device 1040. The internal tube 1046 provides for a smooth proximal end 1054 of the mesh cover 1042, and thus no remnant wire protruding proximally. Remnant protruding wires could cause thrombosis, which may cause embolic stroke. In some embodiments, the distal end 1058 of the pusher 1056 may taper down to as small as 0.001 inch or 0.002 inch, for example, if the distal end 1058 comprises a stainless steel wire. The internal tube 1046 may comprise a polyimide tube, and may have an internal diameter as small as 0.002 inch to 0.010 inch and an outer diameter of between about 0.003 inch and about 0.014 inch. In some embodiments there may be two fingers 1060, or three fingers 1060, or four fingers 1060, or five fingers 1060, of six fingers, 1060, or more.

Figure 10A:
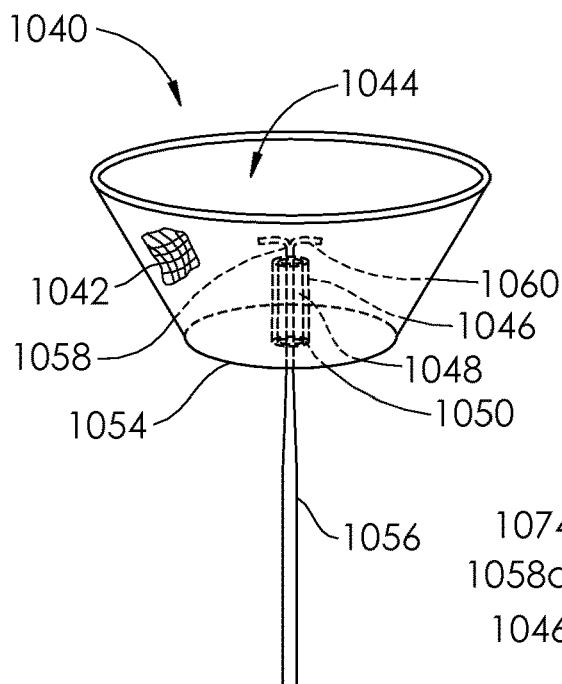
FIG. 10A is a perspective view of an occlusion device according to an embodiment of the present disclosure.
Figure 10B:
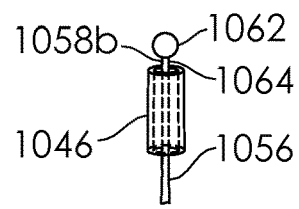
FIG. 10B is a detail view of an alternative distal end of the occlusion device of FIG. 10A, according to an embodiment of the present disclosure.
Figure 10C:
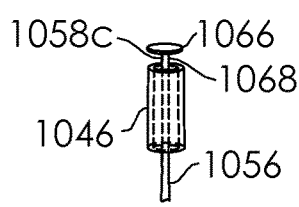
FIG. 10C is a detail view of an alternative distal end of the occlusion device of FIG. 10A, according to an embodiment of the present disclosure.
Figure 10D:
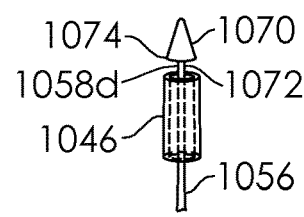
FIG. 10D is a detail view of an alternative distal end of the occlusion device of FIG. 10A, according to an embodiment of the present disclosure.
Figure 10E:
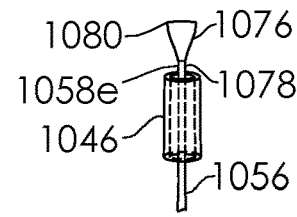
FIG. 10E is a detail view of an alternative distal end of the occlusion device of FIG. 10A, according to an embodiment of the present disclosure.
Figure 11A:
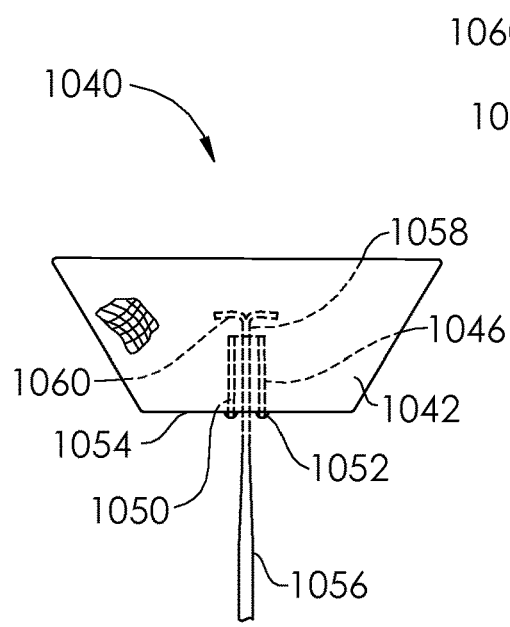
FIG. 11A is a side view of the occlusion device of FIG. 10A.
Figure 11B:
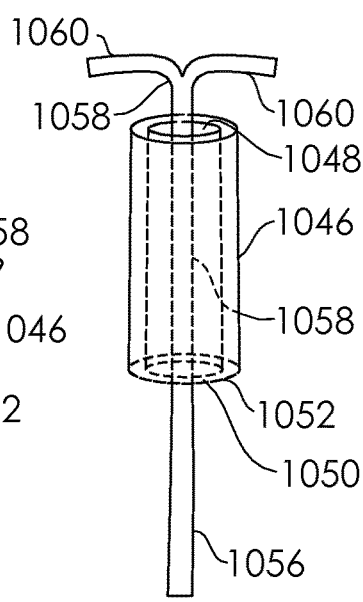
FIG. 11B is a detail view of the detachment portion of the occlusion device of FIG. 10A, prior to detachment.
Figure 11C:
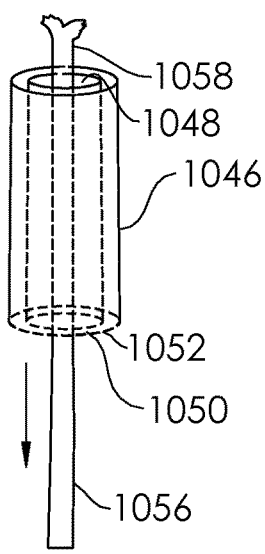
FIG. 11C is a detail view of the detachment portion of the occlusion device of FIG. 10A, during detachment.

The flush or adjacent relation of the proximal end 1052 of the internal tube 1046 to a proximal end 1054 of the mesh cover 1042 assures that there is no detachment remnant extending substantially proximal to the proximal end 1054 of the mesh cover 1042 (and into the parent artery). Thus, any potentially related thromboembolic events may be avoided, in cases wherein such a remnant would be a risk. In some embodiments, the minimum outer diameter of the mesh cover 1042 is between about 70% and about 90% of the maximum outer diameter of the mesh cover 1042. FIG. 10B illustrates an alternative distal end 1058*b* comprising a ball 1062 having a spherical or globular shape. The detachment may occur at the ball 1062, or at a portion 1064 of the distal end 1058*b* proximal to the ball 1062, or at both. The ball 1064 may be attached to the pusher 1056 by epoxy, adhesive, welding, brazing, or soldering, or may be formed from the material of distal end 1058*b* by welding. FIG. 10C illustrates an alternative distal end 1058*c* comprising a disk 1066 having a flattened, circular shape. The detachment may occur at the disk 1066, or at a portion 1068 of the distal end 1058*c* proximal to the disk 1066, or at both. The disk 1066 may be attached to the pusher 1056 by epoxy, adhesive, welding, brazing, or soldering, or may be formed from the material of distal end 1058*c* by welding. FIG. 10D illustrates an alternative distal end 1058*d* comprising a tip 1070 having a frustoconical shape. The detachment may occur at the tip 1070, or at a portion 1072 of the distal end 1058*d* proximal to the tip 1070, or at both. The tip 1070 may be attached to the pusher 1056 by epoxy, adhesive, welding, brazing, or soldering, or may be formed from the material of distal end 1058*d* by welding. FIG. 10E illustrates an alternative distal end 1058*e* comprising a tip 1076 having a flattened reverse spear shape. The detachment may occur at the tip 1076, or at a portion 1078 of the distal end 1058*e* proximal to the tip 1076, or at both. The tip 1076 may be attached to the pusher 1056 by epoxy, adhesive, welding, brazing, or soldering, or may be formed from the material of distal end 1058*e* by welding, or may be a flattened portion of the pusher 1056 wire, e.g., by rolling or pressing. In each of the alternative embodiments, the diameter (or maximum transverse dimension) of the ball 1062, the disk 1066, the proximal end 1074 of the tip 1070, or the distal end 1080 of the tip 1076 are greater than the diameter of the lumen 1048 of the internal tube 1046, thus allowing the occlusion device 1040 to be detachably locked to the pushed 1056.

Figure 12:
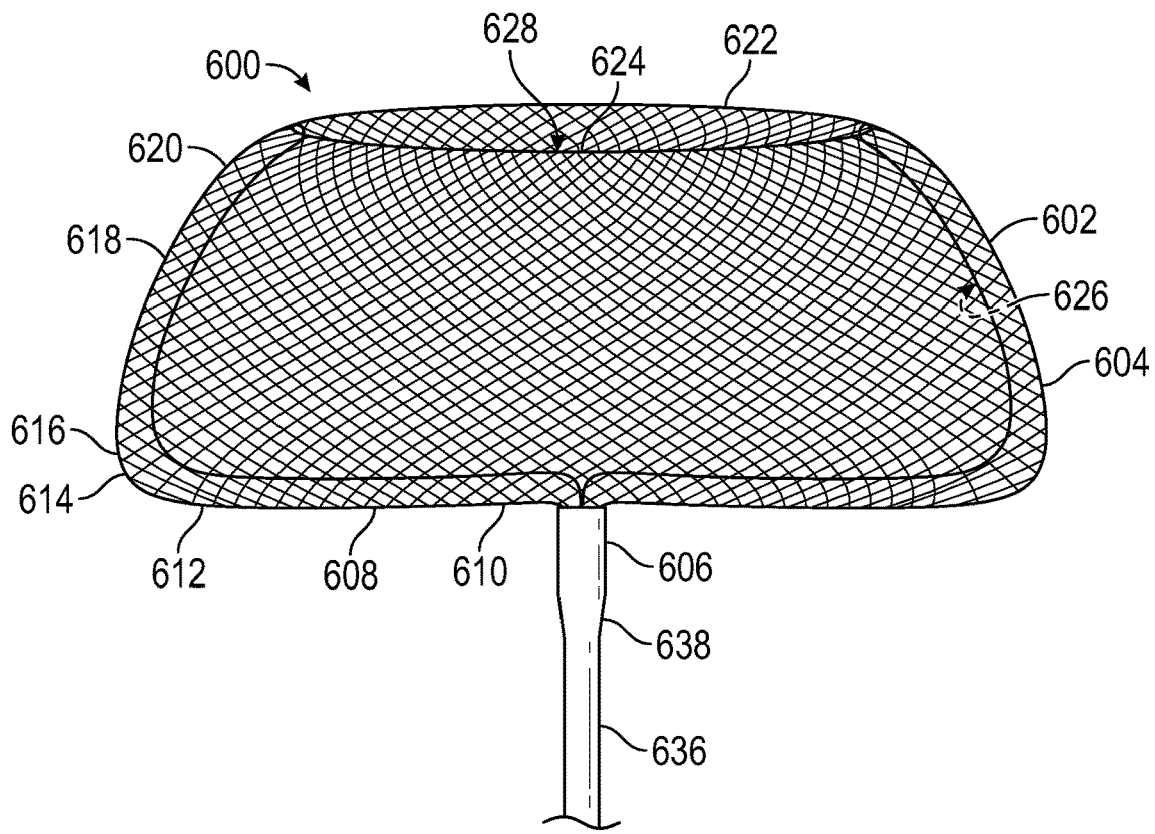
FIG. 12 is a perspective view of an occlusion device according to an embodiment of the present disclosure.

FIG. 12 illustrates an occlusion device 600 having a dual layer mesh, and comprising a single bowl-shaped element 602 having a trapezoid-shaped longitudinal section. the occlusion device 600 is constructed from an inverted mesh tube 604 having a first end and a second end (not shown), both inserted (in a collapsed state) and bonded within a marker band 606. The inverted mesh tube 604 extends on an outer layer 608 from the second end of the inverted mesh tube 604 past a proximal end 610 of the bowl-shaped element 602 and along a first substantially flattened portion 612 substantially overlaying a transverse plane, to a maximum diameter portion 614 having an acute angulation 616. From the maximum diameter portion 614, the outer layer 608 extends distally and radially inward along a frustoconical portion 618, to an obtuse angulation 620, to a second substantially flattened portion 622, to an inversion fold 624 from the outer layer 608 to an inner layer 626 which follows the contours of the outer layer 608 from a distal orifice 628 to the first end of the inverted mesh tube 604. The occlusion device 600 is fabricated as an inverted mesh tube 604 having a simple straight elongate configuration, and is subsequently formed into the shape shown in FIG. 12, and heat set into this shape. For example, the inverted mesh tube 604 may be constructed as a single layer mesh tube formed of at least some nickel-titanium alloy filaments, and then inverted on itself. The inverted mesh tube 604 may then be placed into a die or mold comprising one or more pieces, to hold it in the shape of the bowl-shaped element 602. Then, the bowl-shaped element 602 may be subjected to an elevated temperature and then cooled, to lock in the shape, resulting in a bowl-shaped element 602 having at least some superelastic properties. The marker band 606 holds the first end and the second end of the inverted mesh tube 604 together, and can comprise a radiopaque material such as platinum or a platinum alloy such as 90% platinum and 10% iridium, or 80% platinum and 20% iridium, or 75% platinum and 25% iridium.

Figure 13:
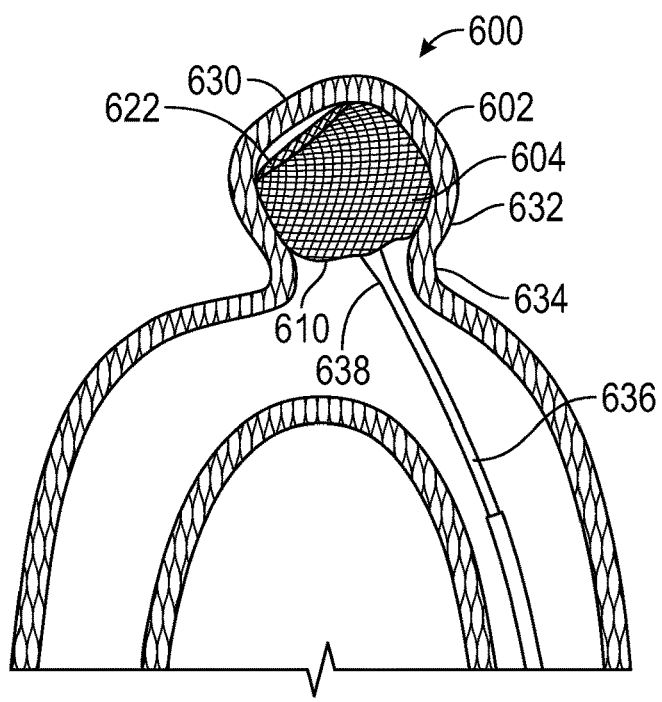
FIG. 13 is a perspective view of the occlusion device of FIG. 12 delivered into an aneurysm.

The bowl-shaped element 602 is configured to cover a neck portion of an aneurysm. The maximum diameter portion 614 can be configured to engage a wall portion of the aneurysm to maintain the occlusion device 600 in place. For example, the diameter of the maximum diameter portion 614 can be oversized in relation to the target aneurysm diameter, e.g., 10% greater, 20% greater, etc. As shown in FIG. 13, the maximum diameter portion 614 engages with an aneurysm 630 at a proximal portion 632 just distal to the neck 634 of the aneurysm 630. Because the maximum diameter portion 614 is oversized in relation to the diameter of the proximal portion 632 of the aneurysm 630, and because the maximum diameter portion 614 is at a proximal portion of the bowl-shaped element 602, the second substantially flattened portion 622 and/or the frustoconical portion 618 are able to deform as needed such that the bowl-shaped element 602 adjusts its shape to the shape of the aneurysm 630. The occlusion device 600 is detachably coupled to a pusher wire 636 at a detachable joint 638. In some embodiments, the minimum outer diameter of the bowl-shaped element 602 is between about 70% and about 90% of the maximum outer diameter of the bowl-shaped element 602.

Figure 14:
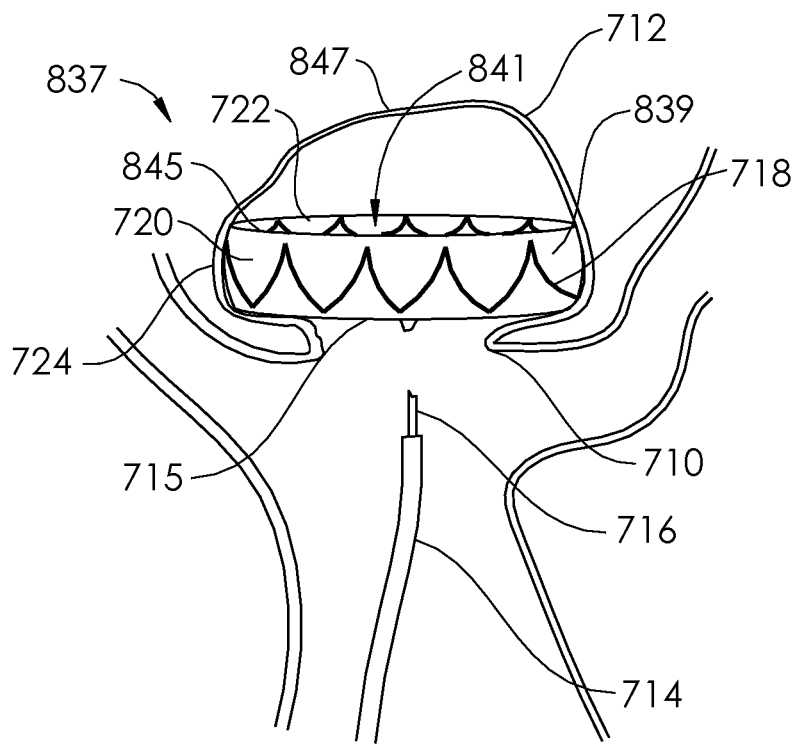
FIG. 14 is a perspective view of an occlusion device delivered into an aneurysm, according to an embodiment of the present disclosure.
Figure 15:
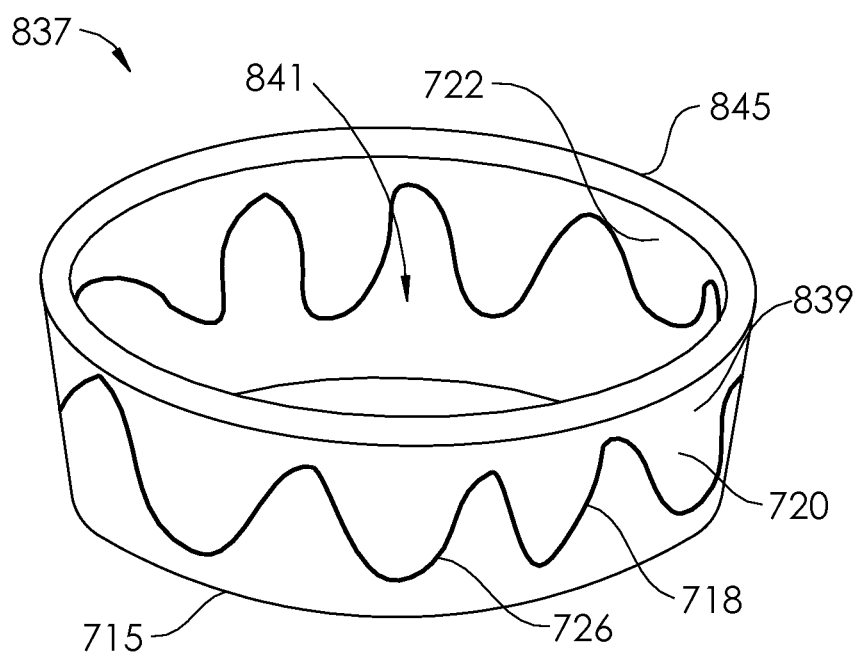
FIG. 15 is a perspective view of the occlusion device of FIG. 14.

FIGS. 14-15 illustrate an occlusion device 837 constructed from an inverted mesh tube 839 and having a proximal end 715 and a concavity 841 at its distal end 845. FIG. 14 illustrates the occlusion device 837 implanted within an aneurysm 847 having a neck 710 and a dome 712 with a microcatheter 714 and a pusher 716, as taught previously herein. The inverted mesh tube 839 includes a support stent 718 secured between an outer layer 720 and an inner layer 722 of the inverted mesh tube 839. The stent 718 is configured to apply supplemental radial force against the wall 724 of the aneurysm 847, to increase the grip of the occlusion device 837 within the aneurysm 847, adjacent the neck 710. The stent 718 allows for a larger radial force, and a better snug fit, than an inverted mesh tube 839 with no stent. The stent 718 may comprise a nickel-titanium alloy, and may be laser machined from nickel-titanium alloy tubing. The tubing may be machined by other techniques that allow slot patterns to be formed in the wall. The stent 718, after machining, may be heat formed to create an expanded diameter with superelastic characteristics. Though a "zig zag" shape 726 is shown in FIGS. 14-15, alternatively, the stent 718 may comprise modular sections, with open cell or closed cell designs. In some embodiments, the stent 718 may comprise a braided ring. In other embodiments, the stent may comprise a wire coil. In alternative embodiments, the stent is secured within both the outer layer 720 and the inner layer 722, and serve to force both of these layers toward a larger diameter. In some embodiments, the stent 718 may even be secured outside both the outer layer 720 and the inner layer 722, and function to "pull" both of these layers toward an increased outer diameter. The stent 718 may be secured to either or both of the outer layer 720 and the inner layer 722 by tying, weaving, braiding, soldering, welding, brazing, adhesive, epoxy, or other types of bonding or attachment. In some embodiments, the stent is captured within the outer layer 720 and the inner layer 722 without being directly secured to any of the mesh or either layer.

Figure 16:
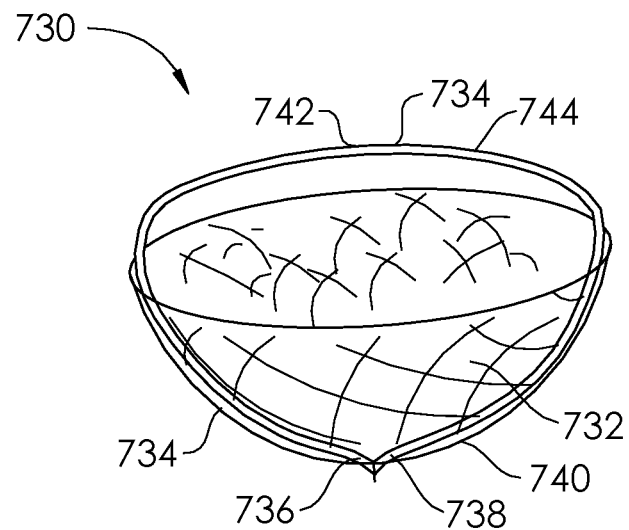
FIG. 16 is a perspective view of an occlusion device according to an embodiment of the present disclosure.

FIG. 16 illustrates an occlusion device 730 comprising a single or dual layer mesh cover 732 and having a radiopaque wire ring 734 having a first end 736 and a second end 738, both secured at the proximal end 740 of the occlusion device 730. The radiopaque wire ring 734 loops to an intermediate portion 742 at a distal end 744 of the occlusion device 730. The mesh cover 732 may comprise nickel-titanium alloy, and/or DFT, and/or platinum filaments/wires. The mesh cover 732 need not comprise DFT, platinum, or other radiopaque materials, because the radiopaque wire ring 734 comprises a radiopaque material and, because of its shape, represents the general size and shape of the occlusion device 730. In some embodiments, the radiopaque wire ring 734 comprises a platinum flat wire, giving it sufficient mass to be clearly visible on fluoroscopy or x-ray, but a low profile when folded down in the minor dimension, when the occlusion device is collapsed for placement through the lumen of a microcatheter. In other embodiments, the radiopaque wire ring 734 may comprise a woven rope of radiopaque strands having a flat shape.

Figure 17:
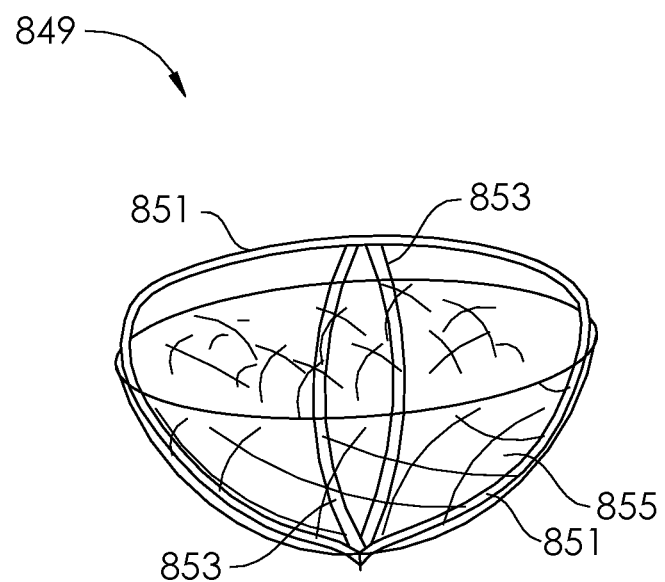
FIG. 17 is a perspective view of an occlusion device according to an embodiment of the present disclosure.

FIG. 17 illustrates an alternative version of an occlusion device 849, similar to the occlusion device 730, but having a first radiopaque wire ring 851 and a second radiopaque wire ring 853. As shown in FIG. 17, the two radiopaque wire rings 851, 853 may be generally orthogonal to each other. The two radiopaque wire rings 851, 853 secure to the single or dual layer mesh cover 855 in a similar manner to that if the occlusion device 730 of FIG. 16. The two the radiopaque wire rings 851, 853 are configured to represents the general size and shape of the occlusion device 849 in multiple axes, for example, if bi-plane fluoroscopy is not being used, or to add additional precision in bi-plane fluoroscopy. The occlusion devices 730, 849 of FIGS. 16 and 17 may also be constructed with some of all of their filaments in the mesh cover 732, 855 comprising DFT wires. A proximal marker band (not shown) may also be added to increase radiopacity.

In some embodiments, braided elements may be subsequently etched (chemical etch, photochemical etch) to decrease the overall wire diameter and decrease the stiffness.

Figure 18:
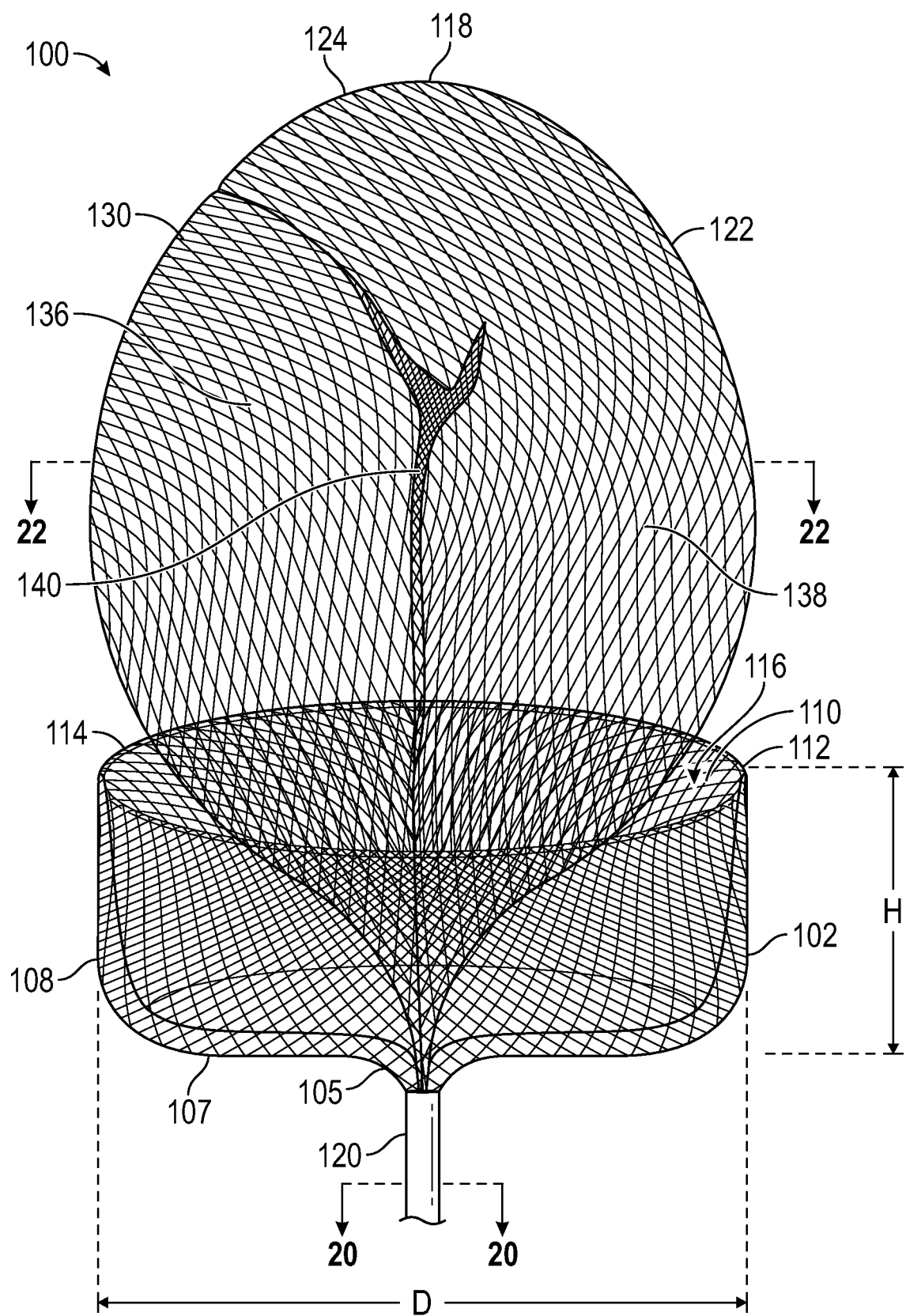
FIG. 18 is a perspective view of an occlusion device according to an embodiment of the present disclosure.

FIG. 18 illustrates an occlusion device 100 configured for placement within an aneurysm. The occlusion device 100 comprises a cover 102 having an outer diameter D. In some embodiments, the cover 102 is circular, with substantially the same diameter D at any transverse measurement around the perimeter. In other embodiments, the cover 102 is non-circular, and may comprise an ellipse, an oval, a polygon or other shapes. In the non-circular embodiments, the cover 102 comprises a minimum transverse dimension and a maximum transverse dimension. In the particular case of an ellipse or an oval shape, the cover 102 comprises a major diameter and a minor diameter. The minor diameter or minimum transverse dimension is configured to be larger than a maximum transverse dimension of an opening into the aneurysm (the neck portion). Thus, the cover 102 is configured to completely cover the neck portion, and thus to cause stagnation of blood within the aneurysm, leading to occlusion. The cover 102 is constructed from a mesh (braided) Nitinol (nickel-titanium alloy) tube 105 that is inverted on itself. The mesh tube 105 has a first end 104 and a second end 106 (see FIG. 20). The second end 106 is folded back over the outer diameter of the first end 104 thus providing an outer facing surface 108 and an inner facing surface 110. The mesh tube 105 is heat-formed such that cover 102 comprises an expanded portion and the first end 104 and second end 106 comprise unexpanded (or partially expanded) portions. A smooth fold 112 extends around the circumference 114 of the cover 102 and represents the transition between the outer facing surface 108 and the inner facing surface 110. The fold 112 avoids any sharp edge that might risk rupture of an aneurysm wall, or other anatomical damage. The cover 102 includes a concavity 116 facing toward the distal end 118 of the occlusion device 100 and away from the proximal end 120 of the occlusion device 100. The cover 102 is fabricated as an inverted mesh tube 105 having a simple straight elongate configuration, and is subsequently formed into the shape shown in FIG. 18, and heat set into this shape. For example, the inverted mesh tube 105 may be constructed as a single layer mesh tube formed of at least some nickel-titanium alloy filaments, and then inverted on itself. The inverted mesh tube 105 may then be placed into a die or mold comprising one or more pieces, to hold it in the shape of the cover 102. Then, the cover 102 may be subjected to an elevated temperature and then cooled, to lock in the shape, resulting in a cover 102 having at least some superelastic properties. The cover 102 includes a lower portion 107 opposite the fold 112. The lower portion 170 is substantially flat, generally defining a plane, but in other embodiments may have a more frustoconical or hemispheric shape.

Figure 19:
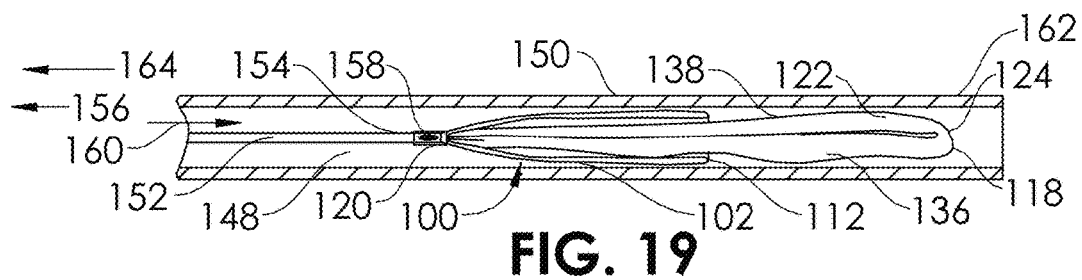
FIG. 19 is a sectional view of the occlusion device of FIG. 18 within a delivery catheter.

As formed (e.g., heat-formed), the cover 102 has an expanded configuration (shown in FIG. 18) and a collapsed configuration, shown in FIG. 19. The cover 102 comprises two mesh layers, provided by the outer facing surface 108 and the inner facing surface 110. In some embodiments, the cover 102 may comprise some nickel-titanium alloy filaments and some radiopaque elements, comprising platinum, gold, tantalum, or alloys of any of these or other radiopaque materials. In some embodiments, the filaments may comprise drawn filled tubes (DFT), such as those comprising a nickel-titanium alloy outer wall and a platinum core. The radiopaque material allows the cover 102 to be visible on radiographs or fluoroscopy. The occlusion device 100 may be configured by controlling how much radiopaque material is used, by either the ratio of radiopaque filaments to non-radiopaque filaments, or by the amount of platinum core in the drawn filled tubes. In this manner, the cover 102 can be selectively fabricated to be sufficiently visible, but not over visible, e.g., overly bright, such that other objects are obscured. In some embodiments, whether any of the filaments comprise radiopaque materials or not, a marker band may be attached to the proximal end 120 of the occlusion device 100, by adhesive or epoxy bonding, or swaging, welding or other mechanical attachment.

Figure 20:
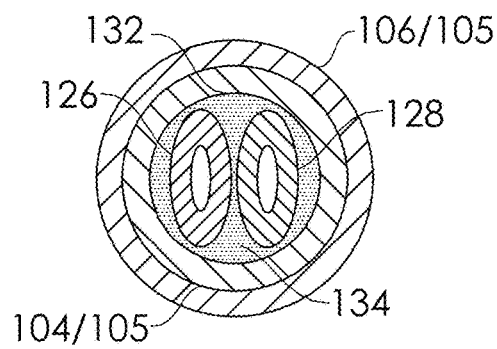
FIG. 20 is a cross-sectional view of the occlusion device of FIG. 18 taken through line 20-20.
Figure 21:
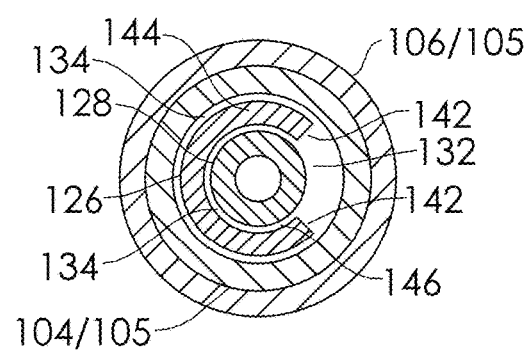
FIG. 21 is a cross-sectional view of an alternative embodiment of the present disclosure.

Extending from the concavity 116 is a doubled-over or looped tubular mesh 122 having a smooth apex 124 configured to safely contact an interior wall of an aneurysm. The tubular mesh 122 has a first end 126 and a second end 128, and an intermediate portion 130 extending between the first end 126 and second end 128. In the embodiment shown in FIG. 18, the first end 126 and second end 128 are substantially unexpanded and are inserted within a lumen 132 within the inverted mesh tube 105 that forms the cover 102, particularly at the first end 104 and a second end 106 of the mesh tube 105 that forms the cover 102 (FIG. 20). The first end 126 and second end 128 of the tubular mesh 122 can be bonded into the lumen 132 with adhesive 134, or alternatively with epoxy, or welded or bonded with any other securement technique. The first end 126 and second end 128 may each be compressed or deformed into an oval, elliptical, or D-shape, so that they may more efficiently fit into a circular cross-section of the lumen 132. An alternative configuration is shown in FIG. 21, wherein the first end 126 includes a cut 142 in its wall 144, which allows the second end 128 to be inserted into the internal space 146 at the first end 126. Thus, the second end 128 is held within the first end 126, and the first end 126 and second end 128 are secured within the lumen 132, e.g., with adhesive, epoxy, welding or other securing techniques. The tubular mesh 122 is constructed from a mesh (braided) Nitinol (nickel-titanium alloy) tube, and may also include filaments of platinum or other radiopaque materials, as well as the nickel-titanium filaments. Drawn filled tubes may also be utilized.

Figure 22:
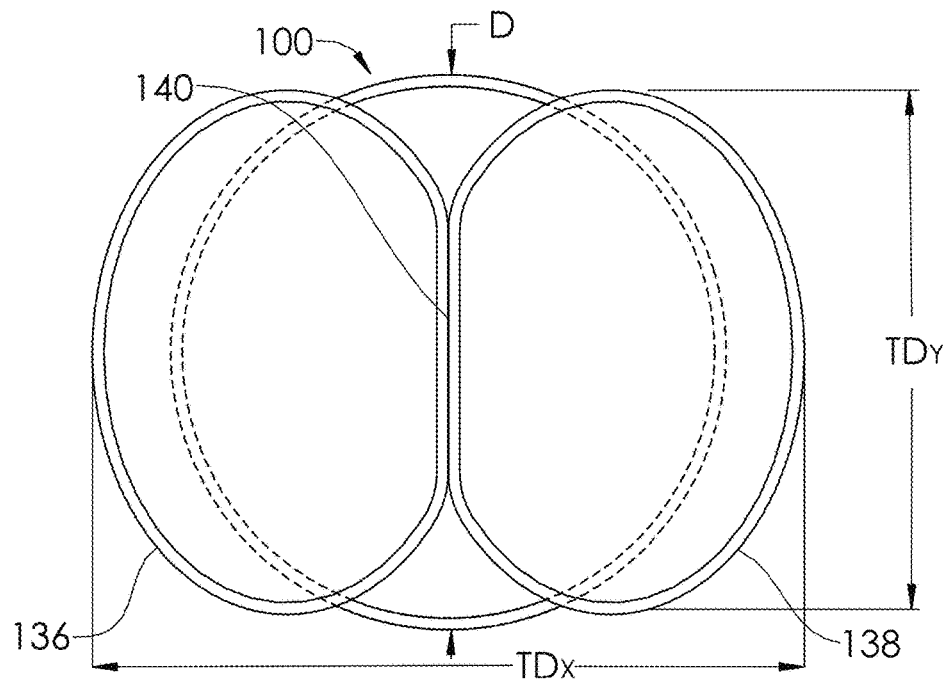
FIG. 22 is a cross-sectional view of the of the occlusion device of FIG. 18 taken through line 22-22.

Between the apex 124 of the intermediate portion 130 and the first and second ends 126, 128, the tubular mesh 122 intermediate portion 130 also comprises a first leg 136 and a second leg 138, extending therefrom. Each of the first leg 136 and second leg 138 comprises a different section of the tubular mesh 122. Thus, the tubular mesh 122 is a single layer mesh (braided) tube extending from its first end 126 through the first leg 136 and around the apex 124, then through the second leg 138 to the second end 128. In the embodiment shown in FIG. 18, the first leg 136 and second leg 138 are shown in their substantially unrestrained, expanded states, and, in this embodiment, the first leg 136 and second leg 138 each have a large enough diameter such that they contact each other at a central axis 140. Turning to FIG. 22, it can be appreciated that the first leg 136 and second leg 138 each form a more oval or elliptical cross-sectional shape, rather than a circular shape, because of their opposition to each other at the central axis 140. Also, the first leg 136 and second leg 138 together form a first transverse dimension $TD_X$ and a second transverse dimension $TD_Y$. In this embodiment, the first transverse dimension $TD_X$ is greater than the second transverse dimension $TD_Y$. In other embodiments, the first transverse dimension $TD_X$ is less than the second transverse dimension $TD_Y$. In some embodiments, the first transverse dimension $TD_X$ is equal to the second transverse dimension $TD_Y$. In some cases, the first transverse dimension $TD_X$ is configured to contact an interior wall of an aneurysm, to stabilize the occlusion device 100 within the aneurysm, while the second transverse dimension $TD_Y$ is not. In some cases, the second transverse dimension $TD_Y$ is configured to contact an interior wall of an aneurysm, to stabilize the occlusion device 100 within the aneurysm, while the first transverse dimension $TD_X$ is not. In some cases, the occlusion device 100 may be placed into a non-circular aneurysm, and in these cases, the first transverse dimension $TD_X$ and the second transverse dimension $TD_Y$ may each be configured to contact an interior wall of an aneurysm at different circumferential locations, as the aneurysmal cross-section may be more oval or elliptical, or another non-circular shape.

Returning to FIG. 19, the occlusion device 100 is shown with both the cover 102 and the tubular mesh 122 in their collapsed or compacted configurations while it is placed into the lumen 148 of a delivery catheter 150 having a distal end 162 and a proximal end 164. The delivery catheter 150 may be a microcatheter having a luminal diameter of 0.017 inch or 0.021 inch, 0.025 inch, or 0.028 inch, or other sizes. An elongate pusher 152, having a distal end 154 and a proximal end 156, may comprise a wire, a hypo tube, or another elongate structure having column support, and is detachably coupled at its distal end 154 to the proximal end 120 of the occlusion device 100. A detachable joint 158 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. During delivery, the pusher 152 is held on its proximal end 156 by a user and pushed in a forward longitudinal direction 160, in order to advance the occlusion device 100 to the distal end 162 of the delivery catheter 150.

Figure 23:
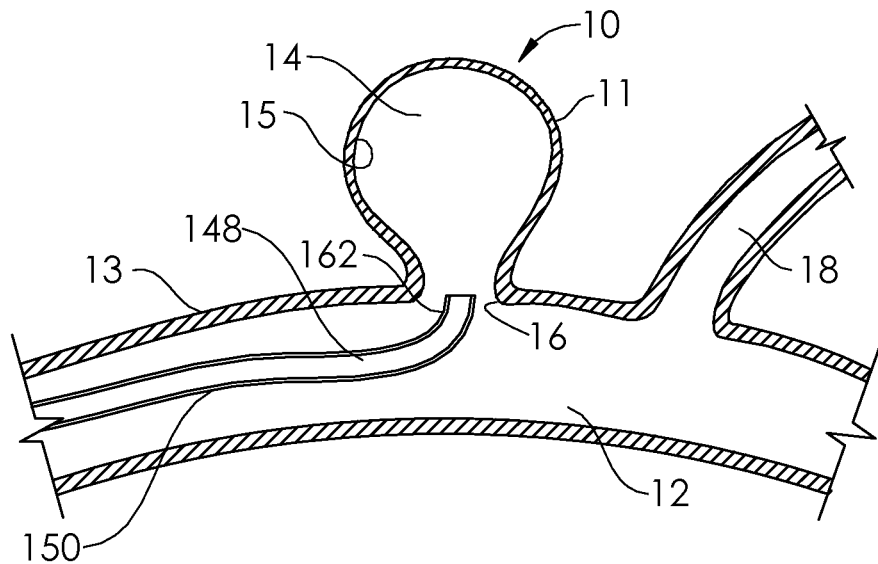
FIGS. 23-26 illustrate the implantation of the occlusion device of FIG. 18 in an aneurysm of a blood vessel of a patient.

In FIGS. 23-26, an aneurysm 10 having a neck portion 16 is shown. The occlusion device 100 is shown in use being implanted by a user (e.g., physician) into the aneurysm 10 through the delivery catheter 150 to disrupt or halt the flow of blood flow between the blood vessel 12 and the internal volume 14 of the aneurysm 10, thereby reducing the likelihood that the aneurysm 10 will rupture. Or, in cases in which the aneurysm 10 has already ruptured, the occlusion device 100 is being implanted to help heal the rupture and/or to prevent rerupture. The occlusion device 100 is configured to be low profile device, minimizing disruptions to surrounding bodies, such as a side branch 18 of the blood vessel 12. The blood vessel 12 has a blood vessel wall 13 and the aneurysm 10 has an aneurysm wall 11. In FIG. 23, the delivery catheter 150 is advanced through a sheath and/or guiding catheter (not shown) through a puncture or cutdown in a peripheral blood vessel, such as a femoral artery, a brachial artery, or a radial artery. The distal end 162 of the delivery catheter 150 may be shaped with a curve, as shown, either by the manufacturer, or prior to the procedure by the user, in order to allow for improved backup support when delivering the occlusion device 100, as well as to aid deliverability into the aneurysm 10. The distal end 162 of the delivery catheter 150 is placed adjacent the neck portion 16 of the aneurysm 10. The delivery catheter 150 may first be advanced over a guidewire (not shown) that is passed through the lumen 148. The guidewire may then be removed, leaving the lumen 148 as a delivery conduit and the delivery catheter 150 as a support column.

Figure 24:
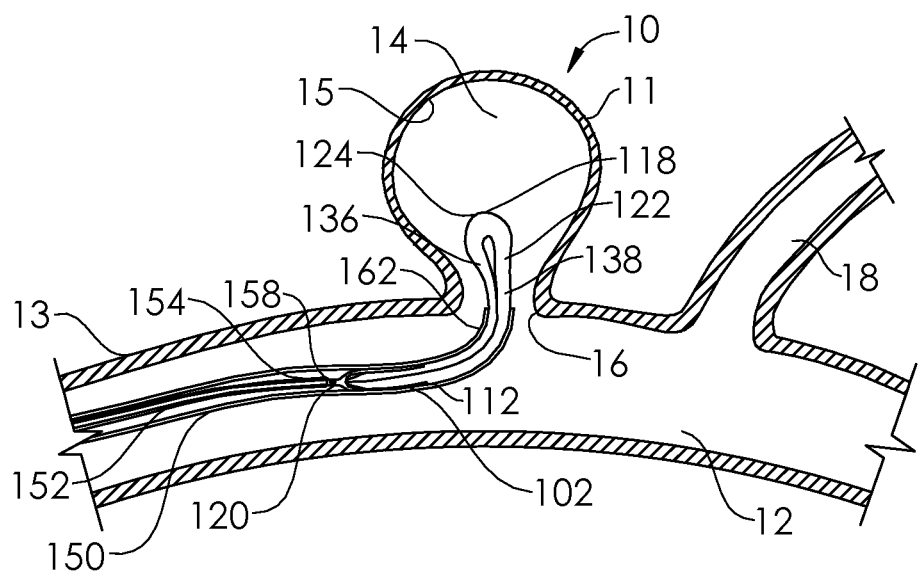
Figure 25:
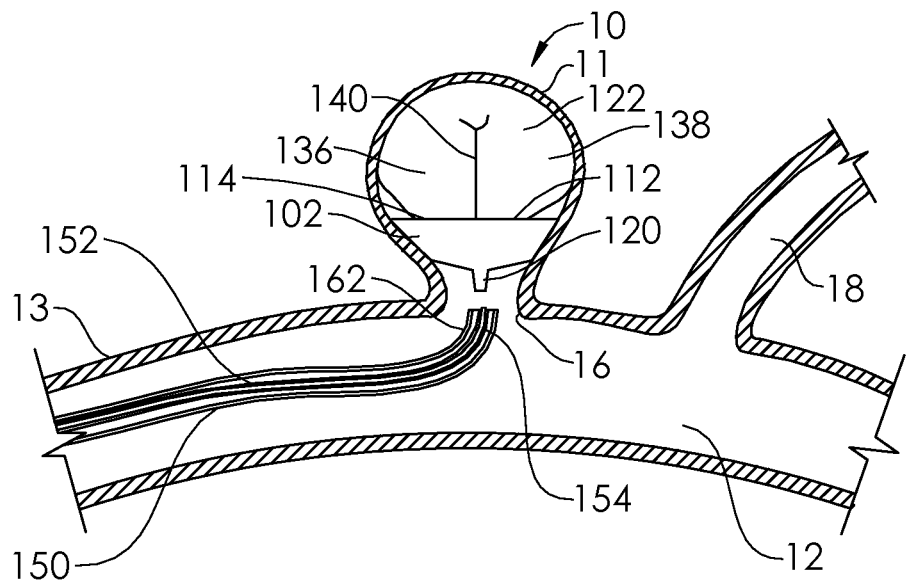

In FIG. 24, the occlusion device 100 is advanced through the lumen 148 of the delivery catheter 150, as described, and the distal end 118 of the occlusion device 100, having a smooth apex 124 (of a curve in the tubular mesh 122) is advanced out of the lumen 148 and into the internal volume 14 of the aneurysm 10. The smooth apex 124 is the first portion of the occlusion device 100 that exits the lumen 148 and thus is the first portion of the occlusion device to enter the aneurysm 10. The smooth apex 124, because of its curved and contoured surface as well as its flexible mesh wall, is a blunt, soft, and atraumatic element that is configured to first contact the interior surface 15 of the aneurysm 10. The smooth apex 124 can contact the interior surface 15 and slide around the interior surface 15 is a less traumatic manner than most devices that are configured to implant into an aneurysm, such as small diameter detachable coils. The atraumatic characteristics of the smooth apex 124 make it fully deployable not only in unruptured cerebral aneurysms, but also in ruptured cerebral aneurysms, where certain other devices may be contraindicated. In FIG. 25, the occlusion device 100 is shown in a substantially expanded configuration within the internal volume 14 of the aneurysm 10. The cover 102 is expanded against the interior surface 15 of the aneurysm 10, and covers the neck portion 16 of the aneurysm. The tubular mesh 122 is expanded against the interior surface 15 of the aneurysm 10, at least at one or more portions, and serves to anchor or stabilize the cover 102 in the aneurysm 10 and adjacent the neck portion 16.

Figure 26:
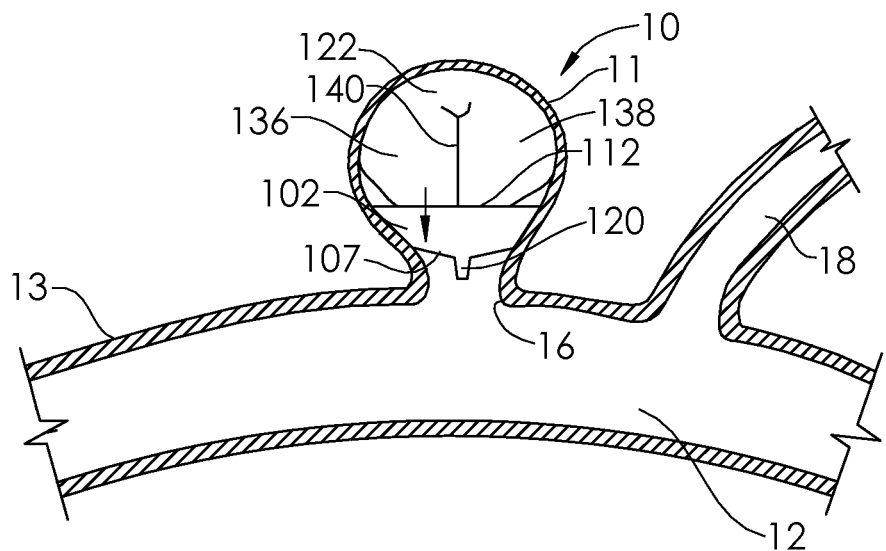

Also, in FIG. 25, the detachable joint 158 has been detached, and thus, the free end 154 of the pusher 152 can be pulled into the lumen 148 of the delivery catheter 150. In some embodiments, the delivery catheter 150 is maintained over the detachable joint 158 during the detachment procedure, to further protect the aneurysm 10. In FIG. 26, the delivery catheter 150 is removed, and the deployed occlusion device 100 is in place to begin to occlude the internal volume 14 of the aneurysm 10. The expanded tubular mesh 122 also serves to force the cover 102 against the neck portion 16 and/or against the interior surface 15, see straight arrow in FIG. 26. The dual layers of mesh in the cover 102 at the lower portion 107 (FIGS. 18 and 26) aid in the disruption of blood flow into the aneurysm 10, thus causing thrombosis to isolate the internal volume 14 of the aneurysm 10 from blood flow through the blood vessel. 12. The force (straight arrow) maintaining the cover 102 in place further assures this process, and also protects against undesired compaction over time of the occlusion device 100, whether it be compaction in the longitudinal direction or compaction in a transverse or radial direction.

Figure 27:
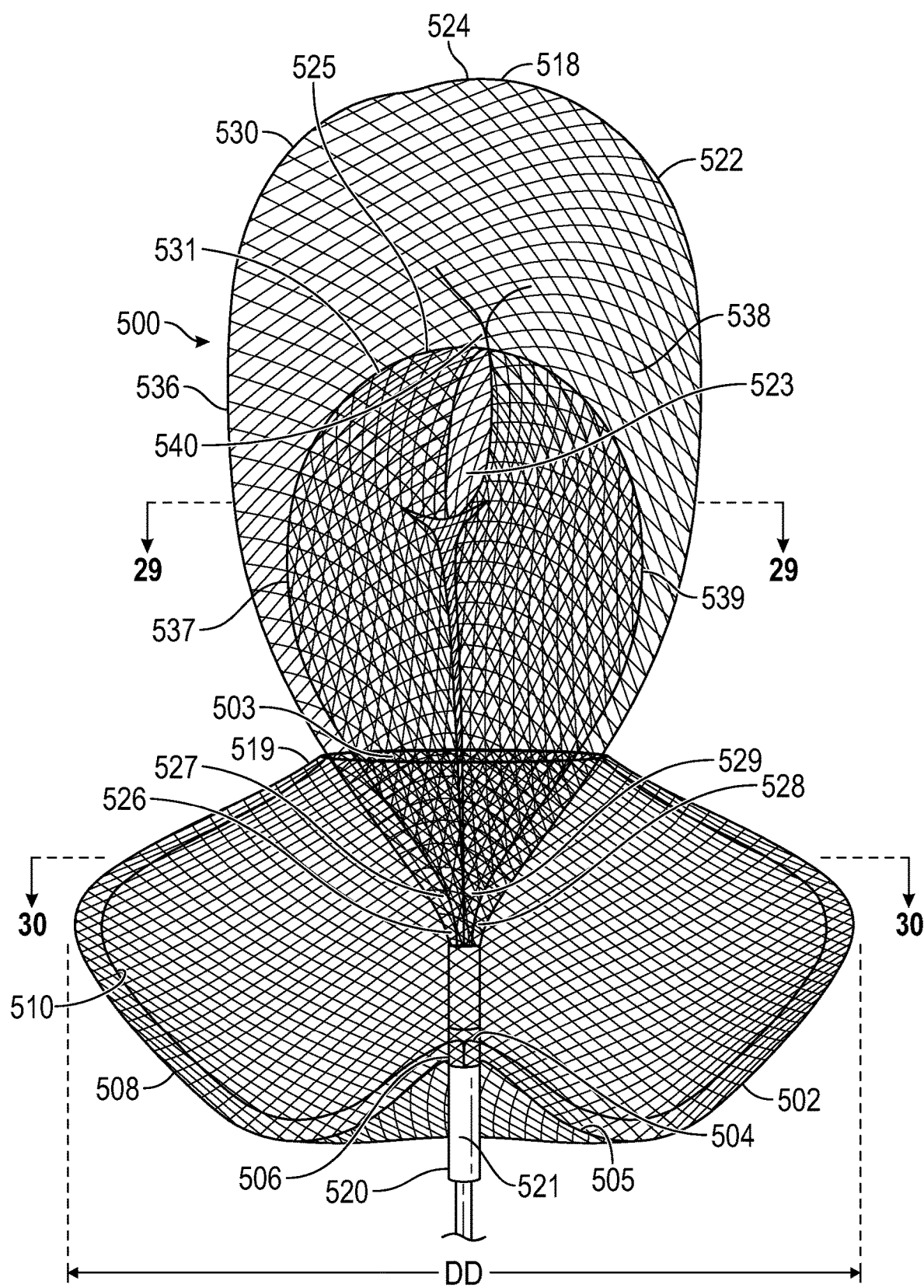
FIG. 27 is a perspective view of an occlusion device according to an alternative embodiment of the present disclosure.
Figure 30:
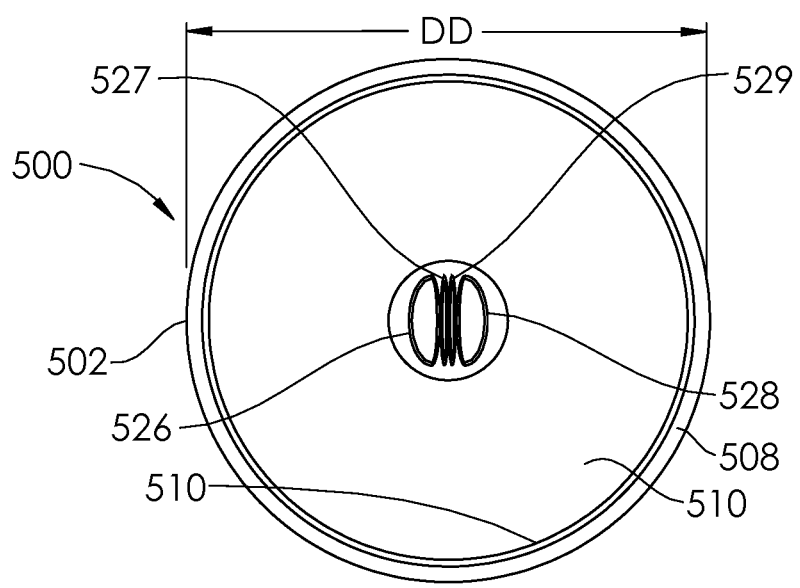
FIG. 30 is a cross-sectional view of the of the occlusion device of FIG. 27 taken through line 30-20.

FIG. 27 illustrates an occlusion device 500 configured for placement within an aneurysm. The occlusion device 500 is an alternative configuration of the occlusion device 100 of FIG. 18, comprises a cover 502 having an outer diameter DD. In some embodiments, the cover 502 is circular, with substantially the same diameter DD at any measurement around the perimeter at each transverse plane. In other embodiments, the cover 502 is non-circular, and may comprise a cross-section having an ellipse, an oval, a polygon or other shapes. In the non-circular embodiments, the cover 502 comprises a minimum transverse dimension and a maximum transverse dimension. In the particular case of an ellipse or an oval shape, the cover 502 comprises a major diameter and a minor diameter. The minor diameter or minimum transverse dimension is configured to be larger than a maximum transverse dimension of an opening into the aneurysm (the neck portion). Thus, the cover 502 is configured to completely cover the neck portion, and thus to cause stagnation of blood within the aneurysm, leading to occlusion. The cover 502 is constructed from a mesh (braided) Nitinol (nickel-titanium alloy) tube 505 that is inverted on itself. The mesh tube 505 has a first end 504 and a second end 506 (FIG. 28), similar to the first end 104 and second end 106 of FIG. 20. The second end 506 is folded back over the outer diameter of the first end 504 thus providing an outer facing surface 508 and an inner facing surface 510 (FIG. 30). The mesh tube 505 is heat-formed such that cover 502 comprises an expanded portion and the first end 504 and second end 506 comprise unexpanded (or partially expanded) portions. The heat forming may be done as described in relation to the occlusion device 100 of FIG. 18. The cover 502 has a general disk shape defined by the outer facing surface 508. In some embodiments, the cover 502 may comprise a toroidal, partially-toroidal shape. The occlusion device 500 includes a distal end 518 and a proximal end 520. As formed (e.g., heat-formed), the cover 502 has an expanded configuration (shown in FIG. 27) and a collapsed configuration, shown in FIG. 28. The cover 502 comprises two mesh layers, provided by the outer facing surface 508 and the inner facing surface 510. In some embodiments, the cover 502 may comprise some nickel-titanium alloy filaments and some radiopaque elements, comprising platinum, gold, tantalum, or alloys of any of these or other radiopaque materials. In some embodiments, the filaments may comprise drawn filled tubes (DFT), such as those comprising a nickel-titanium alloy outer wall and a platinum core. The radiopaque material allows the cover 502 to be visible on radiographs or fluoroscopy. The occlusion device 500 may be configured by controlling how much radiopaque material is used, by either the ratio of radiopaque filaments to non-radiopaque filaments, or by the amount of platinum core in the drawn filled tubes. In this manner, the cover 502 can be selectively fabricated to be sufficiently visible, but not over visible, e.g., overly bright, such that other objects are obscured. In some embodiments, whether any of the filaments comprise radiopaque materials or not, a marker band 521 may be attached to the proximal end 520 of the occlusion device 500, by adhesive or epoxy bonding, or swaging, welding or other mechanical attachment.

Figure 29:
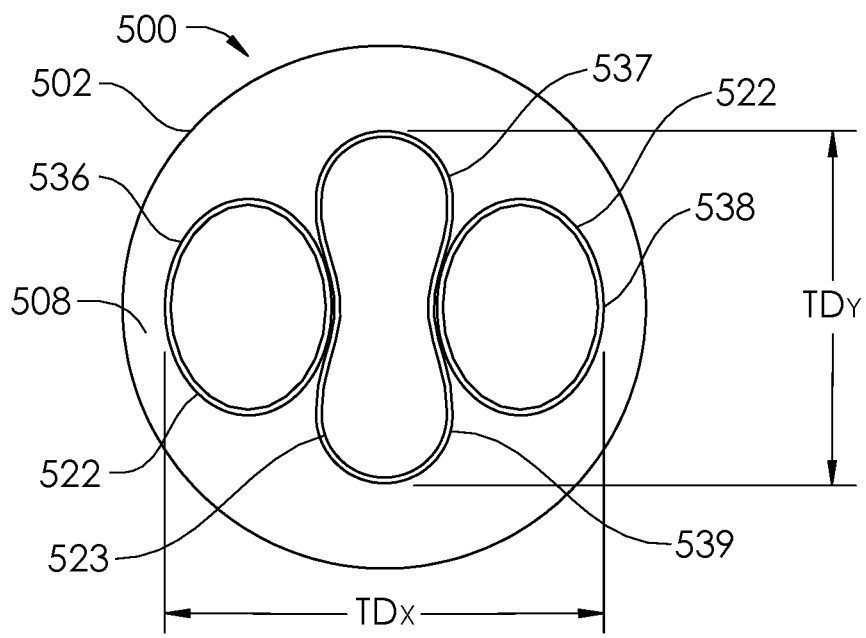
FIG. 29 is a cross-sectional view of the of the occlusion device of FIG. 27 taken through line 29-29.

Extending from an opening 503 in a distal portion 519 the cover 502 is a first doubled-over or looped tubular mesh 522 and a second doubled-over or looped tubular mesh 523. The first looped tubular mesh 522 has a smooth apex 524 configured to safely contact an interior wall of an aneurysm. The second looped tubular mesh 523 has an apex 525 configured to fit within a central axis 540 of the first tubular mesh 522. The first tubular mesh 522 and the second tubular mesh 523 are oriented at non-parallel planes to one another. As shown in FIG. 29, in one embodiment, the first tubular mesh 522 and the second tubular mesh 523 are orthogonal to each other, and substantially follow orthogonal planes, or planes at right angles to one another. The first tubular mesh 522 has a first end 526 and a second end 528, and an intermediate portion 530 extending between the first end 526 and second end 528. In the embodiment shown in FIG. 27, the first end 526 and second end 528 are substantially unexpanded and are inserted within a lumen (not shown) within the inverted mesh tube 505 that forms the cover 502, in a similar manner to the first end 104 and the second end 106 in FIG. 20. Similarly, the second tubular mesh 523 has a first end 527 and a second end 529, and an intermediate portion 531 extending between the first end 527 and second end 529. In the embodiment shown in FIG. 27, the first end 527 and second end 529 are substantially unexpanded and are inserted within a lumen (not shown) within the inverted mesh tube 505 that forms the cover 502. The first ends 526, 527 and second ends 528, 529 of the first tubular meshes 522, 523 can be bonded into the lumen with adhesive, or alternatively with epoxy, or welded or bonded with any other securement technique. The first ends 526, 527 and second ends 528, 529 may each be compressed or deformed into an oval, elliptical, or D-shape, so that they may more efficiently fit into a circular cross-section of the lumen. The alternative configuration of FIG. 21 may also be employed. The first tubular mesh 522 and second tubular mesh 523 may each be constructed from a mesh (braided) Nitinol (nickel-titanium alloy) tube, and may also include filaments of platinum or other radiopaque materials, as well as the nickel-titanium filaments. Drawn filled tubes may also be utilized.

Between the apex 524 of the intermediate portion 530 and the first and second ends 526, 528, the tubular mesh 522 intermediate portion 530 also comprises a first leg 536 and a second leg 538, extending therefrom. Between the apex 525 of the intermediate portion 531 and the first and second ends 527, 528, the tubular mesh 523 intermediate portion 531 also comprises a first leg 537 and a second leg 539, extending therefrom. In the embodiment shown in FIG. 27, the first legs 536, 537 and the second leg 538, 539 are shown in their expanded states. Turning to FIG. 29, the spacing between the first leg 536, first leg 537, second leg 538, and second leg 539 can be appreciated. Each leg 536, 537, 538, 539 may form a circular cross-sectional shape when expanded, or may form a more oval or elliptical cross-sectional shape, because of their opposition to or interface with each other. Each leg pair 536/538, 537/539 may form a first transverse dimension $TD_X$ and a second transverse dimension $TD_Y$, respectively (see FIG. 29). For example, in some embodiments, the first transverse dimension $TD_X$ may be greater than the second transverse dimension $TD_Y$. In some embodiments, the first transverse dimension $TD_X$ may be less than the second transverse dimension $TD_Y$. In some embodiments, the first transverse dimension $TD_X$ is configured to contact an interior wall of an aneurysm, to stabilize the occlusion device 500 within the aneurysm, while the second transverse dimension $TD_Y$ is not. In some embodiments, the second transverse dimension $TD_Y$ is configured to contact an interior wall of the aneurysm, while the first transverse dimension $TD_X$ is not. In some embodiments, both the first transverse dimension $TD_X$ and the second transverse dimension $TD_Y$ are configured to contact an interior wall of the aneurysm. The cover 502 may alternatively have a distal concavity, like the cover 102 of the occlusion device 100 of FIG. 18. Furthermore, the cover 102 of the occlusion device 100 of FIG. 18 may utilize a cover 502 without a distal concavity, and instead with an opening 503, as in the occlusion device 500 of FIG. 27.

Figure 28:
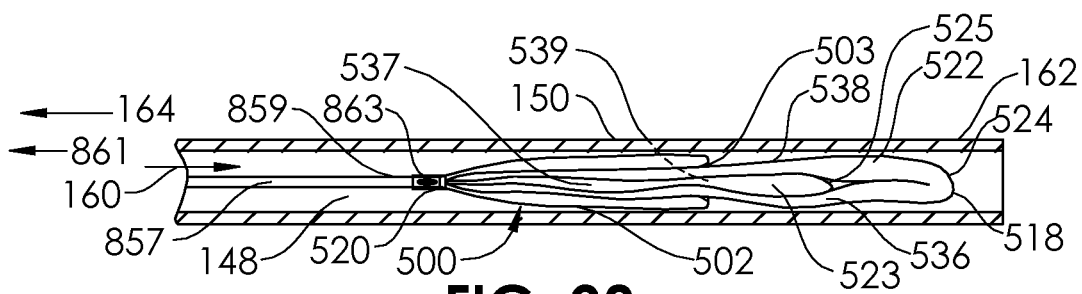
FIG. 28 is a sectional view of the occlusion device of FIG. 27 within a delivery catheter.

Turning to FIG. 28, the occlusion device 500 is shown with both the cover 502 and the tubular meshes 522, 523 in their collapsed or compacted configurations while it is placed into the lumen 148 of a delivery catheter 150 having a distal end 162 and a proximal end 164. The delivery catheter 150 may be a microcatheter having a luminal diameter of 0.017 inch or 0.021 inch, 0.025 inch, or 0.028 inch, or other sizes. An elongate pusher 857, having a distal end 859 and a proximal end 861, may comprise a wire, a hypo tube, or another elongate structure having column support, and is detachably coupled at its distal end 859 to the proximal end 520 of the occlusion device 500. A detachable joint 863 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. During delivery, the pusher 857 is held on its proximal end 861 by a user and pushed in a forward longitudinal direction 160, in order to advance the occlusion device 500 to the distal end 162 of the delivery catheter 150.

Figure 31:
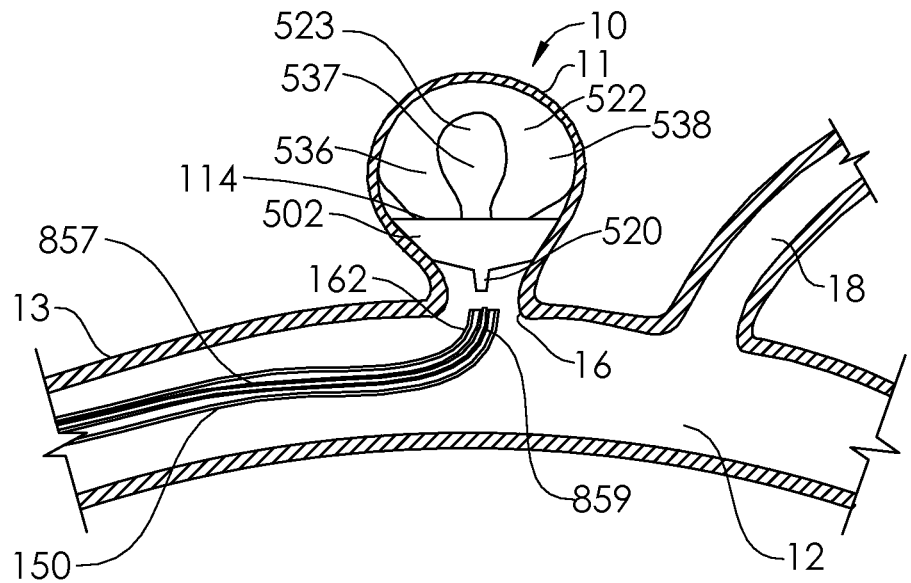
FIGS. 31-32 illustrate the implantation of the occlusion device of FIG. 27 in an aneurysm of a blood vessel of a patient.
Figure 32:
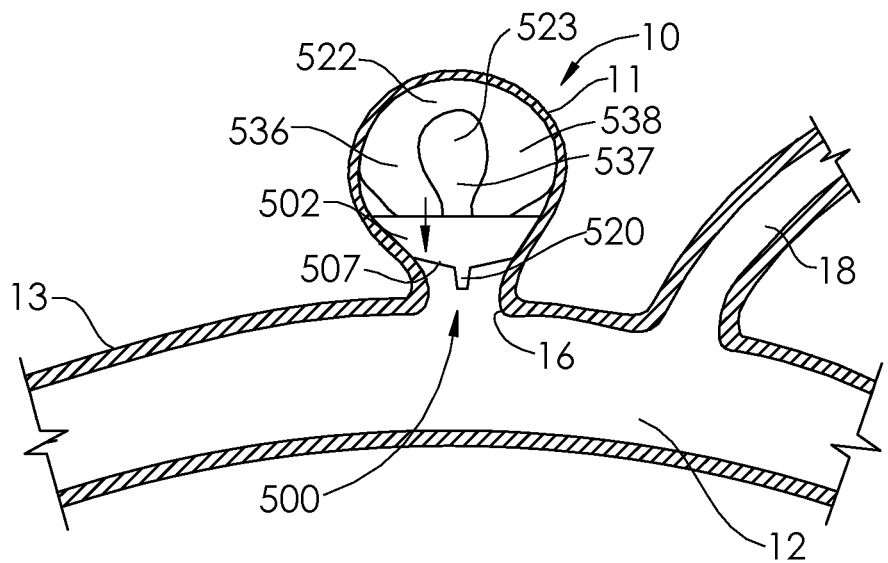

In FIG. 31, the occlusion device 500 is shown in a substantially expanded configuration within the internal volume 14 (see FIG. 23) of the aneurysm 10. The cover 502 is expanded against the interior surface 15 of the aneurysm 10, and covers the neck portion 16 of the aneurysm. One or both of the first tubular mesh 522 and the second tubular mesh 523 are expanded against the interior surface 15 (see FIG. 23) of the aneurysm 10, and serve(s) to anchor or stabilize the cover 502 in the aneurysm 10 and adjacent the neck portion 16. Also, in FIG. 31, the detachable joint 863 has been detached, and thus, the free end 859 of the pusher 857 can be pulled into the lumen 148 of the delivery catheter 150. In some embodiments, the delivery catheter 150 is maintained over the detachable joint 863 during the detachment procedure, to further protect the aneurysm 10. In FIG. 32, the delivery catheter 150 is removed, and the deployed occlusion device 500 is in place to begin to occlude the internal volume 14 of the aneurysm 10. The expanded first tubular mesh 522 and expanded second tubular mesh 523 also serve to force the cover 502 against the neck portion 16 and/or against the interior surface 15, see straight arrow in FIG. 32. The dual layers of mesh in the cover 502 at a lower portion 507 aid in the disruption of blood flow into the aneurysm 10, thus causing thrombosis to isolate the internal volume 14 of the aneurysm 10 from blood flow through the blood vessel. 12. The force (straight arrow) maintaining the cover 502 in place further assures this process, and also protects against undesired compaction over time of the occlusion device 500.

Figure 33:
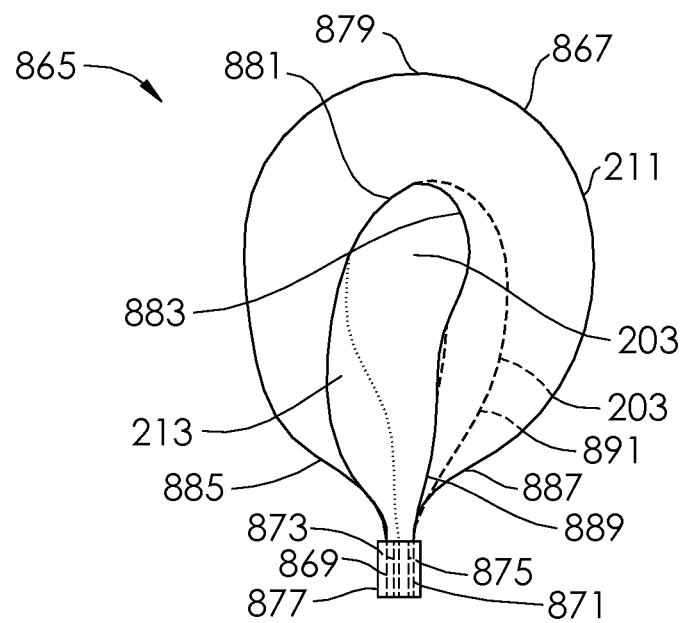
FIG. 33 is a perspective view of an occlusion device according to an alternative embodiment of the present disclosure.

FIG. 33 illustrates an occlusion device 865 comprising a first doubled-over or looped tubular mesh 867 and a second doubled-over or looped tubular mesh 203. The occlusion device 865 is similar to the occlusion device 500 of FIG. 27, however there is no cover (e.g., cover 502). The first tubular mesh 867 includes a first end 869 and a second end 871, and the second tubular mesh has a first end 873 and a second end 875. All four ends 869, 871, 873, 875 are held, in the collapsed or constrained configuration of the tubular mesh 867, 203, within a cylindrical marker band 877. The marker band 877 may comprise stainless steel or a radiopaque material such as platinum, and the ends 869, 871, 873, 875 may be bonded within a lumen of the marker band 877 with adhesive or epoxy, or may be brazed, soldered, or welded. The first looped tubular mesh 867 has an intermediate portion 211 having a smooth apex 879 configured to safely contact an interior wall of an aneurysm. The second looped tubular mesh 203 has an intermediate portion 213 having an apex 881 configured to fit within a central axis 883 of the first tubular mesh 867. The first tubular mesh 867 and the second tubular mesh 203 are oriented at non-parallel planes to one another. A shown in FIG. 33, the first tubular mesh 867 and the second tubular mesh 203 are substantially orthogonal to each other, and substantially follow orthogonal planes, or planes at right angles to one another. Because there is no cover, a first proximal portion 885 and second proximal portion 887 of the first tubular mesh 867, and a first proximal portion 889 and second proximal portion 891 of the second tubular mesh 203 are shaped and configured to serve (as did the cover 502) to be disposed against the proximal portion of an aneurysm, adjacent the neck of the aneurysm, to substantially provide occlusion of the neck.

Figure 34:
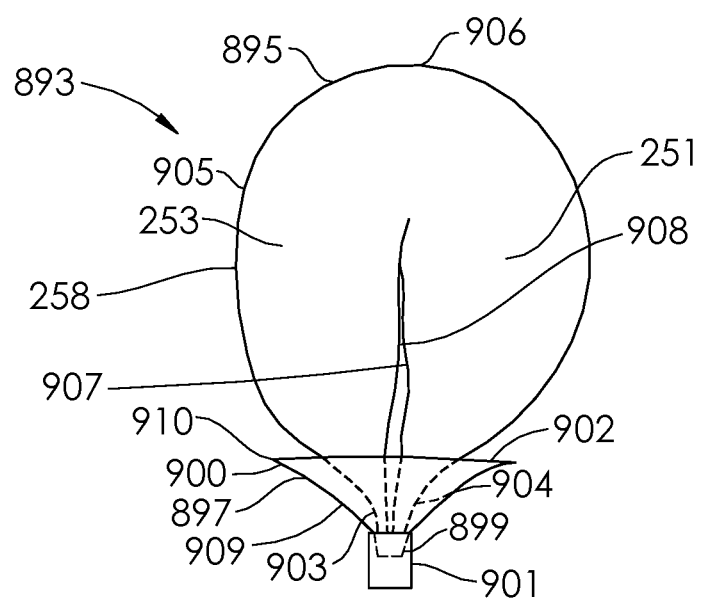
FIG. 34 is a perspective view of an occlusion device according to an alternative embodiment of the present disclosure.

FIG. 34 illustrates an occlusion device 893 comprising a doubled-over or looped tubular mesh 895 and a cover 897. The cover 897 comprises a single layer mesh tube 900 that is heat shaped as described herein. The cover 897 comprises a proximal end 899 (bonded within a marker band 901) and a flared distal end 902 that is allowed to expand freely. The tubular mesh 895 comprises a first end 903 and a second end 904 that are also bonded within the marker band 901, and an intermediate portion 905 having a smooth apex 906. An inner surface 907 of a first leg 251 of the tubular mesh 895 may be configured to touch an inner surface 908 of a second leg 253 of the tubular mesh 895 when the tubular mesh 895 is in its expanded configuration. In other embodiments, the tubular mesh may be sized and configured such that the inner surfaces 907, 908 do not typically touch each other with the tubular mesh is in its expanded configuration. A proximal face 909 of the cover 897 is configured to be disposed against the proximal portion of an aneurysm, adjacent the neck of the aneurysm, to substantially provide occlusion of the neck. A maximum diameter portion 910 of the cover 897 may be configured to engage with a wall surface on the aneurysm. Additionally, a maximum transverse dimension portion 258 of the intermediate portion 905 of the mesh tube 895 is configured to engage a wall of the aneurysm.

Figure 35:
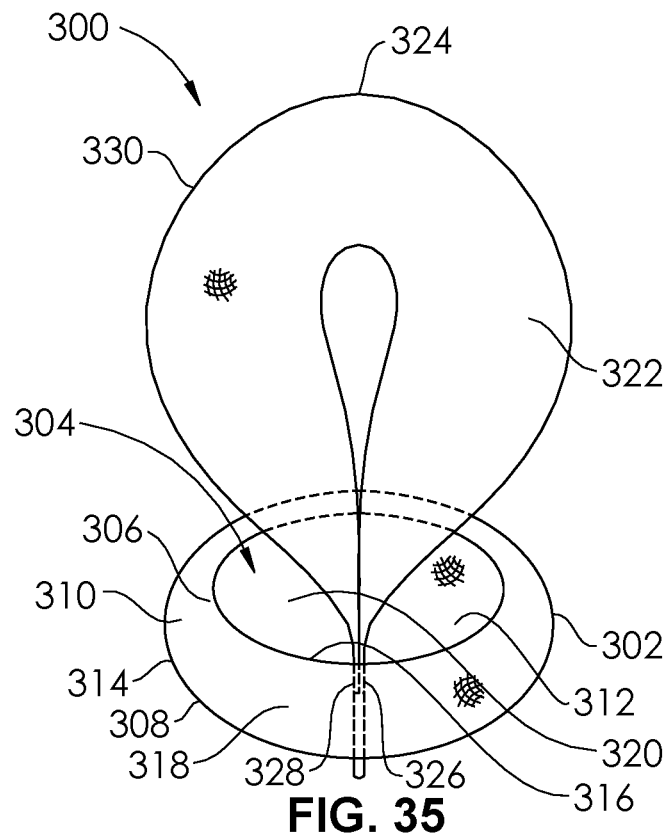
FIG. 35 is a perspective view of an occlusion device according to an alternative embodiment of the present disclosure.

FIG. 35 illustrates an occlusion device 300 comprising a cover 302 including a concavity 304 facing toward the distal end 306 of cover 302 and away from the proximal end 308 of the cover 302. The cover 302 is fabricated as an inverted mesh tube 310 having a simple straight elongate configuration, and is subsequently formed into the shape shown in FIG. 35, and heat set into this shape, as described previously herein. A smooth fold 316 extends around the distal end 306 cover 302 and represents the transition between an outer facing surface 318 and an inner facing surface 320. The occlusion device 300 is similar to the occlusion device 100 of FIG. 18, however an orifice 312 opening into the concavity 304 is smaller than the maximum diameter 314 of the cover 302. The orifice 312 has a diameter between about 35% and about 85% of the maximum diameter 314, or between about 45% and about 75%, or between about 50% and about 70%, or between about 55% and about 65%. Extending from the concavity 304 is a doubled-over or looped tubular mesh 322 having a smooth apex 324 configured to safely contact an interior wall of an aneurysm. The tubular mesh 322 has a first end 326 and a second end 328, and an intermediate portion 330 extending between the first end 326 and second end 328. The cover 302 and the tubular mesh 322 may have differing characteristics from each other in order to optimize the performance characteristics of each. In certain embodiments, the cover 302 may comprise between 36 and 144 filaments, each having a diameter between about 0.00075 to 0.001 inch. In a particular embodiment, the cover 302 may comprise 72 nickel-titanium filaments, each having a diameter of 0.00085 inch.

In certain embodiments, the tubular mesh 322 may comprise between 18 and 36 filaments, each having a diameter between about 0.00075 and 0.00125 inch. In the particular embodiment described in relation to the cover 302, the tubular mesh is constructed from 24 nickel titanium filaments, each having a diameter of 0.00093 inch. The particular diameters of 0.00085 and 0.00093 inch can be achieved by making the filaments with this diameter, or may be achieved by etching filaments having a slightly larger diameter (e.g., 0.001 inch) until the desired diameters are reached. In the particular embodiment, the cover 302 has a maximum diameter 314 (in the expanded state) of between about 4 mm and about 8 mm, or between about 5 mm and about 7 mm, or about 6 mm. The tubular mesh 322 has a diameter (in the expanded state) of between about 2 mm and 3 mm, or about 2.5 mm. In some embodiments some or all of the filaments may comprise drawn filled tubes (DFT) having a radiopaque cross-sectional fill area ratio of between about 10% to about 70%, or between about 51% to about 70%. The fill material can be platinum, or gold, or tantalum, or an alloy of any of these. The particular embodiment described has excellent compression in to a small diameter for delivery through a small catheter lumen, and has safe characteristics when expanded and delivered into an aneurysm.

Figure 36:
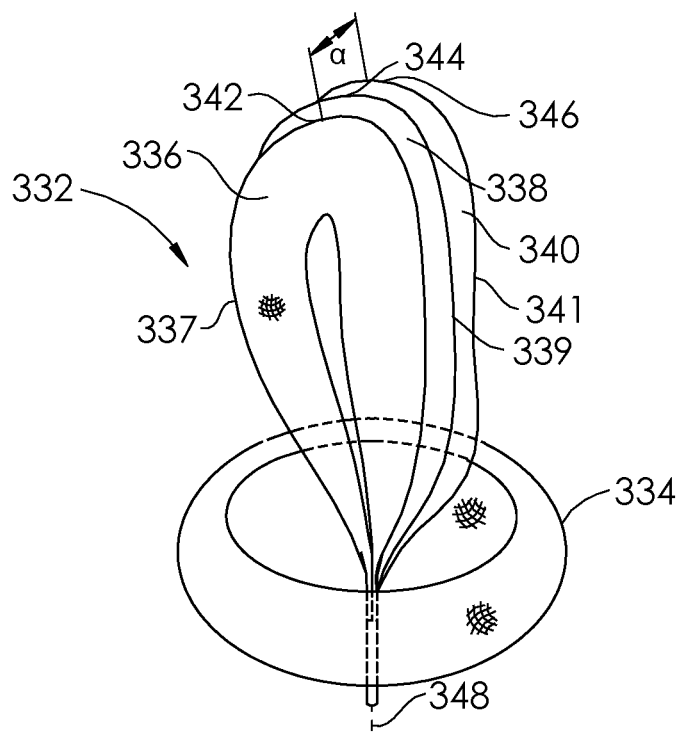
FIG. 36 is a perspective view of an occlusion device according to an alternative embodiment of the present disclosure.

FIG. 36 illustrates an occlusion device 332 comprising a cover 334 similar to the cover 302 of the occlusion device 300 of FIG. 35. However, there are three doubled-over or looped tubular meshes 336, 338, 340, each having a smooth apex 342, 344, 346, respectively. The three doubled-over or looped tubular meshes 336, 338, 340 are arrayed next to each other like books on a bookshelf. Because the diameter of their intermediate portions 337, 339, 341, in the expanded configuration, are greater than the diameter of their ends, the three doubled-over or looped tubular meshes 336, 338, 340 are fanned out. In some embodiments, the three doubled-over or looped tubular meshes 336, 338, 340 together form a fanned angle α that is between about 15° and about 90°, or between about 20° and about 75°, or between about 30° and about 60°. In alternative embodiments, the three doubled-over or looped tubular meshes 336, 338, 340 inhabit three substantially parallel planes that are not coplanar to each other, and are thus the three doubled-over or looped tubular meshes 336, 338, 340 are linearly arrayed in a transverse dimension to the longitudinal axis 348 of the cover 334.

Figure 37:
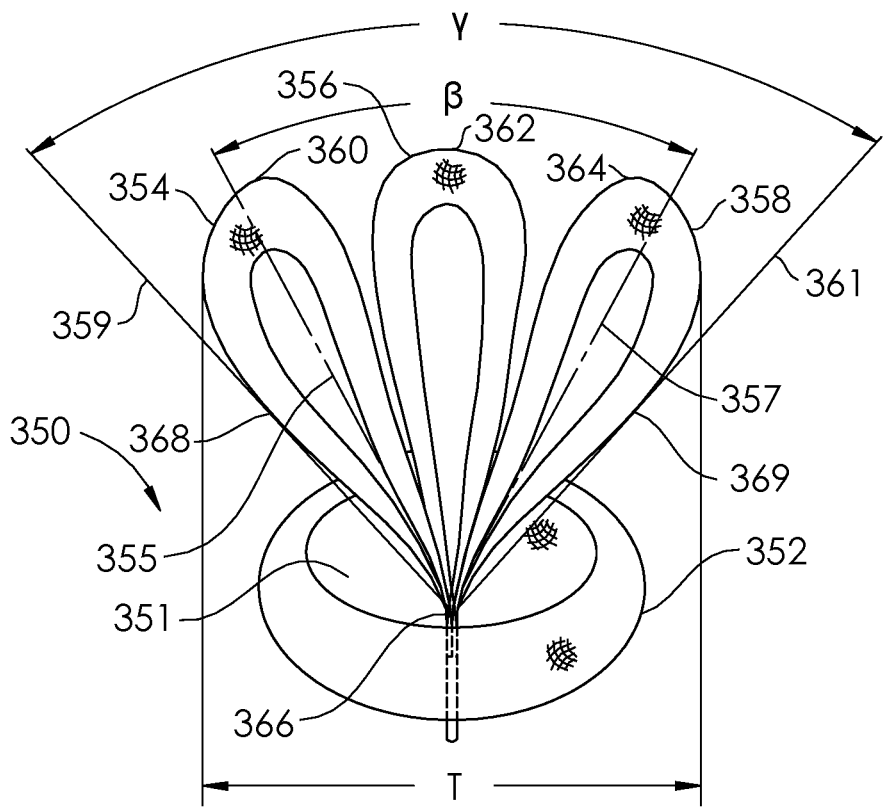
FIG. 37 is a perspective view of an occlusion device according to an alternative embodiment of the present disclosure.

FIG. 37 illustrates an occlusion device 350 comprising a cover 352 having a concavity 351, the cover 352 similar to the cover 302 of the occlusion device 300 of FIG. 35. However, there are three doubled-over or looped tubular meshes 354, 356, 358, each having a smooth apex 360, 362, 364, respectively. The three doubled-over or looped tubular meshes 354, 356, 358 are arrayed next to each other like ribs of an opened folding hand fan. In some embodiments, all three of the looped tubular meshes 354, 356, 358 together approximate a single plane. In other embodiments, the looped tubular meshes 354, 356, 358 each approximate a different plane, together approximating an open triptych. In some embodiments, looped tubular meshes 354, 356, 358 together form a fanned angle β, between the centerline 355 of the first outside tubular mesh 354 and the centerline 357 of the second outside tubular mesh 358, that is between about 15° and about 120°, or between about 20° and about 90°, or between about 25° and about 75°, or between about 30° and about 60°. In some embodiments, looped tubular meshes 354, 356, 358 together form a fanned angle γ, between the general outer contour line 359 of the first outside tubular mesh 354 and the general outer contour line 361 of the second outside tubular mesh 358, that is between about 20° and about 150°, or between about 30° and about 120°, or between about 30° and about 90°. The outer contour lines 359, 361 extend between the attachment 366 of the first and second ends of the tubular mesh and a maximal lateral extension point 368, 369. a maximum transverse dimension T is formed by the three looped tubular meshes 354, 356, 358, and is configured to contact the inner surface of an aneurysm at both sides, to stabilize the occlusion device 350 within the aneurysm. The cover 352 is configured to seal or occlude the aneurysm adjacent the neck, as in the other covers presented herein.

Figure 38:
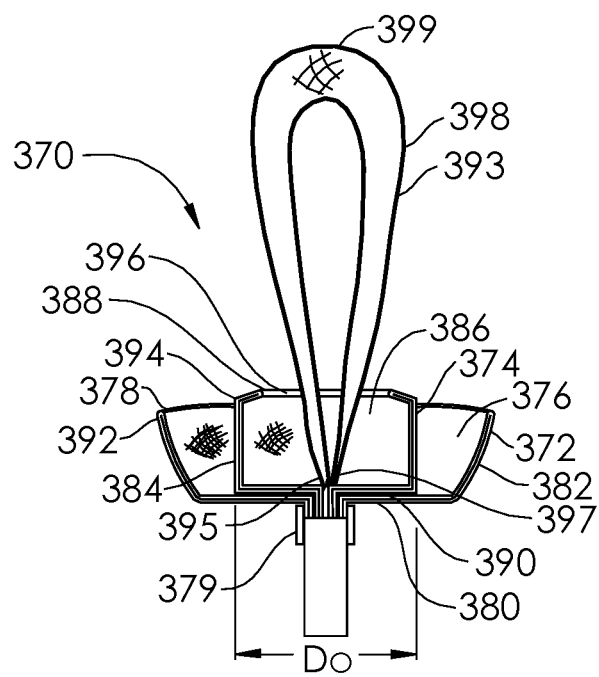
FIG. 38 is a longitudinal sectional view of an occlusion device according to an alternative embodiment of the present disclosure.

FIG. 38 illustrates an occlusion device 370 comprising an outer cover 372 and an inner cover 374. The outer cover 372 includes a concavity 376 facing toward the distal end 378 of outer cover 372 and away from the proximal end 380 of the outer cover 372. The inner cover 374 is disposed within the concavity 376 of the outer cover 372 and includes a concavity 386 facing toward the distal end 388 of inner cover 374 and away from the proximal end 390 of the outer cover 374. The outer cover 372 has a distal flare 392, and the inner cover 374 has a maximum diameter 394 and a reduced diameter distal orifice 396. The covers 372, 374 are each fabricated as inverted mesh tubes 382, 384 having a simple straight elongate configuration, and subsequently formed into the shapes shown in FIG. 38, and heat set into these shapes, as described previously herein. Either of the covers 372, 374 may have the material or dimensional characteristic of any other of the covers described herein. An overlap dimension Do has an increased braid density, because it is substantially the braid densities (e.g., picks per inch) of the two covers 372, 374 combined. Thus, substantial stagnation of blood flow can be achieved at the neck of the aneurysm to thrombose and occlude the aneurysm. Extending from the concavity 386 is a doubled-over or looped tubular mesh 398 having a smooth apex 399 configured to safely contact an interior wall of an aneurysm. The tubular mesh 398 has a first end 397 and a second end 395, and an intermediate portion 393 extending between the first end 397 and second end 395. The outer cover 372, the inner cover 374, and the tubular mesh 398 may each have differing characteristics from each other in order to optimize the performance characteristics of each. In one embodiment, the inner cover 374 has a first braid density and the outer cover 372 has a second braid density that is greater than the first braid density. The tubular mesh 398 has a third braid density that is less than the first braid density. In some embodiments, the second braid density is between 110% and 200% of the first braid density. In some embodiments, the first braid density is between 110% and 200% of the third braid density. In certain embodiments, the outer cover 372 may comprise between 24 and 48 filaments, the inner cover 374 may comprise between 12 and 36 filaments, and the tubular mesh 398 may comprise between 6 and 24 filaments. Each filament may have a diameter between about 0.0006 to about 0.0015 inch, or between about 0.00075 to about 0.00125 inch. In a particular embodiment, the outer cover 372 may comprise 36 filaments, the inner cover 374 may comprise 24 filaments, and the tubular mesh 398 may comprise 12 filaments. The filaments may comprise nickel-titanium alloy, or DFT wires, or a combination thereof. The inner cover 374 additionally can serve to stabilize the tubular mesh 398, such that its loop remains substantially upright. The outer cover 372, at its distal flare 392 is configured to grip the inner wall of an aneurysm. As in all of the occlusion devices, a marker band 379 may be carried at an end of the occlusion device 370 and be configured to hold the ends 395, 397 and to be a radiopaque indicator of the proximal end of the occlusion device 370 on x-ray or fluoroscopy.

In any of the embodiments presented herein, the doubled-over or looped tubular mesh may be configured to engage a portion of the interior wall of the aneurysm, up to an including the majority of the wall of the entire aneurysm sac. In any of the embodiments presented herein that include a cover, the cover may be configured to engage with an interior wall of the aneurysm at or adjacent the neck of the aneurysm. The engagement may include a radial force. In some embodiments, the cover may be configured to cover the neck of the aneurysm without significantly engaging the aneurysm wall with a radial force.

Figure 39:
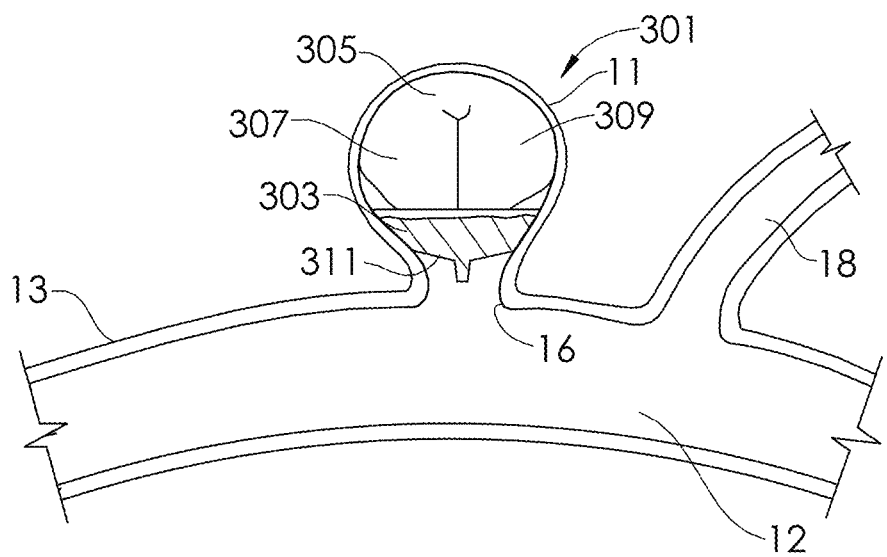
FIG. 39 is a view of an occlusion device implanted within an aneurysm according to an embodiment of the present disclosure.

Additional materials may be carried on a proximal portion of the cover, or any part of the occlusion device that is adjacent the neck of the aneurysm, in order to facilitate healing of the neck of the aneurysm. FIG. 39 illustrates an occlusion device 301 comprising a cover 303 that is coupled to a doubled-over or looped tubular mesh 305 having a first leg 307 and a second leg 309. The cover 303 includes a biological layer 311 configured to encourage growth. In some embodiments, the biological layer 311 may comprise antibodies, in order to accelerate the formation of an endothelial layer, for example, by attracting endothelial progenitor cells (EPCs). In some embodiments, the biological layer 311 may comprise a natural membrane or structure, such as a membrane, such as a membrane from an ear, or a cornea, or an ultra-thin piece of ligament, or even a piece of blood vessel wall.

Figure 40:
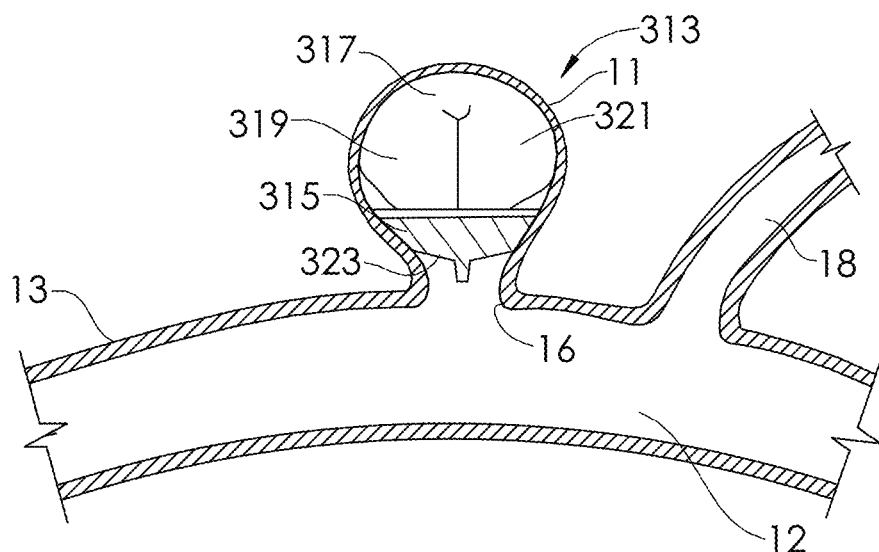
FIG. 40 is a view of an occlusion device implanted within an aneurysm according to an embodiment of the present disclosure.

FIG. 40 illustrates an occlusion device 313 comprising a cover 315 that is coupled to a doubled-over or looped tubular mesh 317 having a first leg 319 and a second leg 321. The cover 315 includes a polymer layer 323 configured to act as a simulated arterial wall. In some embodiments, the polymer layer 323 may comprise polytetrafluoroethylene, such as expanded polytetrafluoroethylene (ePTFE), such as that used in grafts.

The following clauses include examples of apparatus of the disclosure.

Clause 1: In one example, an apparatus for treating an aneurysm in a blood vessel includes an occlusion element configured to be releasably coupled to an elongate delivery shaft, the occlusion element including a cover including a mesh material and configured to be delivered in a collapsed configuration through an inner lumen of a delivery catheter, the inner lumen having a proximal end and a distal end, the cover further configured to expand to an expanded configuration when advanced out of the distal end of the inner lumen of the delivery catheter and into the aneurysm, wherein the cover includes a diameter that is greater than the diameter or maximum transverse dimension of a neck portion of the aneurysm, and wherein the cover includes a distal concavity configured to face away from the neck portion of the aneurysm, and a first tubular mesh having a first end, a second end, a wall and a lumen, the first end and the second end of the first tubular mesh coupled to a central portion of the cover such that an intermediate portion of the first tubular mesh between the first end and the second end includes a substantially 180 degree turn, the intermediate portion of the first tubular mesh extending from the distal concavity of the cover, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm.

Clause 2: In some examples, the apparatus includes clause 1, wherein the occlusion element is configured such that the intermediate portion of the first tubular mesh is the first portion delivered out of the distal end of the inner lumen of the delivery catheter.

Clause 3: In some examples, the apparatus includes clause 2, wherein the intermediate portion of the first tubular mesh, when in its expanded configuration, includes a first leg and a second leg, the first leg configured to contact the second leg.

Clause 4: In some examples, the apparatus includes any one of clauses 1-3, wherein the cover is formed from a tube having a cover lumen, and wherein the first end and second end of the first tubular mesh are configured to be inserted into the cover lumen.

Clause 5: In some examples, the apparatus includes clause 4, wherein the first end and the second end of the first tubular mesh are configured to be secured next to each other in a collapsed state within the cover lumen.

Clause 6: In some examples, the apparatus includes clause 4, further including a cut in the wall of the first tubular mesh at the first end, wherein the second end, in a collapsed state is held within the first end, and wherein the first end and second end are secured within the cover lumen.

Clause 7: In some examples, the apparatus includes either one of clauses 5 or 6, wherein the first end and the second end of the first tubular mesh are secured within the cover lumen at a location proximal to the distal concavity of the cover.

Clause 8: In some examples, the apparatus includes clause 7, further including a pusher having a proximal end and a distal end, wherein the occlusion element is configured to be releasably coupled to the distal end of the pusher at a releasable joint.

Clause 9: In some examples, the apparatus includes clause 8, wherein the releasable joint is located within the cover lumen adjacent to the location proximal to the distal concavity of the cover.

Clause 10: In some examples, the apparatus includes any one of clauses 1-3, wherein the intermediate portion of the first tubular mesh, when in its expanded configuration, has a maximum transverse dimension that is greater than the diameter of the cover.

Clause 11: In some examples, the apparatus includes any one of clauses 1-10, wherein the cover is circular.

Clause 12: In some examples, the apparatus includes any one of clauses 1-10, wherein the cover is elliptical or oval, and wherein the cover has a minor diameter or minimum transverse dimension that is greater than the diameter or maximum transverse dimension of the neck portion of the aneurysm.

Clause 13: In some examples, the apparatus includes any one of clauses 1-12, wherein the cover includes two layers of mesh.

Clause 14: In some examples, the apparatus includes clause 13, wherein the cover is constructed from an inverted mesh tube.

Clause 15: In some examples, the apparatus includes any one of clauses 1-14, wherein the cover includes a nickel-titanium alloy.

Clause 16: In some examples, the apparatus includes any one of clauses 1-15, wherein the first tubular mesh includes a nickel-titanium alloy.

Clause 17: In some examples, the apparatus includes any one of clauses 1-16, wherein the occlusion element includes a radiopaque material.

Clause 18: In some examples, the apparatus includes any one of clauses 1-17, wherein the radiopaque material includes a marker band.

Clause 19: In some examples, the apparatus includes any one of clauses 1-18, wherein the marker band is coupled to the first end and second end of the first tubular mesh.

Clause 20: In some examples, the apparatus includes either one of clauses 18 or 19, wherein the marker band is coupled to the proximal end of the cover.

Clause 21: In some examples, the apparatus includes either one of clauses 1 or 2, wherein the occlusion element further includes a second tubular mesh having a first end, a second end, a wall and a lumen, the first end and the second end of the second tubular mesh coupled to a central portion of the cover such that an intermediate portion of the second tubular mesh between the first end and the second end includes a substantially 180 degree turn, the intermediate portion of the second tubular mesh extending from the distal concavity of the cover, wherein the intermediate portion of the second tubular mesh has a collapsed configuration configured to be delivered through the inner lumen of the delivery catheter, and wherein the intermediate portion of the second tubular mesh is configured to expand to an expanded configuration when advanced out of the distal end of the inner lumen of the delivery catheter an into the aneurysm.

Clause 22: In some examples, the apparatus includes clause 21, wherein the intermediate portion of the first tubular mesh, when in its expanded configuration, includes a first leg and a second leg, and wherein the second tubular mesh passes between the first leg and the second leg of the first tubular mesh.

Clause 23: In some examples, the apparatus includes clause 22, wherein the substantially 180 degree turn of the first tubular mesh generally defines a first plane and wherein the substantially 180 degree turn of the second tubular mesh generally defines a second plane, the second plane non-parallel to the first plane.

Clause 24: In some examples, the apparatus includes clause 23, wherein the second plane is generally perpendicular to the first plane.

Clause 25: In another example, an apparatus for treating an aneurysm in a blood vessel, includes an occlusion element configured to be releasably coupled to an elongate delivery shaft, the occlusion element including a cover including a mesh material and configured to be delivered in a collapsed configuration through an inner lumen of a delivery catheter, the inner lumen having a proximal end and a distal end, the cover further configured to expand to an expanded configuration when advanced out of the distal end of the inner lumen of the delivery catheter and into the aneurysm, wherein the cover includes a diameter that is greater than the diameter or maximum transverse dimension of a neck portion of the aneurysm, a first tubular mesh having a first end, a second end, a wall and a lumen, the first end and the second end of the first tubular mesh coupled to a central portion of the cover such that an intermediate portion of the first tubular mesh between the first end and the second end includes a substantially 180 degree turn, the intermediate portion of the first tubular mesh extending from the distal concavity of the cover, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm, and a second tubular mesh having a first end, a second end, a wall and a lumen, the first end and the second end of the second tubular mesh coupled to a central portion of the cover such that an intermediate portion of the second tubular mesh between the first end and the second end includes a substantially 180 degree turn, the intermediate portion of the second tubular mesh extending from the distal concavity of the cover, wherein the intermediate portion of the second tubular mesh has a collapsed configuration configured to be delivered through the inner lumen of the delivery catheter, and wherein the intermediate portion of the second tubular mesh is configured to expand to an expanded configuration when advanced out of the distal end of the inner lumen of the delivery catheter an into the aneurysm.

Clause 26: In some examples, the apparatus includes clause 25, wherein the intermediate portion of the first tubular mesh, when in its expanded configuration, includes a first leg and a second leg, wherein the second tubular mesh passes between the first leg and the second leg of the first tubular mesh.

Clause 27: In some examples, the apparatus includes clause 25, wherein the wall of the first tubular mesh has a first opening and a second opening, wherein the second tubular mesh passes into the first opening and out of the second opening.

Clause 28: In some examples, the apparatus includes any one of clauses 25-27, wherein the cover includes an aperture in the mesh material and wherein the first tubular mesh and the second tubular mesh pass through the aperture.

Clause 29: In another example, an apparatus for treating an aneurysm in a blood vessel, includes an occlusion element configured to be releasably coupled to an elongate delivery shaft, the occlusion element including a cover including a mesh material and configured to be delivered in a collapsed configuration through an inner lumen of a delivery catheter, the inner lumen having a proximal end and a distal end, the cover further configured to expand to an expanded configuration when advanced out of the distal end of the inner lumen of the delivery catheter and into the aneurysm, wherein the cover in its expanded configuration has a transverse dimension that is greater than a maximum transverse dimension of a neck portion of the aneurysm, and a first tubular mesh having a first end, a second end, a wall and a lumen, the first end and the second end of the first tubular mesh coupled to a central portion of the cover such that an intermediate portion of the first tubular mesh between the first end and the second end includes a substantially 180 degree turn, the intermediate portion of the first tubular mesh extending distally from the central portion of the cover, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm.

Clause 30. In some examples, the apparatus includes clause 29, wherein the occlusion element is configured such that the intermediate portion of the first tubular mesh is configured to begin to exit the distal end of the inner lumen of the delivery catheter before the cover.

Clause 31: In some examples, the apparatus includes clause 30, wherein the intermediate portion of the first tubular mesh, in its expanded configuration, includes a first leg and a second leg, the first leg configured to contact the second leg.

Clause 32: In some examples, the apparatus includes clause 29, wherein the cover is formed from a tube having a cover lumen, and wherein the first end and second end of the first tubular mesh are configured to be inserted into the cover lumen.

Clause 33: In some examples, the apparatus includes clause 32, wherein the first end and the second end of the first tubular mesh are configured to be secured next to each other in a collapsed state within the cover lumen.

Clause 34: In some examples, the apparatus includes clause 33, wherein the cover includes a distal concavity configured to face away from the neck portion of the aneurysm.

Clause 35: In some examples, the apparatus includes clause 34, wherein the first end and the second end of the first tubular mesh are secured within the cover lumen at a location proximal to the distal concavity of the cover.

Clause 36: In some examples, the apparatus includes clause 32, further including an at least partially longitudinally extending cut in the wall of the first tubular mesh at the first end, wherein the second end, in a collapsed state, is surrounded by the first end, and wherein the first end and second end are secured within the cover lumen.

Clause 37: In some examples, the apparatus includes clause 29, further including a pusher having a proximal end and a distal end, wherein the occlusion element is releasably coupled to the distal end of the pusher at a releasable joint.

Clause 38: In some examples, the apparatus includes clause 29, wherein the intermediate portion of the first tubular mesh, in its expanded configuration, has a maximum transverse dimension that is greater than a maximum transverse dimension of the cover.

Clause 39: In some examples, the apparatus includes clause 29, wherein the cover includes two layers of mesh.

Clause 40: In some examples, the apparatus includes clause 39, wherein the cover is constructed from an inverted mesh tube.

Clause 41: In some examples, the apparatus includes clause 29, wherein the occlusion element further includes a second tubular mesh having a first end, a second end, a wall and a lumen, the first end and the second end of the second tubular mesh coupled to a central portion of the cover such that an intermediate portion of the second tubular mesh between the first end and the second end includes a substantially 180 degree turn, the intermediate portion of the second tubular mesh extending from the central portion of the cover, wherein the intermediate portion of the second tubular mesh has a collapsed configuration configured to be delivered through the inner lumen of the delivery catheter, and wherein the intermediate portion of the second tubular mesh is configured to expand to an expanded configuration when advanced out of the distal end of the inner lumen of the delivery catheter an into the aneurysm.

Clause 42: In some examples, the apparatus includes clause 41, wherein the intermediate portion of the first tubular mesh, when in its expanded configuration, includes a first leg and a second leg, and wherein the second tubular mesh passes between the first leg and the second leg of the first tubular mesh.

Clause 43: In some examples, the apparatus includes clause 42, wherein the substantially 180 degree turn of the first tubular mesh generally defines a first plane and wherein the substantially 180 degree turn of the second tubular mesh generally defines a second plane, the second plane non-parallel to the first plane.

Clause 44: In some examples, the apparatus includes clause 43, wherein the second plane is generally perpendicular to the first plane.

Clause 45: In some examples, the apparatus includes clause 41, wherein the wall of the first tubular mesh has a first opening and a second opening, wherein the second tubular mesh passes into the first opening and out of the second opening.

Clause 46: In some examples, the apparatus includes clause 45, wherein the first opening includes a first cut in the wall of the first tubular mesh and wherein the second opening includes a second cut in the wall of the tubular mesh.

Clause 47: In some examples, the apparatus includes clause 41, wherein the intermediate portion of the first tubular mesh, in its expanded configuration, has a maximum transverse dimension and the intermediate portion of the second tubular mesh, in its expanded configuration has a maximum transverse dimension, the maximum transverse dimension of the intermediate portion of the first tubular member greater than the maximum transverse dimension of the intermediate portion of the second tubular member.

Clause 48: In some examples, the apparatus includes clause 47, wherein the maximum transverse dimension of the intermediate portion of the first tubular mesh and the maximum transverse dimension of the intermediate portion of the second tubular mesh are each different from a maximum transverse dimension of the cover.

Clause 49: In some examples, the apparatus includes clause 41, wherein the cover includes an aperture in the mesh material at a distal end of the cover, and wherein the intermediate portion of the first tubular mesh and the intermediate portion of the second tubular mesh pass through the aperture.

Clause 50: In some examples, the apparatus includes clause 41, wherein the intermediate portion of the first tubular mesh, when in its expanded configuration, includes a first leg and a second leg, and wherein the second tubular mesh, when in its expanded configuration, includes a first leg and a second leg, the first leg of the first tubular mesh adjacent to and on a first side of the first leg of the second tubular mesh, and the second leg of the first tubular mesh adjacent to and on the first side of the second leg of the second tubular mesh.

Clause 51: In some examples, the apparatus includes clause 29 wherein the cover includes an aperture in the mesh material and wherein the intermediate portion of the first tubular mesh passes through the aperture.

Clause 52: In some examples, the apparatus includes clause 29, wherein the cover has a circular outer shape.

Clause 53: In some examples, the apparatus includes clause 29, wherein the cover has a longitudinal section having a substantially trapezoidal shape.

Clause 54: In some examples, the apparatus includes clause 29, wherein at least the mesh of the cover includes drawn filled tubes having a radiopaque core and a nickel-titanium alloy.

Clause 55: In some examples, the apparatus includes clause 54, wherein the radiopaque core of each of at least some of the drawn filled tubes has a cross-sectional area that is between about 51% and about 70% of the total cross-sectional area of the each of at least some of the drawn filled tubes.

Clause 56: In some examples, the apparatus includes clause 29, wherein the mesh of the cover is woven from filaments, and wherein between about 50 percent and about 100 percent of the filaments include drawn filled tubes.

Clause 57: In another example, an apparatus for treating an aneurysm in a blood vessel, includes an occlusion element configured to be releasably coupled to an elongate delivery shaft, the occlusion element including a first tubular mesh having a first end, a second end, a wall and a lumen, the first end and the second end of the first tubular mesh coupled together at a proximal end of the occlusion element such that an intermediate portion of the first tubular mesh between the first end and the second end includes a substantially 180 degree turn, the intermediate portion of the first tubular mesh extending distally from the proximal end of the occlusion element, wherein the intermediate portion of the first tubular mesh has a collapsed configuration configured to be delivered through the inner lumen of the delivery catheter, and wherein the intermediate portion of the first tubular mesh is configured to expand to an expanded configuration when advanced out of the distal end of the inner lumen of the delivery catheter an into the aneurysm.

Clause 58: In some examples, the apparatus includes clause 57, wherein the occlusion element further includes a second tubular mesh having a first end, a second end, a wall and a lumen, the first end and the second end of the second tubular mesh coupled to the proximal end of the occlusion element such that an intermediate portion of the second tubular mesh between the first end and the second end includes a substantially 180 degree turn, the intermediate portion of the second tubular mesh extending distally from the proximal end of the occlusion element, wherein the intermediate portion of the second tubular mesh has a collapsed configuration configured to be delivered through the inner lumen of the delivery catheter, and wherein the intermediate portion of the second tubular mesh is configured to expand to an expanded configuration when advanced out of the distal end of the inner lumen of the delivery catheter an into the aneurysm.

Figure 41:
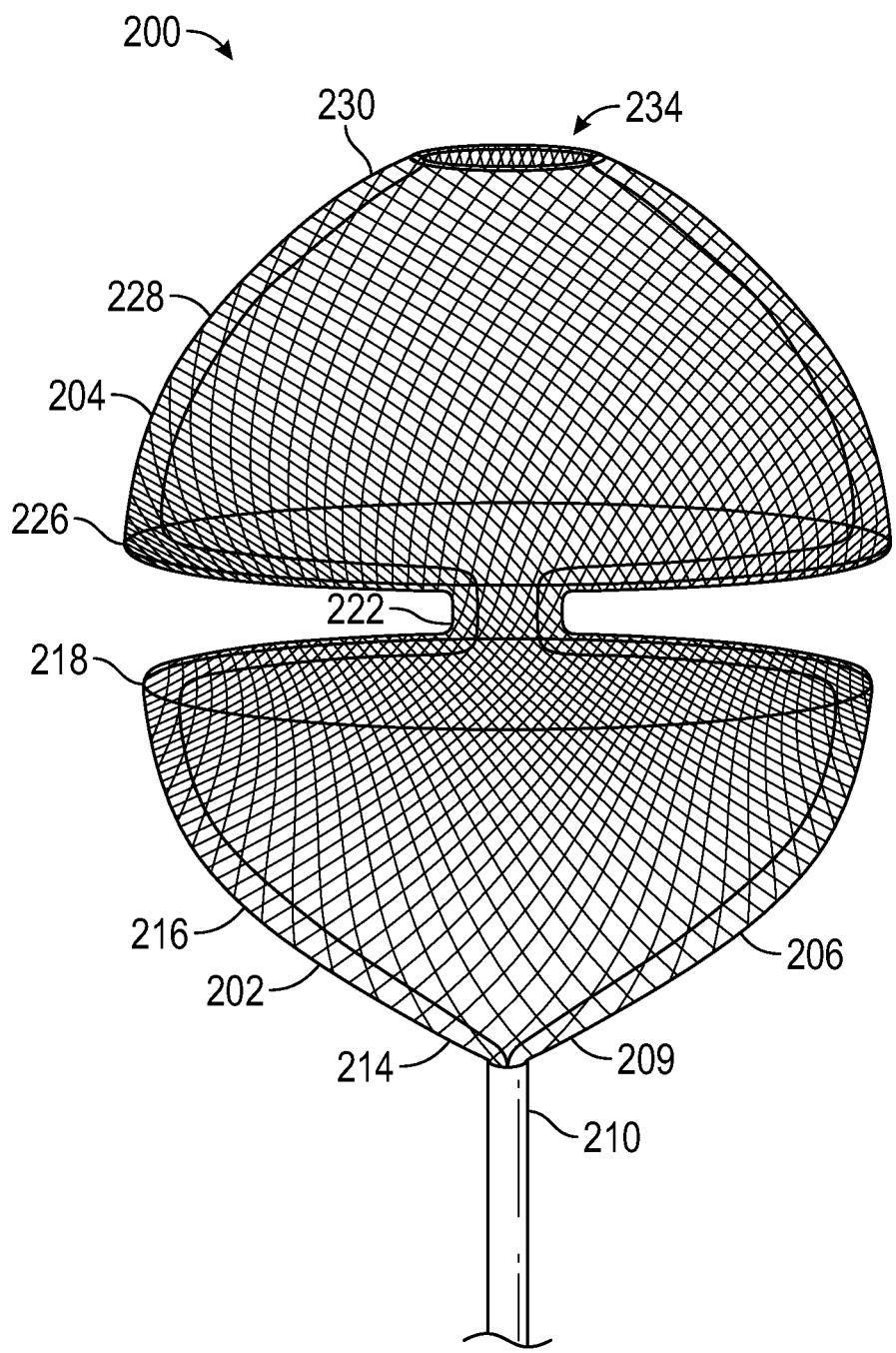
FIG. 41 is a perspective view of an occlusion device according to an embodiment of the present disclosure.
Figure 42:
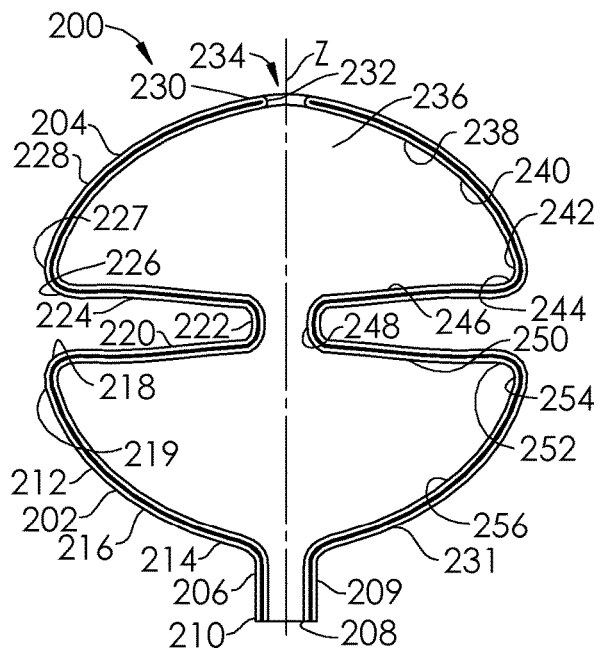
FIG. 42 is a sectional view of the occlusion device of FIG. 41.

FIG. 41 illustrates an occlusion device 200 configured for placement within an aneurysm. The occlusion device 200 comprises a proximal section 202 and a distal section 204, each constructed of a single, continuous dual layer mesh. Turning to FIG. 42, the occlusion device 200 is constructed from an inverted mesh tube 206 having a first end 208, a second end 210, and a wall 209. The inverted mesh tube 206 extends on an outer layer 212 from the second end 210 past a proximal end 214 of the proximal section 202 and along a proximal hemisphere shape 216 to a maximum diameter portion 218 having an acute angulation 219. From the maximum diameter portion 218, the outer layer 212 extends radially inward along a substantially flattened portion 220 to a central waist 222. The outer layer 212 then extends radially outward along a substantially flattened portion 224 of the distal section 204 to a maximum diameter portion 226 having an acute angulation 227 to a distal hemisphere shape 228 to a distal end 230 of the occlusion device 200. The hemisphere shape 228 is configured to contact at least a portion of an aneurysm dome. The maximum diameter portion 226 has a diameter that is about equal to the diameter of the maximum diameter portion 218, but in other embodiments, they may differ. The occlusion device 200 is substantially cylindrically symmetric around a central axis Z. However, in alternative embodiments, there may be certain portions of asymmetry, such as one or more indented or extended feature at a particular location in a perimeter. At the distal end 230, the wall 209 is inverted inwardly at an inversion fold 232, which creates a distal orifice 234 and an internal volume 236. The wall 209 transitions at the inversion fold 232 from the outer layer 212 to an inner layer 238 which follows the contours of the outer layer 212 from the distal orifice 234 to the first end 208. The inner layer 238 follows a hemisphere shape 240, a maximum diameter portion 242 having an acute angulation 244, a substantially flattened portion 246 of the distal section 204, a central waist 248, a substantially flattened portion 250 of the proximal section 202, a maximum diameter portion 252 having an acute angulation 254, and a hemisphere shape 256. The occlusion device 200 is fabricated as an inverted mesh tube 206 having a simple straight elongate configuration, and is subsequently formed into the shape shown in FIGS. 41 and 42 and heat set into this shape. For example, the occlusion device 200 may be constructed as a single layer mesh tube formed of at least some nickel-titanium alloy filaments, and then inverted on itself. The inverted mesh tube 206 may then be placed into a die or mold comprising one or more pieces, to hold it in the shape of the occlusion device 200. Then, the occlusion device 200 may be subjected to an elevated temperature and then cooled, to lock in the shape, resulting in an occlusion device 200 having at least some superelastic properties. Each of the proximal section 202 and distal section 204 are configured to be compressed or compacted within the lumen 148 of a delivery catheter 150 (e.g., microcatheter).

In some embodiments, one or both of the proximal section 202 or the distal section 204 may comprise some nickel-titanium alloy filaments and some radiopaque elements, comprising platinum, gold, tantalum, or alloys of any of these or other radiopaque materials. In some embodiments, the filaments may comprise drawn filled tubes, such as those comprising a nickel-titanium alloy outer wall and a platinum core. The radiopaque material allows the occlusion device 200 to be visible on radiographs or fluoroscopy. The occlusion device 200 may be configured by controlling how much radiopaque material is used, by either the ratio of radiopaque filaments to non-radiopaque filaments, or by the amount of platinum core in the drawn filled tubes. In this manner, the occlusion device 200 can be selectively fabricated to be sufficiently visible, but not over visible, e.g., overly bright, such that other objects are obscured. In some embodiments, whether any of the filaments comprise radiopaque materials or not, a marker band may be attached to the proximal end 214 of the proximal section 202, by adhesive or epoxy bonding, or swaging, welding or other mechanical attachment.

Figure 43:
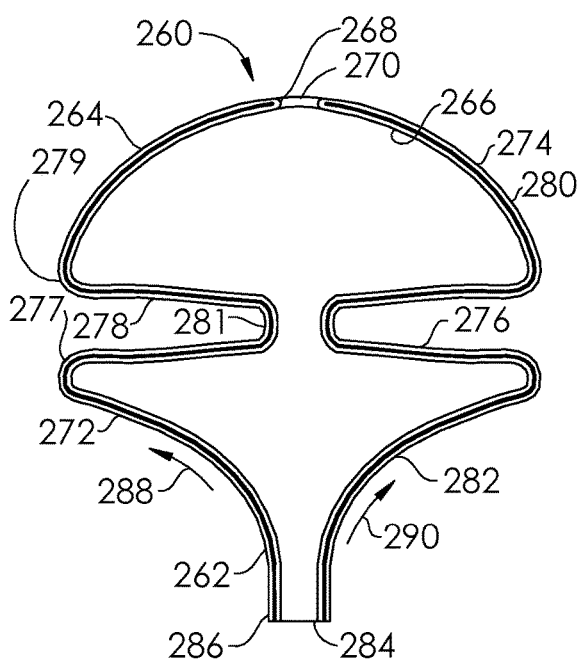
FIG. 43 is a sectional view of an alternative occlusion device, according to an embodiment of the present disclosure.

FIG. 43 illustrates an occlusion device 260 also comprising an inverted mesh tube 262 and having an outer layer 264, an inner layer 266, and an inversion fold 268, which creates a distal orifice 270, and serves as the transition between the outer layer 264 and the inner layer 266. The inverted mesh tube 262 has a first end 284 and a second end 286. The occlusion device 260 includes a proximal section 272 and a distal section 274. The proximal section 272 and distal section 274 have substantially flattened portions 276, 278, and the distal section 274 has a distal hemisphere shape 280, configured to contact an aneurysm dome. There is a waist 281 between the substantially flattened portions 276, 278. The maximum diameter portion 279 has a diameter that is about equal to the diameter of the maximum diameter portion 277, but in other embodiments, they may differ. The proximal section 272 includes a concave cone shape 282, or circumferentially-extending concavity, which may be configured to direct blood flow, particularly when the occlusion device 260 is implanted within a bifurcation aneurysm or a terminal aneurysm, wherein the blood flow is directed along the paths of arrow 288 or arrow 290. The occlusion device 260 may comprise any of the materials and be made with any of the processes described in relation to the occlusion device 200.

Figure 44:
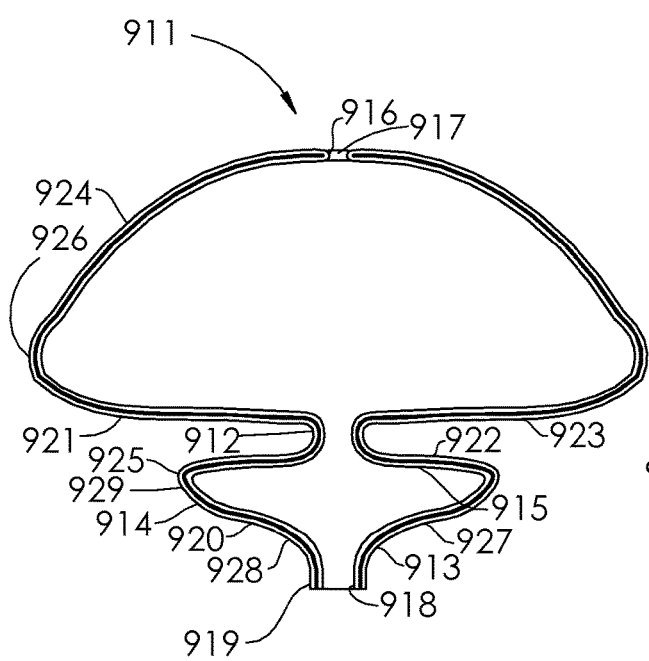
FIG. 44 is a sectional view of an alternative occlusion device, according to an embodiment of the present disclosure.

FIG. 44 illustrates an occlusion device 911 also comprising an inverted mesh tube 913 and having an outer layer 914, an inner layer 915, and an inversion fold 916, which creates a distal orifice 917, and serves as the transition between the outer layer 914 and the inner layer 915. The inverted mesh tube 913 has a first end 918 and a second end 919. The occlusion device 911 includes a proximal section 920 and a distal section 921. The proximal section 920 and distal section 921 have substantially flattened portions 922, 923, and the distal section 921 has a distal hemisphere shape 924, configured to contact an aneurysm dome. There is a waist 912 between the substantially flattened portions 922, 923. The maximum diameter portion 926, on the distal section 921, has a diameter that is larger than the diameter of the maximum diameter portion 925, on the proximal section 920, and thus, the occlusion device 911 is configured to be implanted in an aneurysm having a larger dome (distal) portion and a smaller proximal portion of the aneurysm sac. The proximal section 920 of the occlusion device 911 includes a partially convex, partially concave shape 927 which may be configured to direct blood flow along the concave portion 928, and also configured to interface with the proximal portion of the aneurysm at the convex portion 929. Both the concave portion 928 and the convex portion 929 face substantially proximally. The occlusion device 911 may comprise any of the materials and be made with any of the processes described in relation to the occlusion device 200.

Figure 45:
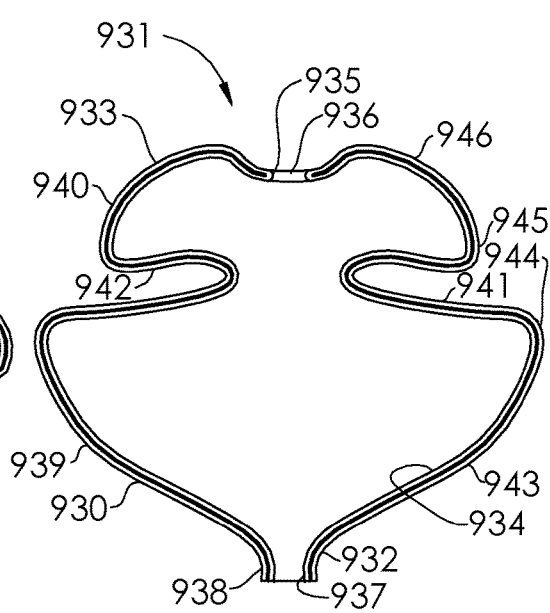
FIG. 45 is a sectional view of an alternative occlusion device, according to an embodiment of the present disclosure.

FIG. 45 illustrates an occlusion device 931 also comprising an inverted mesh tube 932 and having an outer layer 933, an inner layer 934, and an inversion fold 935, which creates a distal orifice 936, and serves as the transition between the outer layer 933 and the inner layer 934. The inverted mesh tube 932 has a first end 937 and a second end 938. The occlusion device 931 includes a proximal section 939 and a distal section 940. The proximal section 939 and distal section 940 have curvilinear portions 941, 942 facing each other, and the proximal section 939 has a hemisphere shape 943, configured to contact a proximal wall of the aneurysm. The maximum diameter portion 945 of the distal section 940 has a diameter that is smaller than the diameter of the maximum diameter portion 944 of the proximal section 939, and thus, the occlusion device 931 is configured to be implanted in an aneurysm having a smaller dome (distal) portion and a larger proximal portion of the aneurysm sac. The distal section 940 includes a smaller hemisphere shape 946. The occlusion device 931 may comprise any of the materials and be made with any of the processes described in relation to the occlusion device 200.

Figure 46:
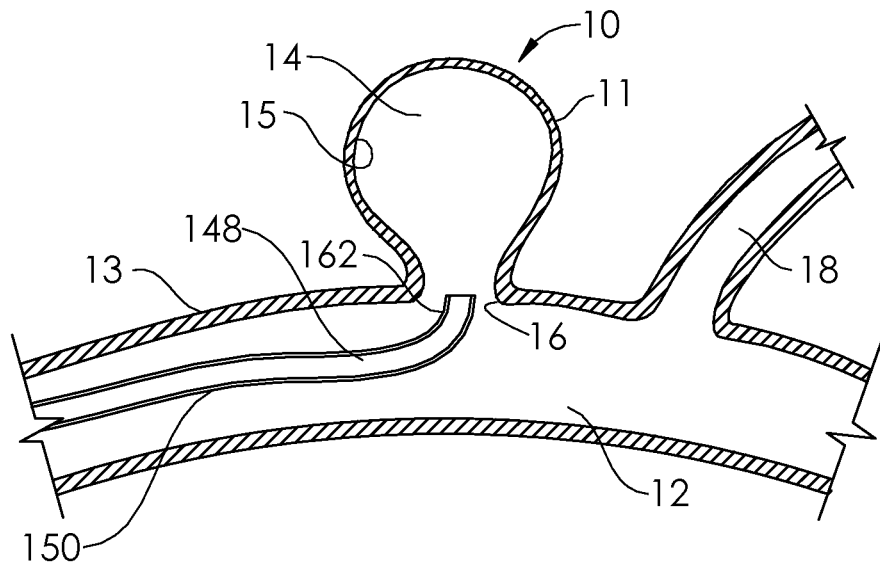
FIGS. 46-49 illustrate the implantation of the occlusion device of FIG. 41 in an aneurysm of a blood vessel of a patient.

In FIGS. 46-49, an aneurysm 10 having a neck portion 16 is shown. The occlusion device 200 is shown in use being implanted by a user (e.g., physician) into the aneurysm 10 through the delivery catheter 150 to disrupt or halt the flow of blood flow between the blood vessel 12 and the internal volume 14 of the aneurysm, thereby reducing the likelihood that the aneurysm 10 will rupture (or if previously ruptured, reducing the likelihood of rerupture). The occlusion device 200 is configured to be low profile device, minimizing disruptions to surrounding bodies, such as a side branch 18 of the blood vessel 12. The blood vessel 12 has a blood vessel wall 13 and the aneurysm 10 has an aneurysm wall 11. In FIG. 46, the delivery catheter 150 is advanced through a sheath and/or guiding catheter (not shown) through a puncture or cutdown in a peripheral blood vessel, such as a femoral artery, a brachial artery, or a radial artery. The distal end 162 of the delivery catheter 150 may be shaped with a curve, as shown, either by the manufacturer, or prior to the procedure by the user, in order to allow for improved backup support when delivering the occlusion device 200. The distal end 162 of the delivery catheter 150 is placed adjacent the neck portion 16 of the aneurysm 10. The delivery catheter 150 may be advanced over a guidewire (not shown) that is passed through the lumen 148. The guidewire may then be removed, leaving the lumen 148 as a delivery conduit and the delivery catheter 150 as a support column.

Figure 47:
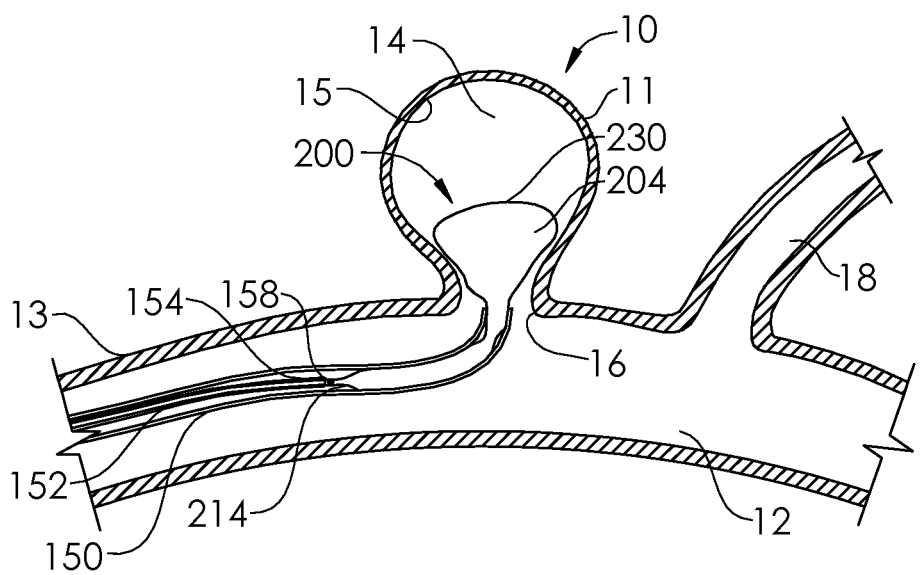
Figure 48:
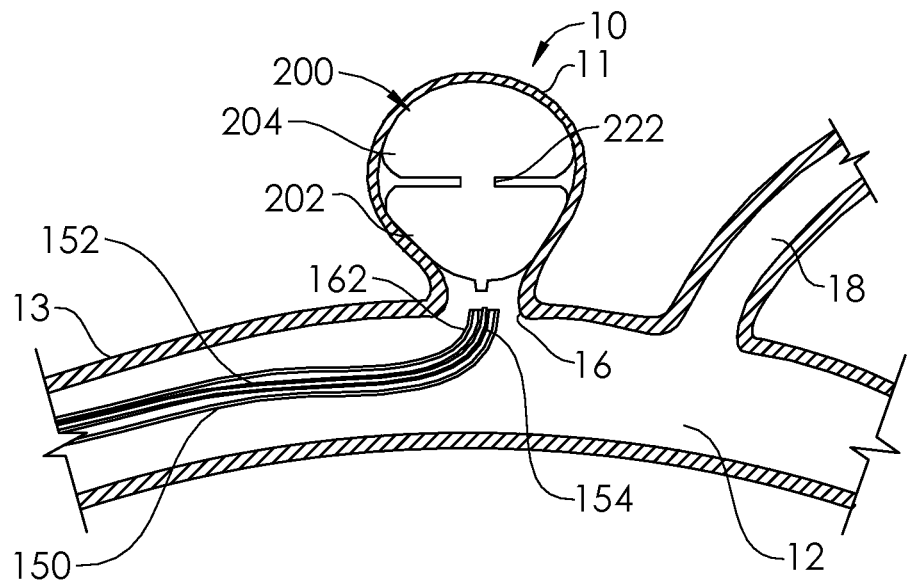

In FIG. 47, the occlusion device 200 is advanced through the lumen 148 of the delivery catheter 150, as described, and the distal section 204 of the occlusion device 200 is advanced out of the lumen 148 and into the internal volume 14 of the aneurysm 10. The distal end 230 is the first portion of the occlusion device 200 that exits the lumen 148 and thus is the first portion of the occlusion device to enter the aneurysm 10. The distal end 230 is blunt, soft, and atraumatic and is configured to first contact the interior surface 15 of the aneurysm 10. In FIG. 48, the occlusion device 200 is shown in a substantially expanded configuration within the internal volume 14 of the aneurysm 10. The proximal section 202 is expanded against the interior surface 15 of the aneurysm 10, and covers the neck portion 16 of the aneurysm. The distal section 204 is expanded against the interior surface 15 of the aneurysm 10, and serves to anchor or stabilize the proximal section 202 in the aneurysm 10 and adjacent the neck portion 16.

Figure 49:
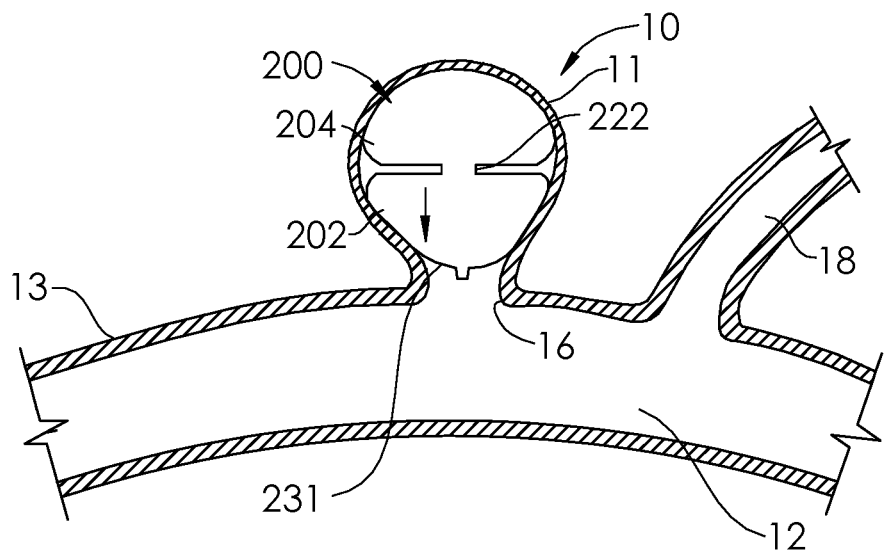
Figure 50:
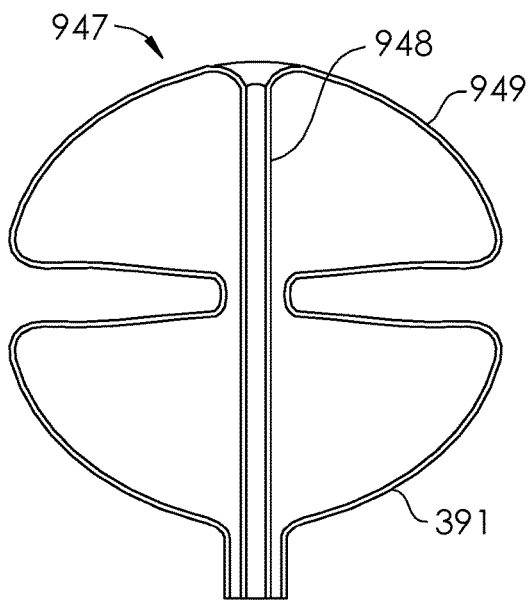
FIG. 50 is a sectional view of an alternative occlusion device, according to an embodiment of the present disclosure.
Figure 51:
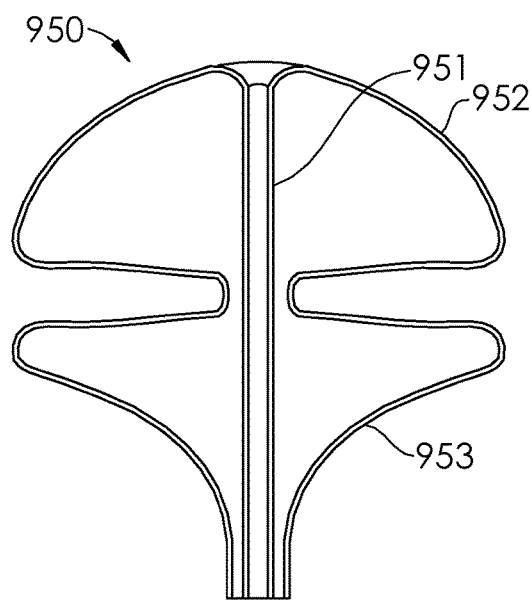
FIG. 51 is a sectional view of an alternative occlusion device, according to an embodiment of the present disclosure.
Figure 52:
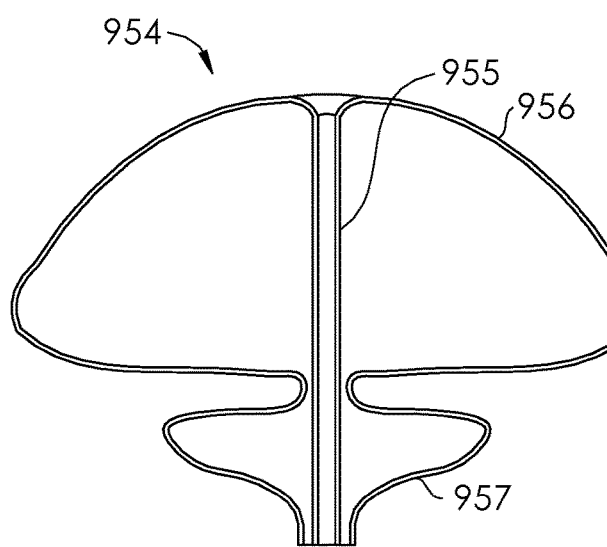
FIG. 52 is a sectional view of an alternative occlusion device, according to an embodiment of the present disclosure.
Figure 53:
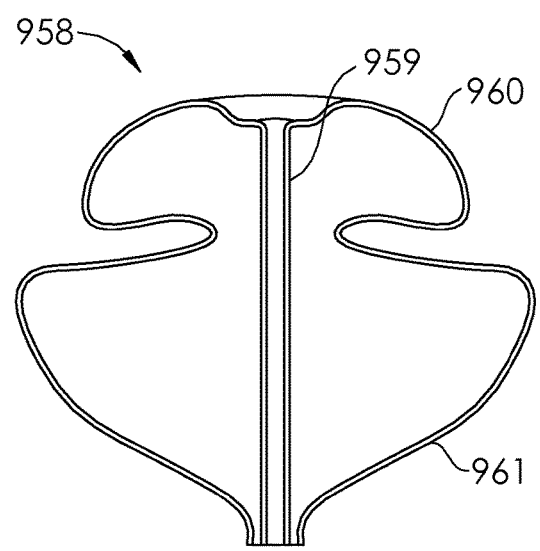
FIG. 53 is a sectional view of an alternative occlusion device, according to an embodiment of the present disclosure.

Also, in FIG. 48, the detachable joint 158 (see FIG. 47) has been detached, and thus, the free end 154 of the pusher 152 can be pulled into the lumen 148 of the delivery catheter 150. In some embodiments, the delivery catheter 150 is maintained over the detachable joint 158 during the detachment procedure, to further protect the aneurysm 10. In FIG. 49, the delivery catheter 150 is removed, and the deployed occlusion device 200 is in place to begin to occlude the internal volume 14 of the aneurysm. The distal section 204 also serves to force the proximal section 202 against the neck portion 16 and/or against the interior surface 15, see straight arrow in FIG. 49. The dual layer of mesh in the proximal section 202 at a lower portion 231 (FIGS. 42 and 49) aid in the disruption of blood flow into the aneurysm 10, thus causing thrombosis to isolate the internal volume 14 of the aneurysm 10 from blood flow through the blood vessel. 12. The waist 222 helps the distal section 204 transmit force to the proximal portion 202, though the maximum diameter portions 218, 226 are also configured to transmit force to the substantially flattened portions 220, 224, or the substantially flattened portions 220, 224 transmit to each other, as the waist 222 is longitudinally compressed. The force (straight arrow) maintaining the proximal section 202 in place, further assures this process, and also protects against undesired compaction over time of the occlusion device 200. The dual layers of mesh in the distal section 204 can aid in the healing of the dome. In an unruptured aneurysm, the contact with the dome can cause healing that can thicken the dome at this portion, where the dome is often at is thinnest, most stretched state. In a ruptured aneurysm, the contact with the dome can act like a bandage and accelerate or increase the healing process to further avoid a re-rupture.

The occlusion devices 260, 911, 931 of FIGS. 43-45 are implanted into aneurysms 10 in a similar manner to the occlusion device 200 described in relation to the implantation procedure of FIGS. 46-49. Alternative embodiments of the occlusion devices 200, 260, 911, 931 from FIGS. 41-45 are shown in FIGS. 50-53. Occlusion devices 947, 950, 954, 958 are each similar to occlusion devices 200, 260, 911, 931, respectively, except that the inner layers 948, 951, 955, 959 do not follow the contours of the outer layers 949, 952, 956, 960, but instead are substantially straight tubular columns. These columns may be the diameter of the original tubular mesh (as braided), or may be an expanded diameter (as heat formed). The inner layers 948, 951, 955, 959 can each provide additional column strength and longitudinal support, which can help to apply a force against the aneurysm neck portion 16 with the proximal sections 391, 953, 957, 961.

Figure 54:
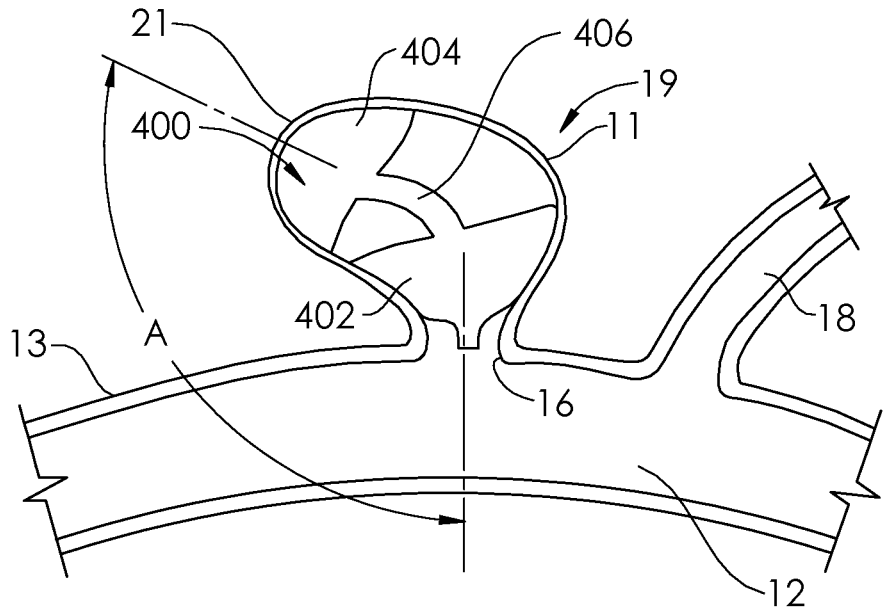
FIG. 54 is an occlusion device according to an embodiment of the present disclosure implanted within an aneurysm.

FIG. 54 illustrates an occlusion device 400 being implanted within an angulated sidewall aneurysm 19 having a dome 21 that is off axis from the neck portion 16. This may be approximated by angle A. The occlusion device 400 is similar to the occlusion device 200, and has a proximal section 402 that is separated from the distal section 404 by an elongate flexible extension 406. The flexible extension 406 may be similar to the central waist 222 of the occlusion device 200, but the diameter and the length may be varied in order to change its flexibility characteristics, and to change to total amount of angulation possible between the proximal section 402 and the distal section 404. The construction of the occlusion device 400 may be identical to any of the embodiments described in relation to the occlusion devices 200, 260, 911, 931, 947, 950, 954, 958 of FIGS. 42-45 and 50-53, however, the longer, more flexible extension 406 allows the distal section 404 to more readily angulate with respect to the proximal section 402. It also allows for a larger amount of angulation between the proximal section 402 and the distal section 404, because of the larger amount of space between them (e.g., because of increased longitudinal distance). Thus, the occlusion device 400 is capable conforming to a large number of different aneurysm shapes or aneurysm angular takeoff angles or general angulations. The occlusion device 400 may be configured to allow for an angle A of between 90° and 180°, or between about 135° and about 180°. Thus, the angle A is changeable to a minimum angle of between about 90 degrees and about 135 degrees. If the elongate flexible extension 406 is long enough, an angulation of less than 90° may even be possible, which might occur in some aneurysms with very odd shapes. The substantially flattened portions may have slight angulations or tapers, as do the substantially flattened portions 220, 224, 276, 278 of FIGS. 42-43 or those in FIGS. 50-51, with the longitudinal space increasing toward the outer diameters, such that the angle A (FIG. 54) is decreased even further. The total longitudinal length of the flexible extension 406 can be between about 0.5 mm and about 30 mm, or between about 0.5 mm and about 25 mm, or between about 1 mm and about 10 mm, or between about 1 mm and about 6 mm, or between about 1 mm and about 3 mm. For cerebral aneurysms, the occlusion device 400 may be configured such that the proximal section 402 and the distal section 404 are each substantially hemispherical in shape, but that the flexible extension, when straight, provides an elongated, revolved oval profile. For example, with the proximal section 402 and the distal section 404 each having a hemisphere shape of about 6 mm in diameter, a 1 mm long flexible extension 406 begets a 7 mm long by 6 mm diameter implant. A 2 mm long flexible extension 406 begets an 8 mm long by 6 mm diameter implant. A 3 mm long flexible extension 406 begets a 9 mm long by 6 mm diameter implant. A wide range of sizes is possible, and the diameter of the proximal section 402 may differ from the diameter of the distal section 404 or they may be substantially the same as each other.

Figure 55:
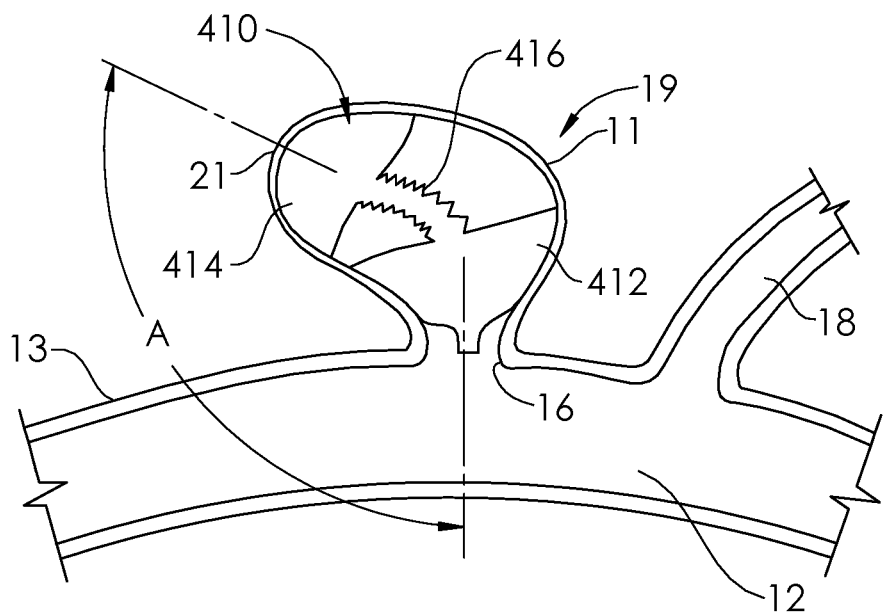
FIG. 55 is an occlusion device according to an embodiment of the present disclosure implanted within an aneurysm.
Figure 56:
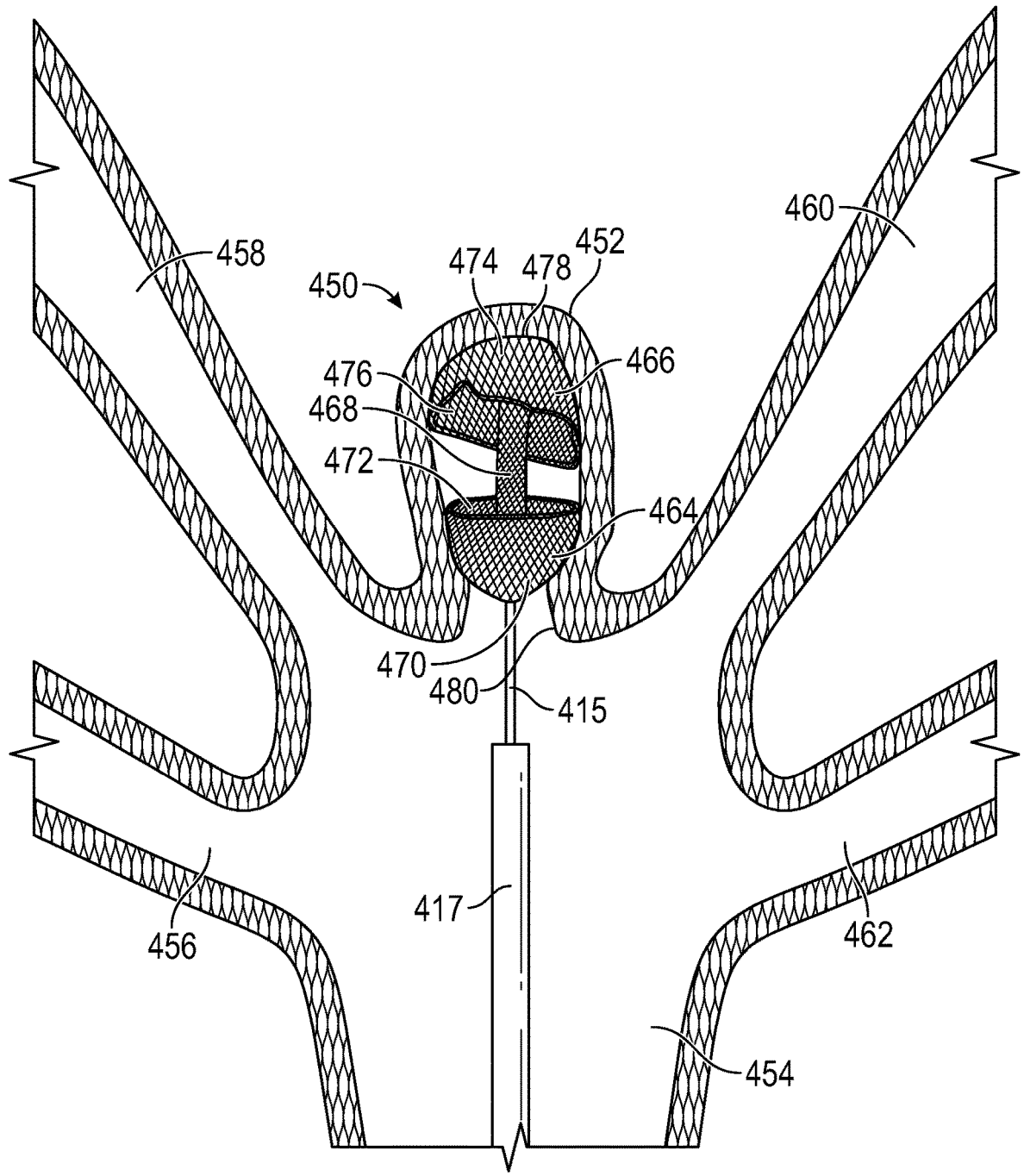
FIG. 56 illustrates an occlusion device according to an embodiment of the present disclosure implanted within an aneurysm.

FIG. 55 illustrates an occlusion device 410 implanted within an angulated sidewall aneurysm 19 via a delivery catheter 417. The occlusion device 410 is similar to the occlusion device 400 of FIG. 54, except the elongate extension 416, extending between the proximal section 412 and the distal section 414, has a bellows configuration that further aids its bendability. Both the inner and outer layer of the mesh tube may include the bellows-type feature, or only the outer layer may include this feature. In alternative embodiments, the flexible section 406 or elongate extension 416 (e.g., comprising a bellows-type feature) can have an outer diameter that varies along its longitudinal axis. For example, the outer diameter may get gradually smaller in the center and larger on the ends and thus have a concave cylindrical shape or hourglass shape. Alternatively, the outer diameter may get gradually larger in the center and smaller on the ends and thus have a convex cylindrical shape or American football shape. FIG. 56 illustrates an occlusion device 450 implanted within an aneurysm 452. The aneurysm 452 is terminal to a main artery 454, and several connecting arteries 456, 458, 460, 462. The occlusion device 450 of FIG. 56 has a proximal section 464 and a distal section 466, separated by an elongated flexible extension 468. The proximal section 464 includes a hemispheric proximal end 470 and a concavity 472 distally, opposite the proximal end 470. The distal section 466 includes a hemispheric distal end 474 and a concavity 476 proximally, opposite the distal end 474. The distal section 466 and the proximal section 464 are each able to pivot (away from the longitudinal axis) in relation to the elongated flexible extension 468, which allows the occlusion device 450, when delivered into the aneurysm 452, to conform to the shape of the inner contours of the aneurysm 452, and thus more snugly fit into the aneurysm 452. As shown in FIG. 56, an apex 478 the distal section 466 of the occlusion device 450 is slightly pivoted back, and to the right. The proximal section 464 is slightly pivoted forward. The proximal section 464 has a maximum diameter that is larger than the diameter or transverse dimension of the aneurysm neck 480. The maximum diameter of the proximal section 464 may also be configured to be oversized in relation to the aneurysm sac, in order to apply a gripping radial force. The same is true of the distal section 466. Once in the preferred position within the aneurysm 452, the occlusion device 450 is then detached from the pusher 415.

Figure 57:
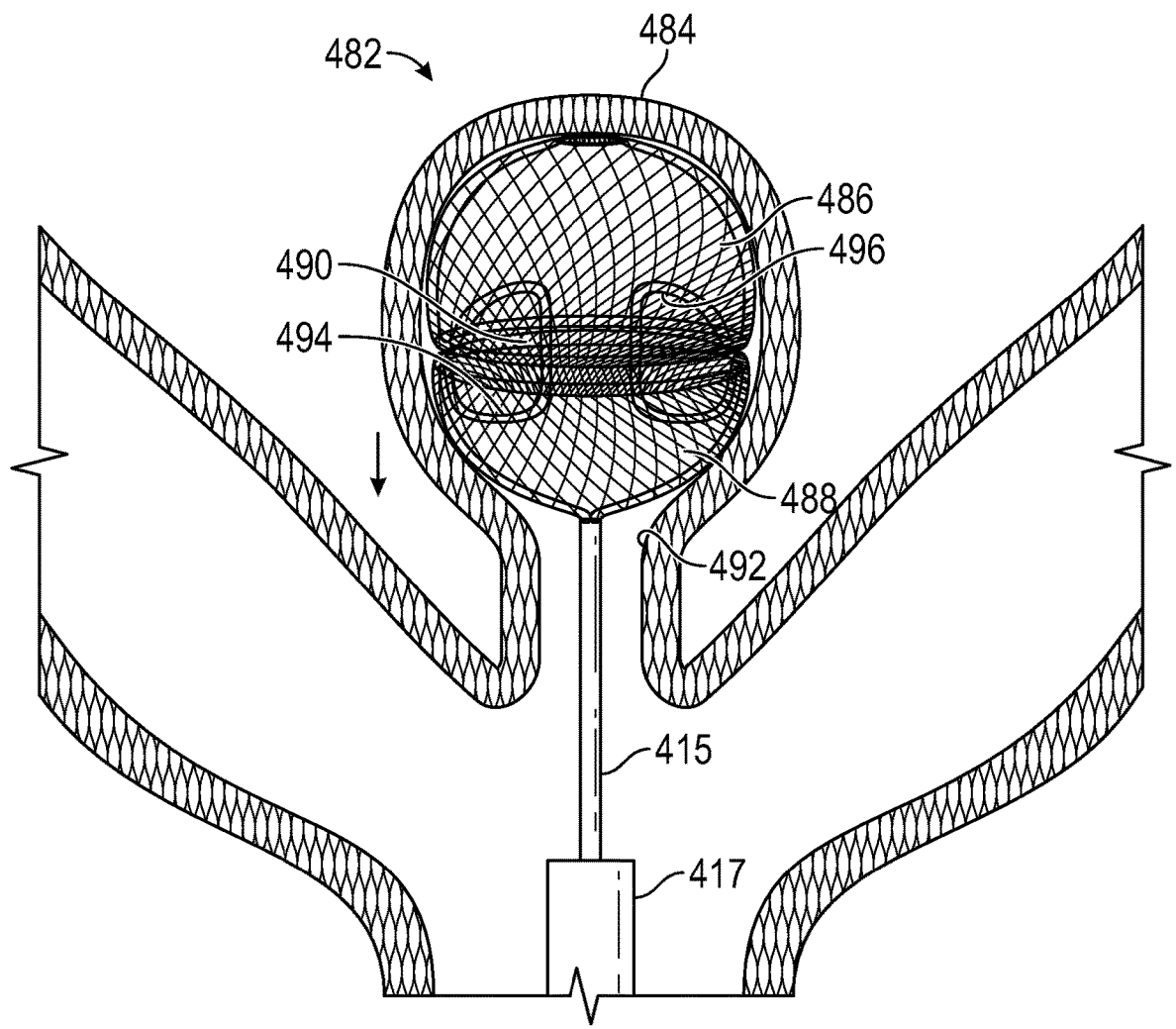
FIG. 57 illustrates an occlusion device according to an embodiment of the present disclosure implanted within an aneurysm
Figure 58:
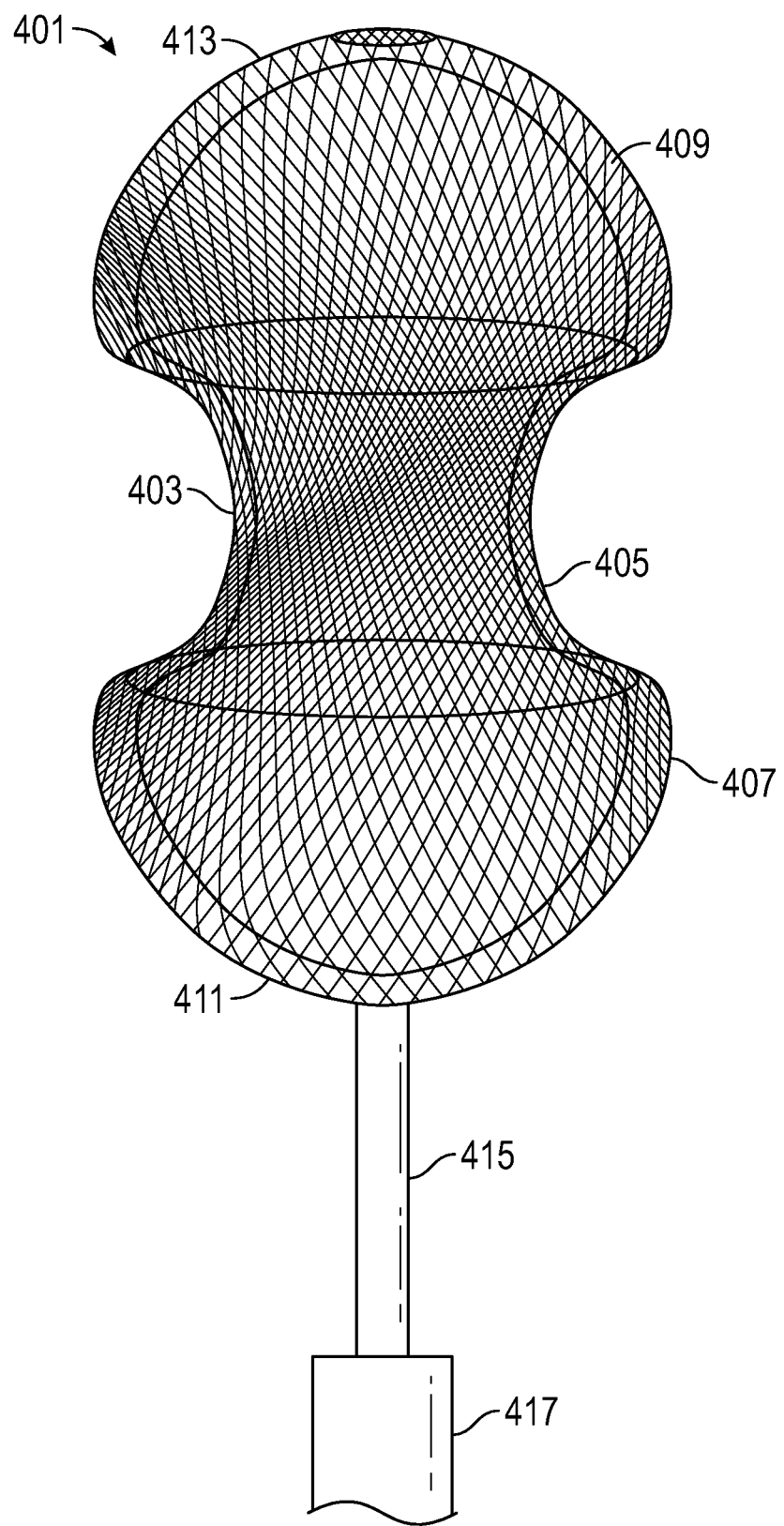
FIG. 58 illustrates an occlusion device according to an embodiment of the present disclosure.
Figure 59:
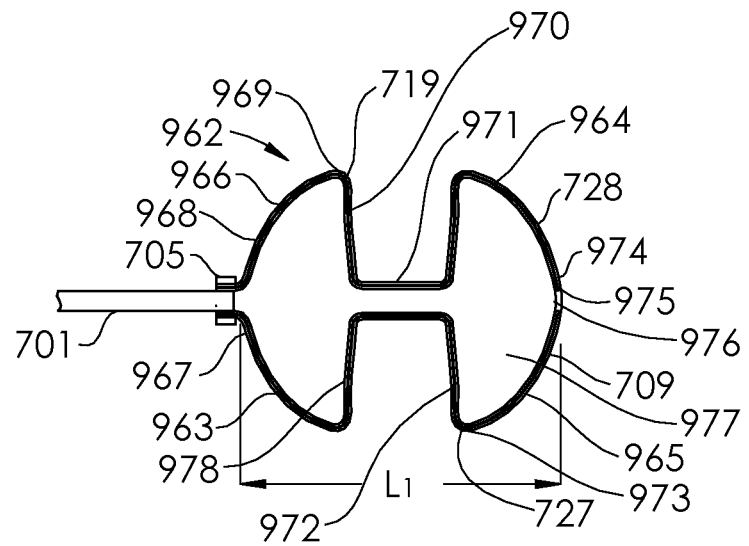
FIG. 59 is a sectional view of an unrestrained occlusion device according to an embodiment of the present disclosure.
Figure 60:
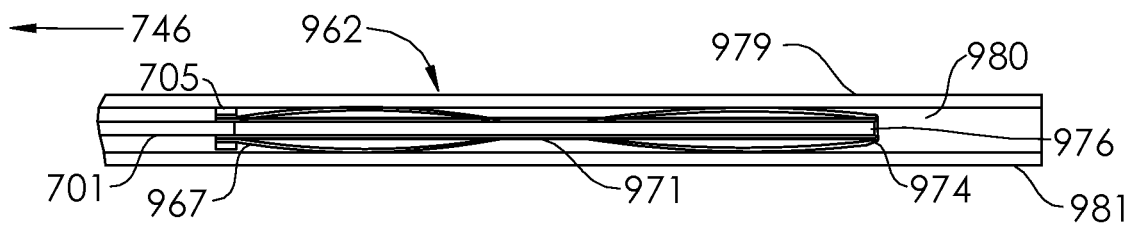
FIG. 60 is the occlusion device of FIG. 59 restrained within a delivery catheter.
Figure 61:
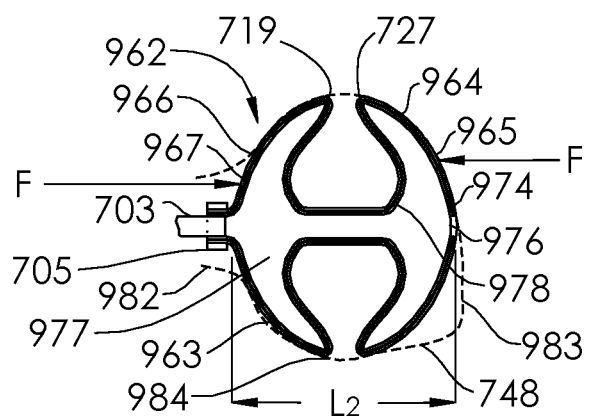
FIG. 61 is the occlusion device of FIG. 59 delivered restrained within an aneurysm.

FIG. 57 illustrates an occlusion device 482 being implanted within an aneurysm 484. The occlusion device 482 of FIG. 57 is similar to the occlusion device 200 of FIGS. 41-42, but has slightly different dimensions. As the occlusion device 482 is implanted within the aneurysm, the distal section 486 and the proximal section 488 are compressed longitudinally together. The waist 490 is able to deform somewhat (e.g., shorten and widen) to allow the dynamic shaping of the occlusion device 482 to occur when implanted into the aneurysm 484. The proximal section 488 is forced (straight arrow) against the neck 492. The substantially flattened portion 494 of the proximal section 488 and the substantially flattened portion 496 of the distal section 486 are each able to flex to form ring-shaped concavities. The flexing acts as a spring, to maintain the force of the proximal section 488 against the neck 492. An occlusion device 401 having a relatively wider waist 403 and relatively longer flexible extension 405 between its proximal section 407 and its distal section 409. is shown in FIG. 58. The waist 403 of the occlusion device of FIG. 58 has a circumferentially extending concavity (hourglass shape) and comprises a hemispherical proximal face 411 and a hemispheric distal face 413. The occlusion devices of FIGS. 56-58 are shown still coupled to the pusher 415 and being delivered through a delivery catheter 417. FIGS. 59-61 illustrate three different configurations of an occlusion device 962. In FIG. 59, the occlusion device 962, as heat-formed, is in a completely unrestrained, expanded configuration. In FIG. 60, the occlusion device 962 is constrained within a microcatheter lumen 980. In FIG. 61, the occlusion device 962 has been delivered into an aneurysm 748.

FIG. 59 illustrates an occlusion device 962 comprising a proximal section 963 and a distal section 964 and a waist 971, all constructed of a single, continuous dual layer mesh. The occlusion device 962 is constructed from an inverted mesh tube 965 having a first end, a second end, and a wall (as in the occlusion device of FIGS. 41-42). The inverted mesh tube 965 extends on an outer layer 966 past a proximal end 967 of the proximal section 963 and along a hemisphere shape 968 to a maximum diameter portion 969 having an acute angulation 719. From the maximum diameter portion 969, the outer layer 966 extends radially inward along a substantially flattened portion 970 to the central waist 971. The outer layer 966 then extends radially outward along a substantially flattened portion 972 of the distal section 964 to a maximum diameter portion 973 having an acute angulation 727 to a hemisphere shape 728 to a distal end 974 of the occlusion device 962. The hemisphere shape 728 is configured to contact at least a portion of an aneurysm dome. The maximum diameter portion 973 has a diameter that is about equal to the diameter of the maximum diameter portion 969, but in other embodiments, they may differ. At the distal end 974, the wall 709 is inverted inwardly at an inversion fold 975, which creates a distal orifice 976 and an internal volume 977. The wall 709 transitions at the inversion fold 975 from the outer layer 966 to an inner layer 978 which follows the contours of the outer layer 966 from the distal orifice 976 to the first end. The occlusion device 962 is shown coupled to an elongate pusher 701 and a marker band 705.

In FIG. 59, the occlusion device 962 is shown unrestrained. Thus, if the mesh tube 965 is formed of at least some nickel-titanium, or shape memory alloy, filaments, braided together, the shape shown in FIG. 59 can be heat formed, as described herein. The occlusion device 962, in its compressed configuration, is shown in FIG. 60, inserted through the lumen 980 of a delivery catheter 979 having a distal end 981 and a proximal end 746. FIG. 61 shows the occlusion device 962 within an aneurysm 748 having a neck 982 and a dome 983. The proximal section 963 and a distal section 964 are each deformed from contact with the aneurysm wall 984, thus confirming to the aneurysm wall 984 in a snug manner. The overall length $L_2$ of the occlusion device 962 becomes less than the original length $L_1$ (FIG. 59) because of longitudinal compressive forces F applied in return by the aneurysm wall 984. Thus, the overall shape of the occlusion device within the aneurysm 748 in FIG. 61 becomes more spherical than that of the unrestrained shape in FIG. 59. The proximal end 967 and the marker band 705 are at or adjacent the neck 982 of the aneurysm 748, while the distal section 964 is adjacent the dome 983. FIG. 61 also shows a remnant 703 of the pusher 701 after detachment has occurred. In some embodiments, no remnant of the pusher 701 remains after detachment. The occlusion device 962 is very conformable with different aneurysmal shapes and sizes. Because of this, the occlusion device 962 may also fit into an aneurysm that is longitudinally longer and diametrically narrower than the aneurysm 748 of FIG. 61. It may also fit into an aneurysm that has a significantly non-symmetric shape.

Figure 62:
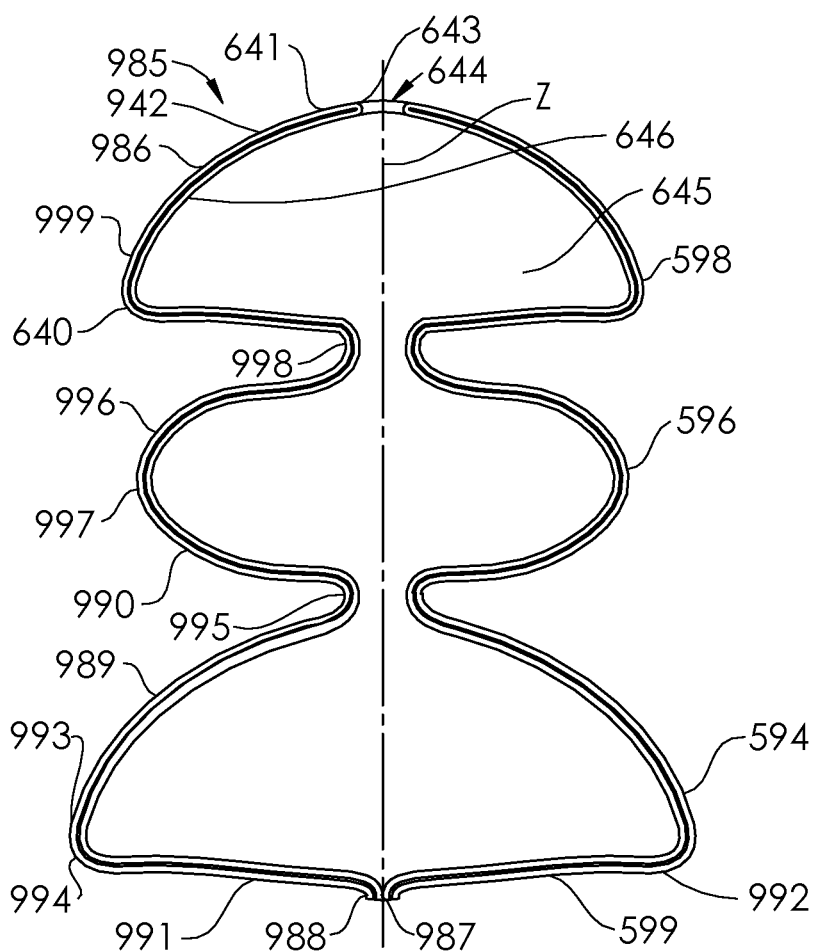
FIG. 62 is a sectional view of an occlusion device according to an embodiment of the present disclosure.

Turning to FIG. 62, an occlusion device 985 is constructed from an inverted mesh tube 986 having a first end 987, a second end 988, and a wall 989. The inverted mesh tube 986 extends on an outer layer 990 from the second end 988 past a proximal end 991 of the proximal section 992 and along a lower mushroom shape 993 to a maximum diameter portion 994. From the maximum diameter portion 994, the outer layer 990 extends radially inward along the mushroom shape 988 to a first central waist 995. The outer layer 990 then extends radially outward along a globular portion 996 having a maximum diameter portion 997 and then to a second central waist 998. Though the globular portion 996 of the occlusion device 985 is relatively short and wide, in other embodiments, the opposite might be true, with the globular portion 996 having more of an American football shape. In other embodiments, the globular portion 996 may have a generally spherical shape. The outer layer 990 then forms an upper mushroom shape 999 having a maximum diameter 640 to a distal end 641 of the occlusion device 985. The hemisphere shape 642 of the upper mushroom shape 999 is configured to contact an aneurysm dome. The maximum diameter 640 is about equal to the maximum diameter 997, but in other embodiments, they may differ. The occlusion device 985 is substantially cylindrically symmetric around a central axis Z. However, in alternative embodiments, there may be certain portions of asymmetry, such as one or more indented or extended feature at a particular location in a perimeter. At the distal end 641, the wall 989 is inverted inwardly at an inversion fold 643, which creates a distal orifice 644 and an internal volume 645. The wall 989 transitions at the inversion fold 643 from the outer layer 990 to an inner layer 646 which follows the contours of the outer layer 990 from the distal orifice 644 to the first end 987. The occlusion device 985 is fabricated as an inverted mesh tube 986 having a simple straight elongate configuration, and is subsequently formed into the shape shown in FIG. 62 and heat set into this shape. Each of the three sections, a proximal section 594, a central section 596, and a distal section 598, are shown in FIG. 62 in their expanded configurations, but are configured to be compressed or compacted within the lumen 148 of a delivery catheter 150 (e.g., microcatheter). The proximal end 991, located on the lower portion of the proximal section 594 has a flat surface 599 or substantially flat surface, and is configured for engaging, and even gripping, the aneurysm neck at the interior portion of the aneurysm. The engagement of the aneurysm neck by the flat surface 599 or substantially flat surface may help seal the aneurysm and help prevent an endoleak. The globular portion 996/central section 596 is configured to allow the angulation between the proximal section 594 and the distal section 598, while providing some body, or a stop/limit in between.

In some embodiments, one or more of the proximal section 594, central section 596, or distal section 598 may comprise some nickel-titanium alloy filaments and some radiopaque elements, comprising platinum, gold, tantalum, or alloys of any of these or other radiopaque materials. In some embodiments, the filaments may comprise drawn filled tubes, such as those comprising a nickel-titanium alloy outer wall and a platinum core. The radiopaque material allows the occlusion device 985 to be visible on radiographs or fluoroscopy. The occlusion device 985 may be configured by controlling how much radiopaque material is used, by either the ratio of radiopaque filaments to non-radiopaque filaments, or by the amount of platinum core in the drawn filled tubes. In this manner, the occlusion device 985 can be selectively fabricated to be sufficiently visible, but not over visible, e.g., overly bright, such that other objects are obscured. In some embodiments, whether any of the filaments comprise radiopaque materials or not, a marker band may be attached to the first end 987 and/or second end 988 of the inverted mesh tube 986, by adhesive or epoxy bonding, or swaging, welding or other mechanical attachment.

Figure 63:
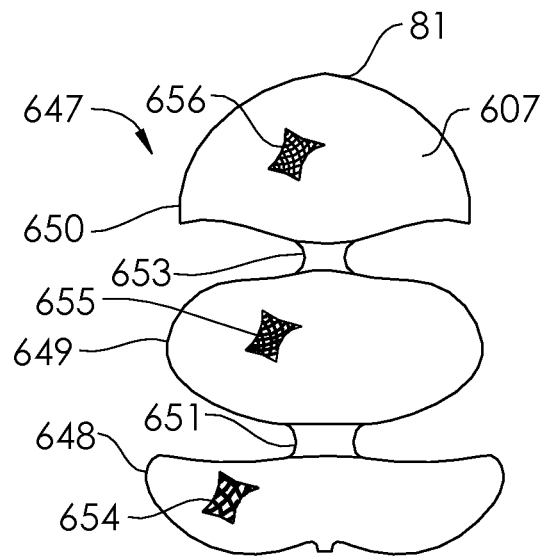
FIG. 63 is a side view of an occlusion device according to an embodiment of the present disclosure.

FIG. 63 illustrates an occlusion device 647 having an inverted mushroom-shaped proximal section 648, a globular central section 649, and a mushroom-shaped distal section 650 having a distal apex 81. Each of the sections 648, 649, 650 are separated by central waists 651, 653. Sections 648, 649 are separated by central waist 651 and sections 649, 650 are separated by central waist 653. Each of the sections 648, 649, 650 are formed from braided mesh 607 having different stiffness characteristics from each other. Though the sections 648, 649, 650 are fully braided, the braiding is only shown in windows 654, 655, 656 for simplicity. The proximal section 648 is braided such that it is stiffer than either the central section 649 or the distal section 650. The proximal section 648 may be braided by larger diameter filaments, and/or may be braided with larger braid angles, to achieve the increased stiffness. The increased stiffness is configured for securely wedging or setting against the aneurysm neck, for example, to achieve better closure or disruption at the entry to the aneurysm. The distal section 650 is braided such that it is less stiff/more flexible than either the central section 649 or the proximal section 648. The distal section 650 may be braided by smaller diameter filaments, and/or may be braided with smaller braid angles, to achieve the decreased stiffness. The decreased stiffness is configured for softly setting against the aneurysm dome. This is particularly helpful in avoiding a rupture of an aneurysm, for example, a high-risk aneurysm. A high-risk aneurysm may have a substantially large diameter, or a substantially thin wall at the dome. Another high-risk aneurysm may be a previously ruptured aneurysm that has at least partially healed, but which may be prone to rerupture. The central section 649 may be braided by filaments, and/or may be braided with braid angles, that achieve an intermediate stiffness to the proximal section 648 and the distal section 650. Changes in wire/filament diameter be may be created after forming the braided mesh 607 from a single set of wires, by adjusting or rearranging the braid crossings. In some embodiments, the distal section 650 may be subsequently etched (chemical etch, photochemical etch) to decrease the overall wire diameter and decrease the stiffness. In some embodiments, both the distal section 650 and the central section 649 are etched in a first etching operation. Then, only the distal section 650 is etched in a second etching operation. This, as originally formed, the proximal section 659, central section 649, and distal section 650 are formed from wires having the same diameter, but after the two etching operations, the distal section 650 has smaller diameter wires than the central section 649 and the central section 649 has smaller diameter wires than the proximal section 648. Thus, in some embodiments, the distal section 650 may be made more flexible than the proximal section 648 via etching alone.

Figure 64:
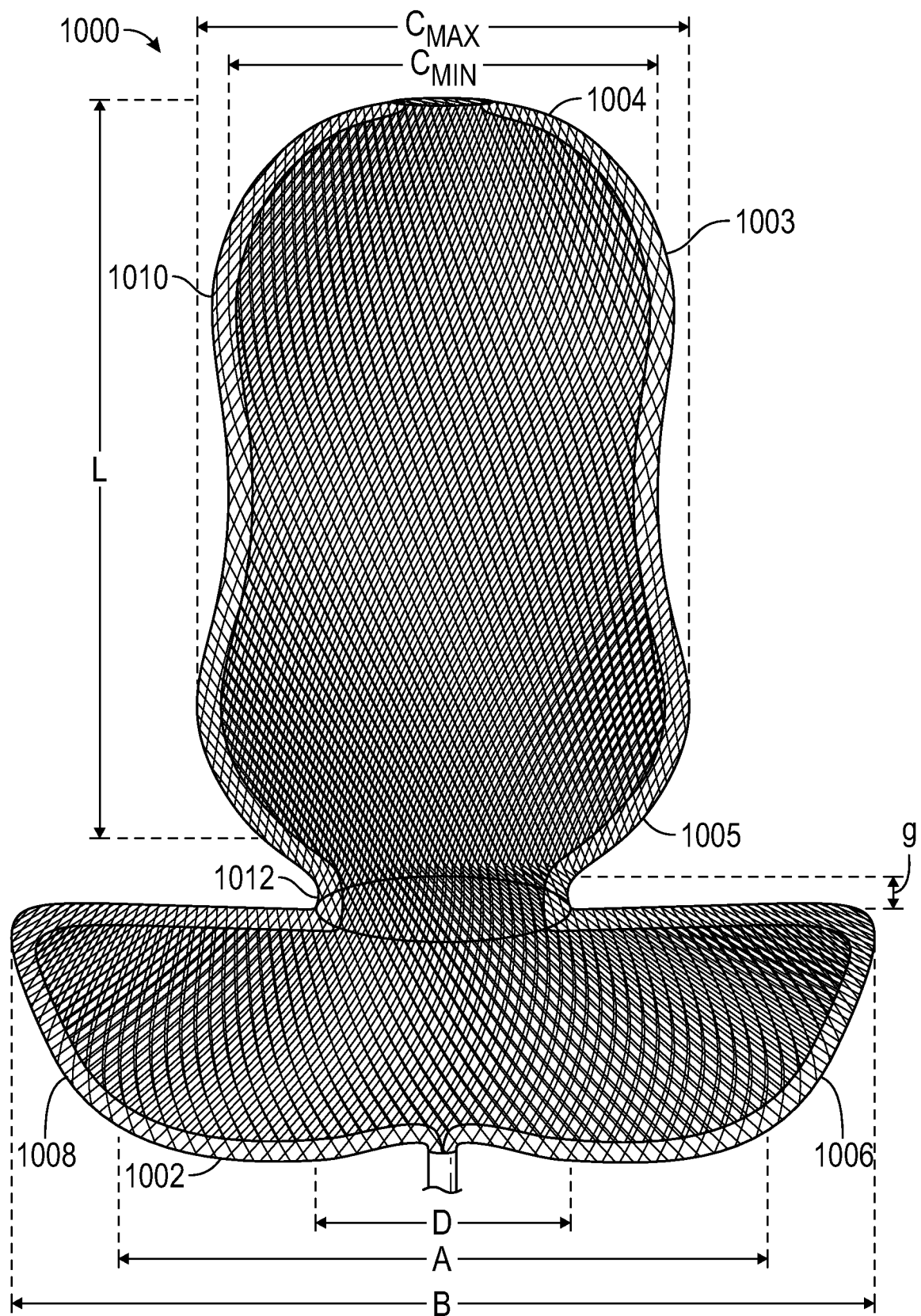
FIG. 64 is a plan view of an occlusion device according to an embodiment of the present disclosure.

FIG. 64 illustrates an occlusion device 1000 having a proximal end 1002 and a distal end 1004 and configured for placement within an aneurysm. The occlusion device 1000 comprises a lower portion 1006 having a proximal outer diameter A and a distal outer diameter B and a tapered frustoconical section 1008 extending between diameter A and diameter B. In some embodiments, the lower portion 1006 is circular, with substantially the same diameter at any transverse slice (around the perimeter). In other embodiments, the lower portion 1006 is non-circular, and may comprise an ellipse, an oval, a polygon or other shapes. The tapered frustoconical section 1008 is configured to be larger than a maximum transverse dimension of an opening into the aneurysm (the neck portion) at at least some portion between A and B. In some embodiments, the diameter A is configured to be larger than a maximum transverse dimension of an opening into the aneurysm (the neck portion). Thus, the lower portion 1006 is configured to completely cover the neck portion, and thus to cause stagnation of blood within the aneurysm, leading to occlusion. The occlusion device 1000 is constructed from a mesh (braided) Nitinol (nickel-titanium alloy) tube 1005 that is inverted on itself. The mesh tube 1005 has a first end and a second end. The second end is folded back over the outer diameter of the first end thus providing an outer facing surface 1003 and an inner facing surface (not visible in FIG. 64). The mesh tube 1005 is heat-formed such that the occlusion device 1000 comprises several expanded portions: the lower portion 1006, an upper portion 1010, and an intermediate waist portion 1012. The upper portion 1010 has a length L, a maximum diameter $C_{MAX}$ and a minimum diameter $C_{MIN}$. The waist portion 1012 has a diameter D and a length g.

Particular ratios of the dimensions of the occlusion device 1000 have been found to be effective in creating a simple, easily-formed structure (body) that is particularly suited to be placed within aneurysms that may have at least one elongated dimension. For example, an aneurysm that is deep and narrow, or an aneurysm that is wide and short. The length of L of the upper portion 1010 may range from between about 1 mm to about 25 mm. The diameter C may range from between about 1 mm and about 25 mm. The diameter B may range from between about 1 mm and about 25 mm. The diameter A may range from between about 1 mm and about 24 mm. Generally, the diameter C is between about 50% to about 100% of the diameter B. Furthermore, generally, the diameter A is between about 50% to about 100% of the diameter B. In some embodiments, the diameter A is between about 70% and about 90% of the diameter B.

As formed (e.g., heat-formed), the occlusion device 1000 has an expanded configuration (shown in FIG. 64) and a collapsed configuration, configured for delivery through the lumen of a delivery catheter (e.g., microcatheter). The occlusion device 1000 comprises two mesh layers, provided by the outer facing surface 1003 and the inner facing surface. In some embodiments, the occlusion device 1000 may comprise some nickel-titanium alloy filaments and some radiopaque elements, comprising platinum, gold, tantalum, or alloys of any of these or other radiopaque materials. In some embodiments, the filaments may comprise drawn filled tubes (DFT), such as those comprising a nickel-titanium alloy outer wall and a platinum core. The radiopaque material allows the occlusion device 1000 to be visible on radiographs or fluoroscopy. The occlusion device 1000 may be configured by controlling how much radiopaque material is used, by either the ratio of radiopaque filaments to non-radiopaque filaments, or by the amount of platinum core in the drawn filled tubes. In this manner, the occlusion device 1000 can be selectively fabricated to be sufficiently visible, but not over visible, e.g., overly bright, such that other objects are obscured. In some embodiments, whether any of the filaments comprise radiopaque materials or not, a marker band may be attached to the proximal end 1002 of the occlusion device 1000, by adhesive or epoxy bonding, or swaging, welding or other mechanical attachment. The drawn filled tubes (DFT) may each have a platinum core that has a cross-sectional area that is between about 10% and about 70% of the total cross-sectional area of the DFT. In some embodiments, all (100%) of the filaments may comprise DFTs. In other embodiments, between 50% and 100% of the filaments may comprise DFTs, with the remainder of the filaments comprising only nickel-titanium alloy.

Figure 65:
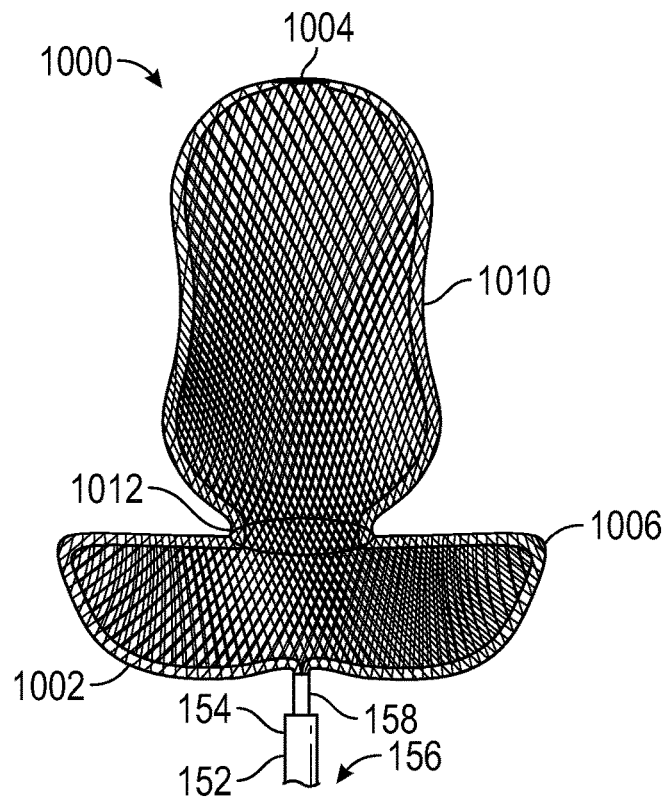
FIG. 65 is a plan view of the occlusion device of FIG. 64 releasably coupled to a pusher, according to an embodiment of the present disclosure.

Turning to FIG. 65, the occlusion device 1000 may be coupled at or near its proximal end 1002 to a pusher 152, having a distal end 154 and a proximal end 156. The pusher 152 may comprise a wire, a hypo tube, or another elongate structure having column support is detachably coupled at its distal end 154 to the proximal end 1002 of the occlusion device 1000. A detachable joint 158 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. During delivery, the pusher 152 is held on its proximal end 156 by a user and pushed in a forward longitudinal direction in order to advance the occlusion device 1000 to the distal end of a delivery catheter (e.g., a microcatheter) having a delivery lumen. The delivery catheter may also include a proximal hub, such as a luer connector.

Figure 66:
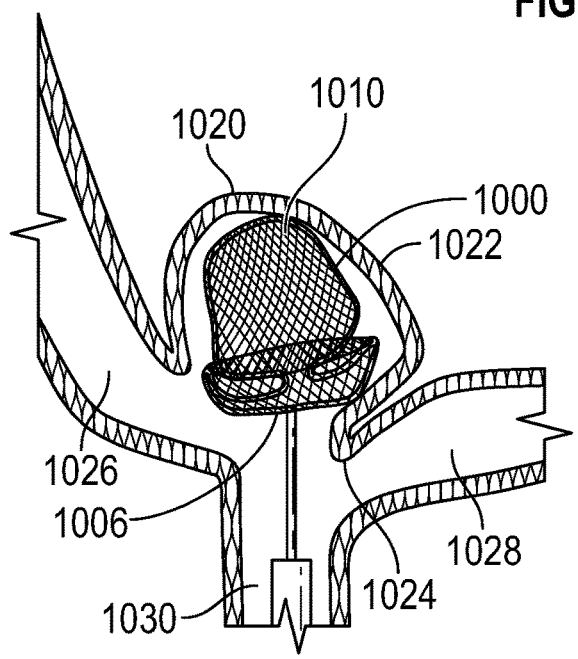
FIG. 66 is a perspective view of the occlusion device of FIG. 64 implanted within a simulated aneurysm, according to an embodiment of the present disclosure.
Figure 67:
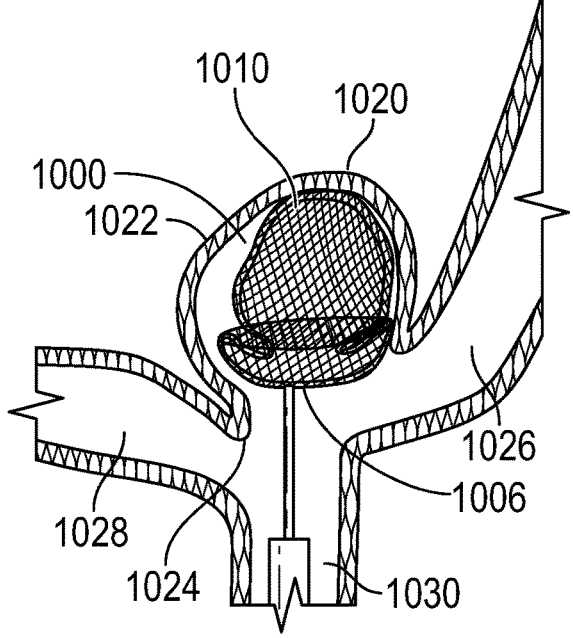
FIG. 67 is a perspective view of the occlusion device of FIG. 64 implanted within a simulated aneurysm, according to an embodiment of the present disclosure.

FIG. 66 illustrates a first view of the occlusion device 1000 delivered into a first aneurysm configuration 1020 comprising an aneurysm 1022, a neck 1024, a first parent vessel arm 1026, a second parent vessel arm 1028, and an additional connecting vessel 1030. FIG. 67 illustrates a different view. The waist portion 1012 allows some flexure between the upper portion 1010 and the lower portion 1006, and thus the upper portion 1010 is able to be somewhat compressed into the lower portion 1006, as seen in FIGS. 66 and 67. Thus, the lower portion 1006 protects and covers the neck 1024 of the aneurysm 1022 while the upper portion 1010 allows the occlusion device 1000 to adapt to the shape of the aneurysm 1022 for a snug by safe fit. The waist portion 1012 also acts as a shock absorber.

Figure 68:
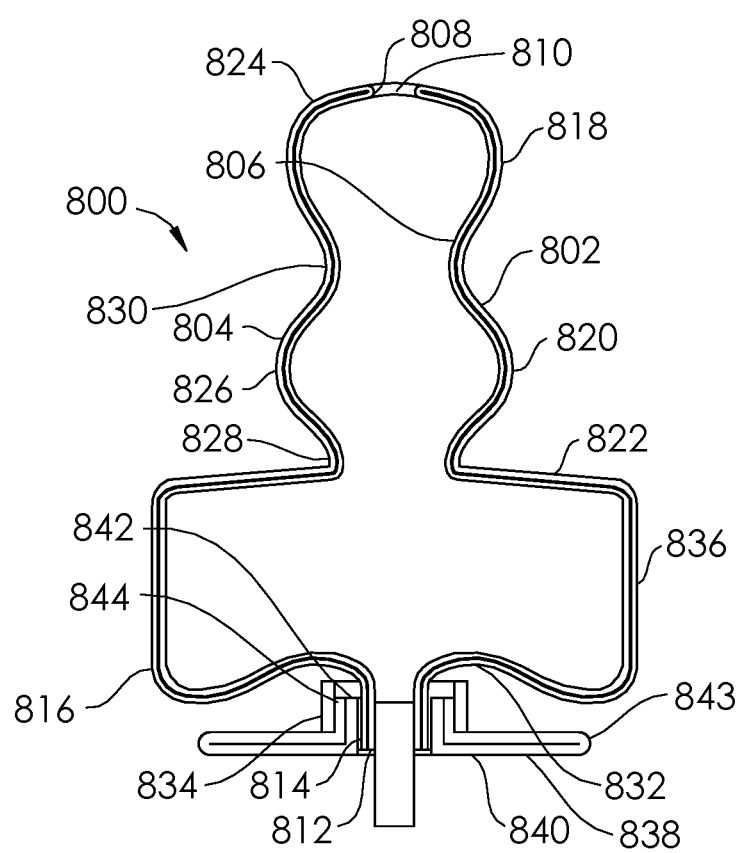
FIG. 68 is a sectional view of an alternative occlusion device, according to an embodiment of the present disclosure.

FIG. 68 illustrates an occlusion device 800 also comprising an inverted mesh tube 802 and having an outer layer 804, an inner layer 806, and an inversion fold 808, which creates a distal orifice 810, and serves as the transition between the outer layer 804 and the inner layer 806. The inverted mesh tube 802 has a first end 812 and a second end 814. The occlusion device 800 includes a proximal section 816, a distal section 818, and an intermediate section 820. The proximal section 816 has a substantially flattened portion 822, and the distal section 818 has a globular shape 824, configured to contact an aneurysm dome. The intermediate section 820 also has a globular shape 826. There is a waist 828 between the proximal section 816 and the intermediate section 820, and a circumferentially extending concavity 830 between the distal section 818 and the intermediate section 820. The proximal section 816 includes a proximal concavity 832 concavity, which is configured to clear a marker band 834. The proximal section 816 has a maximum diameter 836 configured to grip and internal wall of an aneurysm. The occlusion device 800 comprises a cover 838 configured to seat adjacent a neck of the aneurysm. In some embodiments, the cover 838 is circular, with substantially the same diameter at any transverse measurement around the perimeter. In other embodiments, the cover 838 is non-circular, and may comprise an ellipse, an oval, a polygon or other shapes. In the non-circular embodiments, the cover 838 comprises a minimum transverse dimension and a maximum transverse dimension. In the particular case of an ellipse or an oval shape, the cover 838 comprises a major diameter and a minor diameter. The minor diameter or minimum transverse dimension is configured to be larger than a maximum transverse dimension of an opening into the aneurysm (the neck portion). Thus, the cover 838 is configured to completely cover the neck portion, and thus to cause stagnation of blood within the aneurysm, leading to occlusion. The cover 838 is constructed from a mesh (braided) Nitinol (nickel-titanium alloy) tube 840 that is inverted on itself. The mesh tube 840 has a first end 842 and a second end 844. The second end 844 is folded back over the outer diameter of the first end 842. The mesh tube 840 is heat-formed such that cover 838 comprises an expanded portion 843 and the first end 842 and second end 844 comprise unexpanded (or partially expanded) portions. The cover 838 is fabricated as an inverted mesh tube 840 having a simple straight elongate configuration, and is subsequently formed into the shape shown in FIG. 68, and heat set into this shape. For example, the inverted mesh tube 840 may be constructed as a single layer mesh tube formed of at least some nickel-titanium alloy filaments, and then inverted on itself. The inverted mesh tube 840 may then be placed into a die or mold comprising one or more pieces, to hold it in the shape of the cover 838. Then, the cover 838 may be subjected to an elevated temperature and then cooled, to lock in the shape, resulting in a cover 838 having at least some superelastic properties.

The occlusion device 800 may comprise any of the materials and be made with any of the processes described in relation to the occlusion device 200, or any other of the occlusion devices described herein. The occlusion device 800 is configured to have flexing or articulating capabilities at the waist 828 and at the circumferentially extending concavity 830 which thus allow the proximal section 816, the distal section 818, and the intermediate section 820 to bend and conform to aneurysms of complex and irregular shapes. The maximum diameter 836 is configured to apply a radial force to the aneurysm wall to keep the occlusion device 800 in place, while the cover 838 facilitates thrombosis and closure of the aneurysm at the neck.

While the foregoing is directed to embodiments of the present disclosure, other and further embodiments may be devised without departing from the basic scope thereof. The filament diameter of the filaments comprising any of the mesh material (e.g., mesh tube including inverted mesh tubes) described herein may be between about 0.0004 inch and about 0.003 inch, or between about 0.0005 inch and about 0.002 inch, or between about 0.0006 inch and about 0.002 inch, or between about 0.0006 inch and about 0.0015 inch. The drawn filled tubes (DFT) may comprise between 0% and 100% of the total strands/filaments in any of the braided/mesh tubes. In some embodiments, the drawn filled tubes (DFT) comprise about 50% to about 100% of the total filaments of the cover and about 50% to about 100% of the total filaments of each of the doubled-over or looped tubular mesh. The radiopaque core of each of at least some of the drawn filled tubes has a cross-sectional area that is between about 10% and about 70% of the total cross-sectional area of the each of at least some of the drawn filled tubes, or between about 51% and about 70% of the total cross-sectional area of the each of at least some of the drawn filled tubes. In some embodiments, NiTi #1-DFT® wire produced by Fort Wayne Metals Research Products Corp. (Fort Wayne, IN USA) may be utilized. The filaments may be braided with patterns having filament crossings that are in any one or more of the following ratios of filaments: 1×1, 1×2, 2×1, 2×2, 2×3, 3×2, 3×3, etc. (e.g., warp and weft). Any low, moderate, or high pick counts may be used, for example, between about 15 picks per inch and about 300 picks per inch, or between about 20 picks per inch and about 160 picks per inch. Any of the filaments or any of the portion of the occlusion devices may be coated with compounds that enhance endothelialization, thus improving the healing process when implanted within the aneurysm, and optimizing occlusion. The pusher and occlusion device configurations presented herein may also be used for in other types of implantable devices, such as stents, flow diversion devices, filters, and occlusion devices for structural heart defects.

In some embodiments, braided elements may be subsequently etched (chemical etch, photochemical etch) to decrease the overall wire diameter and decrease the stiffness.

Additional materials may be carried on the cover of the occlusion device, or any other proximal portion of the occlusion device, and configured to face opposite the aneurysm neck. In some embodiments, the material on the occlusion device may comprise a biological layer, configured to encourage growth. In some embodiments, the biological layer may comprise antibodies, in order to accelerate the formation of an endothelial layer, for example, by attracting endothelial progenitor cells (EPCs). In some embodiments, the biological layer may comprise a natural membrane or structure, such as a membrane, such as a membrane from an ear, or a cornea, or an ultra-thin piece of ligament, or even a piece of blood vessel wall. In some embodiments, the material on the occlusion device may comprise a polymer layer configured to act as a simulated arterial wall. In some embodiments, the polymer layer may comprise polytetrafluoroethylene, such as expanded polytetrafluoroethylene (ePTFE), such as that used in grafts. Occlusion devices as described herein may incorporate biological or polymeric layers.

The following clauses include examples of apparatus of the disclosure.

Clause 101: In one example, an apparatus for treating an aneurysm in a blood vessel includes an occlusion element configured to be releasably coupled to an elongate delivery shaft, the occlusion element including a mesh body configured to be delivered in a collapsed configuration through an inner lumen of a delivery catheter, the inner lumen having a proximal end and a distal end, the body further configured to expand to an expanded configuration when advanced out of the distal end of the inner lumen of the delivery catheter and into the aneurysm, wherein the body includes a proximal portion having a proximal maximum transverse dimension A and a distal maximum transverse dimension B and a frustoconical portion extending between the proximal maximum transverse dimension A and the distal maximum transverse dimension B, and wherein the body further includes distal portion having a maximum transverse dimension C and a waist portion between the proximal portion and the distal portion, and wherein the dimension A is between about 50% and about 100% of dimension B.

Clause 102: In some examples, the apparatus includes clause 101, wherein the dimension A is between about 70% and about 90% of dimension B.

Clause 103: In some examples, the apparatus includes clause 101, wherein the dimension C is between about 50% and about 100% of dimension B.

Clause 104: In another example, an apparatus for treating an aneurysm in a blood vessel, includes an occlusion element configured to be releasably coupled to an elongate delivery shaft, the occlusion element including an inverted mesh tube having an outer layer and an inner layer, the outer layer transitioning to the inner layer at an inversion fold, wherein at least the outer layer is formed into an expanded shape having a proximal section having a first diameter, a distal section having a second diameter, and a waist portion having a third diameter, wherein the third diameter is less than the first diameter and the third diameter is less than the second diameter.

Clause 105: In some examples, the apparatus includes clause 104, wherein the inner layer has an expanded shape which conforms with the expanded shape of the outer layer.

Clause 106: In some examples, the apparatus includes either one of clauses 104 or 105, wherein the first diameter is about equal to the second diameter.

Clause 107: In some examples, the apparatus includes either one of clauses 104 or 105, wherein the first diameter is greater than the second diameter.

Clause 108: In some examples, the apparatus includes either one of clauses 104 or 105, wherein the first diameter is less than the second diameter.

Clause 109: In some examples, the apparatus includes any one of clauses 104-108, wherein distal section has a substantially hemispherical shape.

Clause 110: In some examples, the apparatus includes any one of clauses 104-109, wherein the proximal section has a substantially hemispherical shape.

Clause 111: In some examples, the apparatus includes any one of clauses 104-109, wherein the proximal section includes a proximal portion having a concave conical shape.

Clause 112: In some examples, the apparatus includes any one of clauses 104-111, wherein the inversion fold is a circular shape surrounding an orifice that communicates with an internal volume of the occlusion element.

Clause 113: In some examples, the apparatus includes clause 111, wherein the concave conical shape is configured to guide blood flow within a native blood vessel adjacent to an aneurysm when the occlusion element is substantially implanted within the aneurysm.

Clause 114: In some examples, the apparatus includes any one of clauses 104-113, wherein the proximal section and the distal section are configured to flex with respect to each other so that they do not share the same longitudinal axis.

Clause 115: In some examples, the apparatus includes clause 114, wherein the waist portion is provided by an elongate tubular section.

Clause 116: In some examples, the apparatus includes either one of clauses 114 or 115, wherein the waist portion is provided by a bellows-shaped element.

Clause 117: In some examples, the apparatus includes any one of clauses 114-116, wherein a longitudinal axis of the proximal section and a longitudinal axis of the distal section are configured to be moveable between 900 and 180°.

Clause 118: In some examples, the apparatus includes clause 117, wherein a longitudinal axis of the proximal section and a longitudinal axis of the distal section are configured to be moveable between 135° and 180°.

Clause 119: In some examples, the apparatus includes clause 115, wherein the tubular section has a length of between about 1 mm and about 10 mm.

Clause 120: In some examples, the apparatus includes clause 115, wherein the tubular section has a length of between about 1 mm and about 6 mm.

Clause 121: In some examples, the apparatus includes clause 115, wherein the tubular section has a length of between about 1 mm and about 3 mm.

Clause 122: In some examples, the apparatus includes any one of clauses 104-121, wherein the occlusion element includes a nickel-titanium alloy.

Clause 123: In some examples, the apparatus includes any one of clauses 104-122, wherein the occlusion element includes a radiopaque material.

Clause 124: In some examples, the apparatus includes clause 123, wherein the radiopaque material includes a marker band.

Clause 125: In some examples, the apparatus includes clause 124, wherein the marker band is coupled to the proximal section.

Clause 126: In another example, an apparatus for treating an aneurysm in a blood vessel, including an occlusion element configured to be releasably coupled to an elongate delivery shaft, the occlusion element including an inverted mesh tube having an outer layer and an inner layer, the outer layer transitioning to the inner layer at an inversion fold, wherein at least the outer layer is formed into an expanded shape having a proximal section having a first diameter, a distal section having a second diameter, and a first waist portion having a third diameter, a middle section having a fourth diameter, and a second waist portion having a fifth diameter, wherein the first diameter, the second diameter, and the fourth diameter are each greater than the third diameter, and wherein the first diameter, the second diameter, and the fourth diameter are each greater than the fifth diameter.

Clause 127: In some examples, the apparatus includes clause 126, wherein the proximal section has a first stiffness and the distal section has a second stiffness, the first stiffness greater than the second stiffness.

Clause 128: In some examples, the apparatus includes clause 127, wherein the middle section has a third stiffness, the third stiffness greater than the second stiffness, and wherein the first stiffness is greater than the third stiffness.

Clause 129: In some examples, the apparatus includes any one of clauses 126-128, wherein the proximal section includes a set of filaments each having a diameter greater than filaments in the distal section.

Clause 130: In another example, a method for forming an apparatus for treating an aneurysm in a blood vessel, includes forming a mesh tube, inverting the mesh tube to form an outer layer and an inner layer, the outer layer transitioning to the inner layer at an inversion fold, forming at least the outer layer into an expanded shape having a proximal section having a first diameter and a distal section having a second diameter, and etching the distal section to decrease its stiffness.

Clause 131: In some examples, the method includes clause 130, wherein after the etching step, the distal section has a stiffness less than the stiffness of the proximal section.

Clause 132: In another example, an apparatus for treating an aneurysm in a blood vessel, includes an occlusion element configured to be releasably coupled to an elongate delivery shaft, the occlusion element including an inverted mesh tube having an outer layer and an inner layer, the outer layer transitioning to the inner layer at an inversion fold, the occlusion element configured to be delivered in a collapsed configuration through an inner lumen of a delivery catheter, the inner lumen having a proximal end and a distal end, the occlusion element further configured to expand to an expanded configuration when advanced out of the distal end of the inner lumen of the delivery catheter and into the aneurysm, wherein in the expanded configuration, at least the outer layer of the inverted mesh tube is formed into an expanded shape including a proximal section having a first transverse dimension, a distal section having a second transverse dimension, and a waist portion having a third transverse dimension, wherein the third transverse dimension is less than the first transverse dimension, and the third transverse dimension is less than the second transverse dimension, and wherein in the expanded configuration, the waist portion is configured to be deformed by an externally applied force such that a distance between the distal section and the proximal section is decreased.

Clause 133: In some examples, the apparatus includes clause 132, wherein the waist portion, in a substantially undeformed state, has a longitudinal length of between about 0.05 mm and about 25 mm.

Clause 134: In some examples, the apparatus includes clause 132, wherein the distal section has a length of between about 1 mm and about 25 mm.

Clause 135: In some examples, the apparatus includes clause 132, wherein the distal section has a first longitudinal axis and the proximal section has second longitudinal axis, and wherein in the expanded configuration, the waist portion is configured to be deformed by an externally applied moment such that an angle between the first longitudinal axis and the second longitudinal axis is changed.

Clause 136: In some examples, the apparatus includes clause 135, wherein the angle between the first longitudinal axis and the second longitudinal axis is changeable to a minimum angle of between about 90 degrees and about 135 degrees.

Clause 137: In some examples, the apparatus includes clause 132, wherein the waist portion includes a bellows shape.

Clause 138: In some examples, the apparatus includes clause 132, wherein the waist portion includes a circumferential concavity.

Clause 139: In some examples, the apparatus includes clause 132, wherein the proximal portion includes a proximal diameter A and a distal diameter B, and wherein the distal portion includes a diameter C, and wherein diameter A is between about 50% and about 100% of diameter B.

Clause 140: In some examples, the apparatus includes clause 139, further including a frustoconical portion extending between diameter A and diameter B.

Clause 141: In some examples, the apparatus includes clause 139, wherein diameter A is between about 70% and about 90% of diameter B.

Clause 142: In some examples, the apparatus includes clause 139, wherein diameter C is between about 50% and about 100% of diameter B.

Clause 143: In some examples, the apparatus includes clause 132, wherein the inner layer has an expanded shape which conforms with the expanded shape of the outer layer.

Clause 144: In some examples, the apparatus includes clause 132, wherein the first transverse dimension is about equal to the second transverse dimension.

Clause 145: In some examples, the apparatus includes clause 132, wherein the first transverse dimension is greater than the second transverse dimension.

Clause 146: In some examples, the apparatus includes clause 132, wherein distal section has a substantially hemispherical shape.

Clause 147: In some examples, the apparatus includes clause 132, wherein the proximal section has a substantially hemispherical shape.

Clause 148: In some examples, the apparatus includes clause 147, wherein distal section has a substantially hemispherical shape.

Clause 149: In some examples, the apparatus includes clause 132, wherein the inversion fold is a circular shape surrounding an orifice that communicates with an internal volume of the occlusion element.

Clause 150: In some examples, the apparatus includes clause 132, wherein the distal section has a generally cylindrical shape and a blunt distal end.

Clause 151: In some examples, the apparatus includes clause 132, wherein the distal section has a length that is greater than the second transverse dimension.

Clause 152: In some examples, the apparatus includes clause 132, wherein the inverted mesh tube is formed from a plurality of filaments.

Clause 153: In some examples, the apparatus includes clause 152, wherein at least some filaments of the plurality of filaments, at the outer layer at the distal section, have an etched surface.

Clause 154: In some examples, the apparatus includes clause 152, wherein between about 50 percent and about 100 percent of the plurality of filaments include drawn filled tubes.

Clause 155: In some examples, the apparatus includes clause 154, wherein at least some of the drawn filled tubes includes a radiopaque core having a cross-sectional area that is between about 51% and about 70% of the total cross-sectional area.

Clause 156: In some examples, the apparatus includes clause 132, further including a pusher having a proximal end and a distal end, wherein the occlusion element is configured to be releasably coupled to the distal end of the pusher at a releasable joint.

Clause 157: In some examples, the apparatus includes clause 156, further including a connection tube having a proximal end substantially flush with a proximal end of the occlusion element, a distal end extending within the occlusion element, and a lumen, wherein the distal end of the pusher extends through the lumen of the connection tube and includes a plurality of radially extending protrusions located distal to the distal end of the connection tube, the plurality of radially extending protrusions forming a maximum transverse dimension that is greater than a maximum diameter of the lumen of the connection tube.

Clause 158: In some examples, the apparatus includes clause 157, further including an activator configured to modify the plurality of radially extending protrusions such that the distal end of the pusher can be fully removed from the lumen of the connection tube.

Clause 159: In some examples, the apparatus includes clause 158, wherein the activator is configured to cause an effect to the radially extending protrusions selected from the list consisting of: melting, detaching, unbending, breaking, ablating, and deforming.

Clause 160: In some examples, the apparatus includes clause 132, wherein the waist portion includes a circumferential convexity.

Clause 161: In some examples, the apparatus includes clause 160, further including a first circumferential concavity adjacent a first end of the circumferential convexity and a second circumferential concavity adjacent a second end of the circumferential convexity.

Aneurysms are often non-spherical in shape and may also or alternatively have mild to severe angulations in relation to the vessel or vessels from which they bulge or protrude. This may make the delivery and employment of one or more aneurysm embolization device to the aneurysm a technical and physical challenge. Systems are presented herein to remedy the difficulties that may occur.

Figure 69:
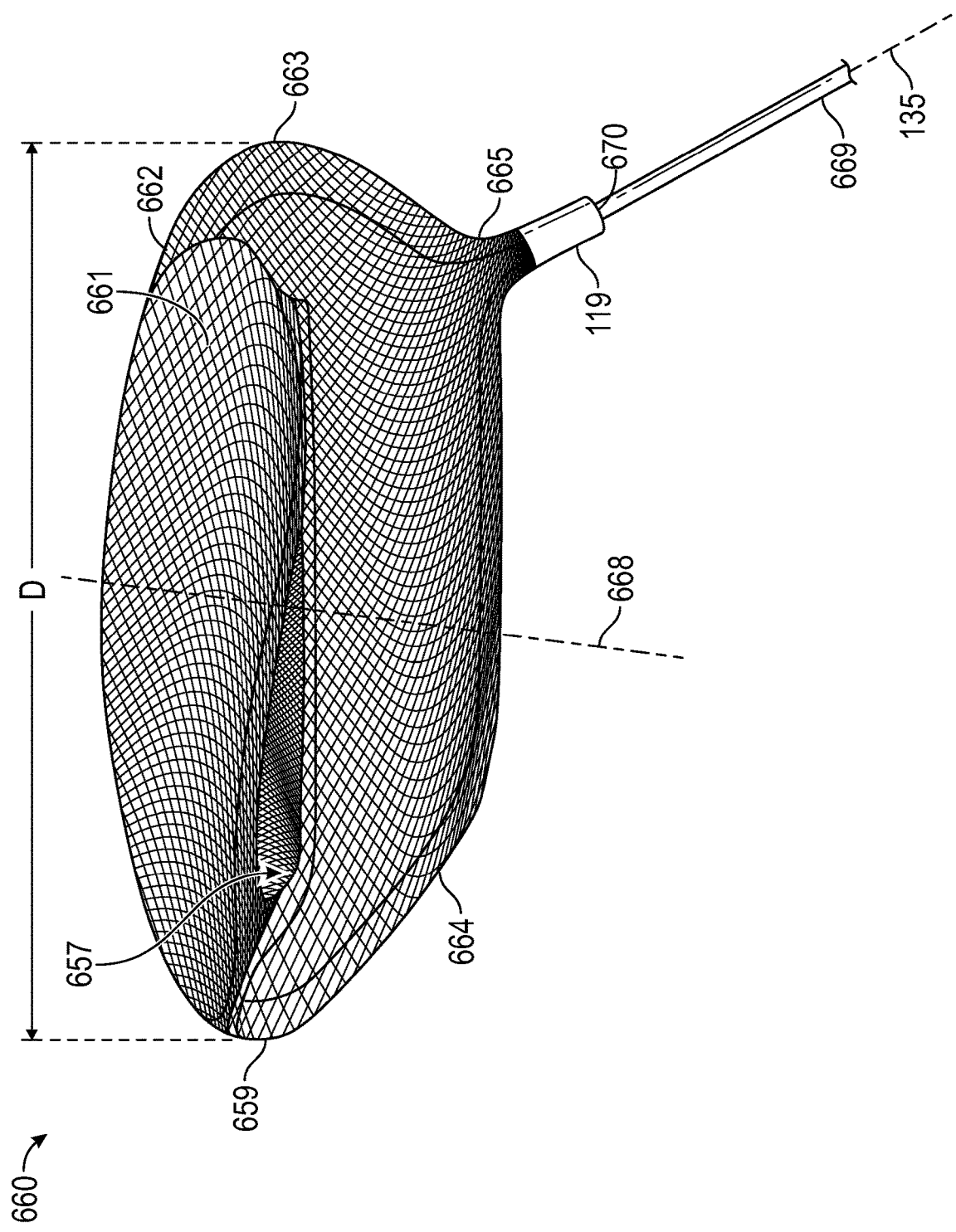
FIG. 69 is a perspective view of an occlusion device according to an embodiment of the present disclosure.

FIG. 69 illustrates an occlusion device 660 configured for placement within an aneurysm. The occlusion device 660 comprises a cover 663 having an outer diameter D. In some embodiments, the cover 663 is circular, with substantially the same diameter D at any transverse measurement around the perimeter. In other embodiments, the cover 663 is non-circular, and may comprise an ellipse, an oval, a polygon or other shapes. In the non-circular embodiments, the cover 663 comprises a minimum transverse dimension and a maximum transverse dimension. In the particular case of an ellipse or an oval shape, the cover 663 comprises a major diameter and a minor diameter. The minor diameter or minimum transverse dimension is configured to be larger than a maximum transverse dimension of an opening into the aneurysm (the neck portion). Thus, the cover 663 is configured to completely cover the neck portion, and thus to cause stagnation of blood within the aneurysm, leading to occlusion. The cover 663 is constructed from a mesh (braided) Nitinol (nickel-titanium alloy) tube 665 that is inverted on itself, thus providing an outer facing surface 664 and an inner facing surface 661. The mesh tube 665 is heat-formed such that cover 663 comprises an expanded portion and a first end 675 and a second end 674 of the tube 665 (FIG. 2) each comprise unexpanded (or partially expanded) portions. A smooth fold 662 extends around the circumference 659 of the cover 663 and represents the transition between the outer facing surface 664 and the inner facing surface 661. The fold 662 avoids any sharp edge that might risk rupture of an aneurysm wall, or other anatomical damage. The cover 663 includes a concavity 657 arranged around a longitudinal axis 668. The cover 663 is fabricated as an inverted mesh tube 665 having a simple straight elongate configuration, and is subsequently formed into the shape shown in FIG. 69, and heat set into this shape. For example, the inverted mesh tube 665 may be constructed as a single layer mesh tube formed of at least some nickel-titanium alloy filaments, and then inverted on itself. The inverted mesh tube 665 may then be placed into a die or mold comprising one or more pieces, to hold it in the shape of the cover 663. Then, the cover 663 may be subjected to an elevated temperature and then cooled, to lock in the shape, resulting in a cover 663 having at least some superelastic properties.

As formed (e.g., heat-formed), the cover 663 has an expanded configuration (shown in FIG. 69) and a collapsed configuration, shown in FIG. 71. The cover 663 comprises two mesh layers, provided by the outer facing surface 664 and the inner facing surface 661.

In some embodiments, the cover 663 may comprise some nickel-titanium alloy filaments and some radiopaque elements, comprising platinum, gold, tantalum, or alloys of any of these or other radiopaque materials. In some embodiments, the filaments may comprise drawn filled tubes (DFT), such as those comprising a nickel-titanium alloy outer wall and a platinum core. The radiopaque material allows the cover 663 to be visible on radiographs or fluoroscopy. The occlusion device 660 may be configured by controlling how much radiopaque material is used, by either the ratio of radiopaque filaments to non-radiopaque filaments, or by the amount of platinum core in the drawn filled tubes. In this manner, the cover 663 can be selectively fabricated to be sufficiently visible, but not over visible, e.g., overly bright, such that other objects are obscured. In some embodiments, whether any of the filaments comprise radiopaque materials or not, a marker band 119 may be attached to the proximal end 672 of the occlusion device 660, by adhesive or epoxy bonding, or swaging, welding or other mechanical attachment.

A pusher 669, having a distal end 673 and a proximal end 667, may comprise a wire, a hypo tube, or another elongate structure having column support is detachably coupled at its distal end 673 to the proximal end 672 of the occlusion device 660. A detachable joint 670 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. During delivery, the pusher 669 is held on its proximal end 667 by a user and pushed in a forward longitudinal direction 676 (FIGS. 71-72), in order to advance the occlusion device 660 to the distal end 679 of a delivery catheter 677 (e.g., a microcatheter) having a delivery lumen 678. The delivery catheter 677 may also include a proximal hub 137, such as a luer connector.

In the embodiment of FIG. 70, the pusher 669 comprises an outer tube 153 and an inner wire 151 coupled to each other. Conductors (e.g., electrical wires) 147, 149 are electrically coupled distally to the inner wire 151 and outer tube 153 (e.g., if a metallic tube), and proximally to first and second circumferential contacts 143, 145 which are carried on a hub 141 that is attached to the proximal end 667 of the pusher 669. The hub 141 has a cavity 671 into which the proximal end 667 of the pusher 669 is inserted and bonded. The hub 141 and its circumferential contacts 143, 145 is reversibly couplable to a connector (not shown) of a detachment controller (not shown), such as those known in the art. The detachment of the occlusion device 660 from the pusher 669 may be achieved by use of the detachment controller by any of the detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems.

Figure 73:
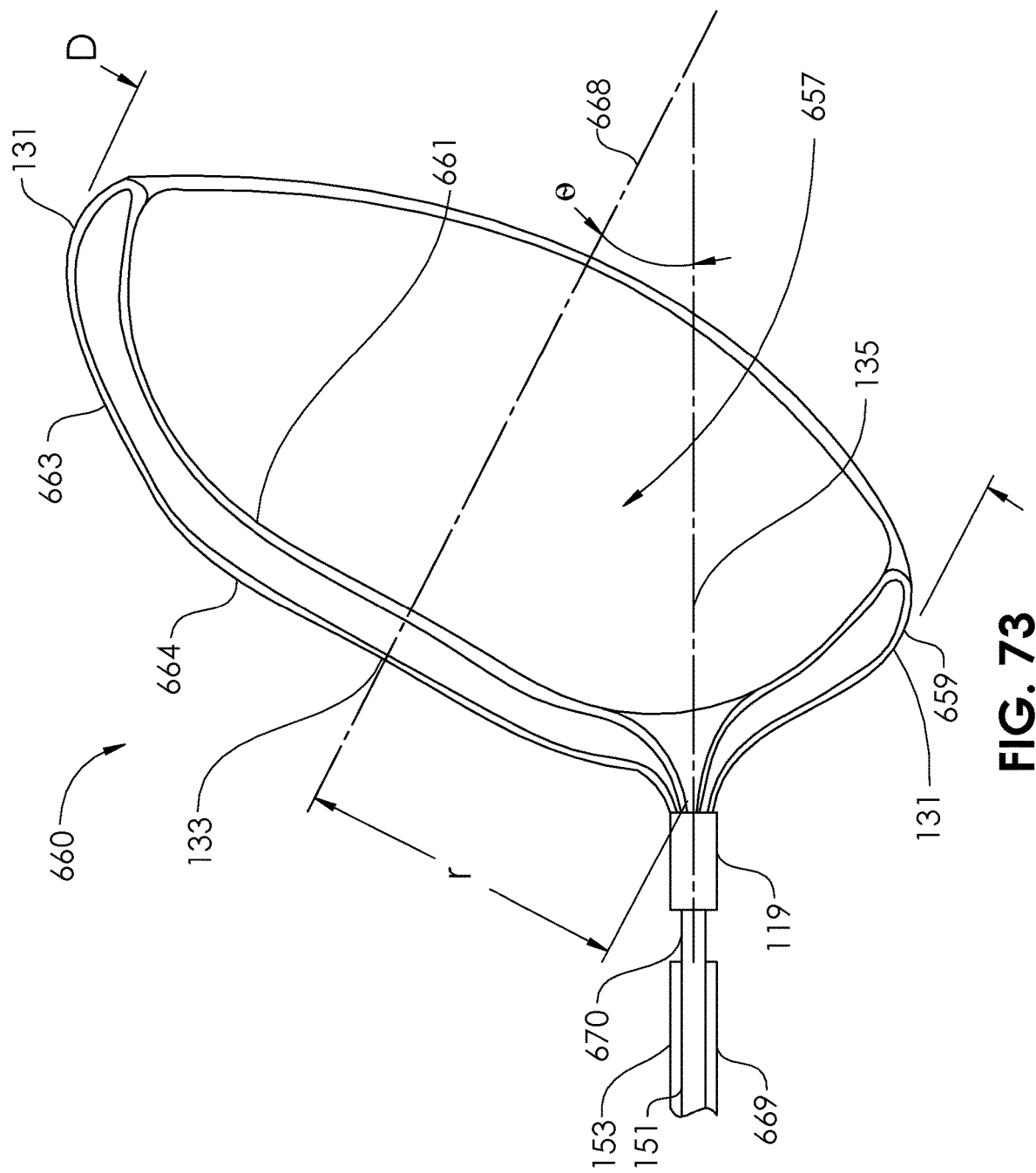
FIG. 73 is a detail sectional view of a distal end of the occlusion device of FIG. 70.

Turning to FIG. 73, the cover 663 of the occlusion device 660 in its expanded configuration includes a concavity 657 arranged generally around a longitudinal axis 668. This does not require that the longitudinal axis 668 be a complete axis of symmetry, as the cover may or may be an elliptical shape, or another non-circular shape. The pusher 669 extends from the detachable joint 670 along its own longitudinal axis 135 that is not colinear with the longitudinal axis 668. A non-zero angle θ is thus formed between the two longitudinal axes 668, 135. The angle θ may be between about 15 degrees and about 120 degrees, or between about 30 degrees and about 120 degrees, or between about 40 degrees and about 100 degrees, or between about 45 degrees and about 90 degrees, or between about 75 degrees and about 90 degrees. This angulation aids in the delivery of the occlusion device 660 to an aneurysm that has an angulated takeoff and/or that is located along a tortuous artery or an artery having a severe bend, as will be shown in FIGS. 74A-76C.

Furthermore, the outer facing surface 664 has a general center point 133 at the longitudinal axis 668. The center point 133 (and longitudinal axis 668) are separated from the detachable joint 670 by a non-zero distance r. Thus, the detachable joint 670 is radially offset from the longitudinal axis 668. The maximum radius $r_{MAX}$ of the cover 663 is the largest radius measured from the longitudinal axis 668 to the circumference 131, for example, at any point on the circumference 131 on a generally circular cover, or at a point along the circumference 131 (or in general, perimeter) that is along a major axis, as in an ellipse. The phrase "radially offset," when used herein, should be interpreted as meaning at least about 5% radially offset. In some embodiments, the distance r is at least about 10% of the maximum radius $r_{MAX}$, at least about 25% of the maximum radius $r_{MAX}$, or at least about 50% of the maximum radius, or at least about 75% of the maximum radius $r_{MAX}$. The offset (distance r) aids in the delivery of the occlusion device 660 to an aneurysm that has an angulated takeoff and/or that is located along a tortuous artery or an artery having a severe bend, as will be shown in FIGS. 74A-76C.

Figure 77:
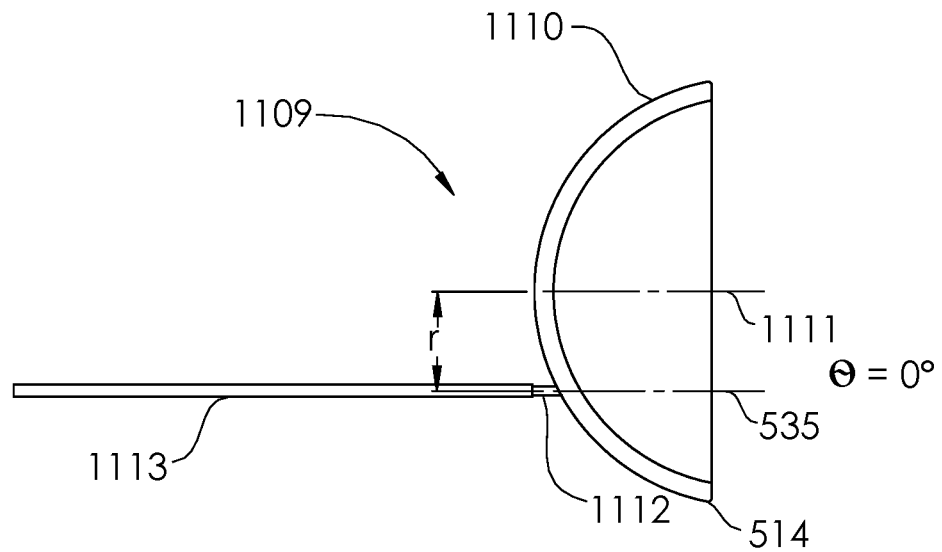
FIG. 77 is a plan view of an occlusion device according to an embodiment of the present disclosure.
Figure 78:
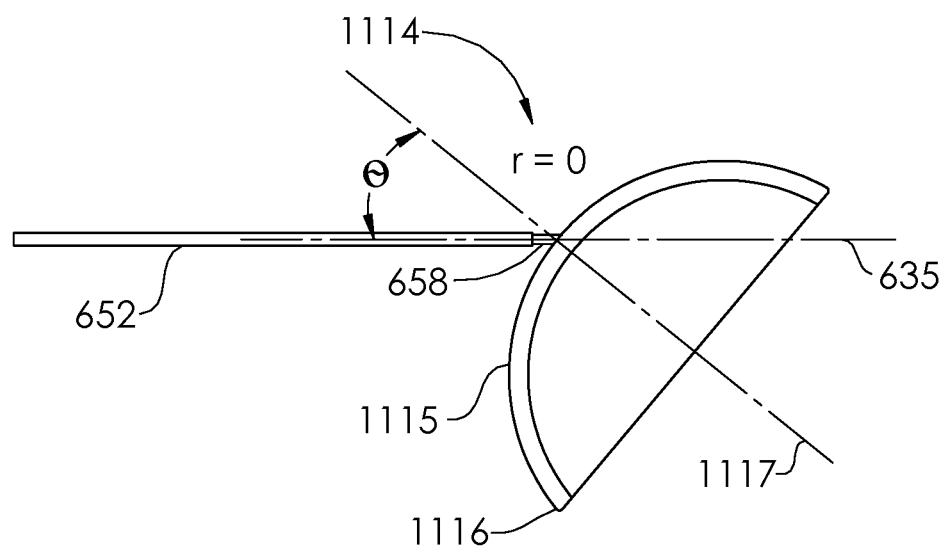
FIG. 78 is a plan view of an occlusion device according to an embodiment of the present disclosure.

Although in FIG. 73 there is both a non-zero angle θ and a non-zero distance r, in other embodiments, there may be a non-zero angle θ but a substantially zero distance r, as in the occlusion device 1114 of FIG. 78. In other embodiments, there may be a non-zero distance r and a substantially zero degree angle θ, as in the occlusion device 1109 of FIG. 77.

FIGS. 74A-76C illustrate arteries 681, 802, 902 having sidewall aneurysms 680, 800, 900. The approach by catheter (e.g., delivery catheter/microcatheter 685) in a sidewall aneurysm is often challenging when placing a single occlusion device. A distal end 686 of the delivery catheter 685 may be supplied preshaped with a particular curve, or may be steam shaped or shaped by other manners by a user, to create a preferred curve, prior to the insertion of the delivery catheter 685 into the patient's vasculature, such that the delivery angle of occlusion devices 687, 692, 698 into the aneurysm 680, 800, 900 allows a delivery along an axis that is substantially or somewhat parallel to a longitudinal axis of the neck 683, 806, 906 of the aneurysm 680, 800, 900, or substantially or somewhat parallel to a longitudinal axis of the sac of the aneurysm 680, 800, 900 itself. However, the curvature of the artery 681, 802, 902 or a small diameter of the artery 681, 802, 902 may make it difficult for a curved tip of a delivery catheter 685 to fit in the artery 681, 802, 902, adjacent the neck 683, 806, 906. In other cases, the curved tip may not be able to provide sufficient backup support for delivering the implant (occlusion device). Occlusion devices 687, 692, 698 according to the embodiments disclosed herein ameliorate the efficacy of embolizations performed in these anatomical conditions by allowing the user to choose particular device parameters that match the anatomy.

In FIG. 74A an occlusion device 687 comprising a cover 688 detachably coupled to a pusher 691 at a detachable joint 1103 is delivered through a delivery catheter 685 to an aneurysm 680 extending from an artery 681. The aneurysm 680 includes a dome 682 and a neck 683. The occlusion device 687 is similar to the occlusion device 660, but has a different angle θ and offset distance r, as seen in FIG. 74A. The particular occlusion device 687 (e.g., size, specification, model) may be chosen by the attending physician to fit the aneurysm 680, with the angle θ and offset distance r particularly chosen to aid the delivery through the artery 681 and into the aneurysm 680, and to optimize the geometry of the system (e.g. delivery catheter 685 and occlusion device 687) during detachment. The cover 688 has a concavity 690 and an outer perimeter 1104, or circumference (FIG. 74C). In FIG. 74B, the cover 688 is detached from the pusher 691 via the detachable joint 1103 in any one of the manners described in relation to the occlusion device 660. The pusher 691 and the delivery catheter 685 are then removed from the patient, leaving the occlusion device 687 deployed within the aneurysm 680, as shown in FIG. 74C. The outer facing surface 689 of the cover 688 is seated against a lower wall portion 708 of the aneurysm 680 sac, against the neck 683 of the aneurysm 680. The outer perimeter 1104 extends into the sac, at least at some of its portions, and extends in a direction substantially away from the neck 683 of the aneurysm 680.

In FIG. 75A an occlusion device 692 comprising a cover 693 detachably coupled to a pusher 696 at a detachable joint 695 is delivered through a delivery catheter 685 to an aneurysm 800 extending from an artery 802. The aneurysm 800 includes a dome 804 and a neck 806. The occlusion device 692 is similar to the occlusion device 660, but has a different angle θ and offset distance r, as seen in FIG. 75A. The particular occlusion device 692 (e.g., size, specification, model) may be chosen by the attending physician to fit the aneurysm 800, with the angle θ and offset distance r particularly chosen to aid the delivery through the artery 802 and into the aneurysm 800, and to optimize the geometry of the system (e.g. delivery catheter 685 and occlusion device 692) during detachment. The cover 693 has a concavity 697 and an outer perimeter 1106, or circumference (FIG. 75C). In FIG. 75B, the cover 693 is detached from the pusher 696 via the detachable joint 695 in any one of the manners described in relation to the occlusion device 660. The pusher 696 and the delivery catheter 685 are then removed from the patient, leaving the occlusion device 692 deployed within the aneurysm 800, as shown in FIG. 75C. The outer facing surface 694 of the cover 693 is seated against a lower wall portion 808 of the aneurysm 800 sac, against the neck 806 of the aneurysm 800. The outer perimeter 1106 extends into the sac, at least at some of its portions, and extends in a direction substantially away from the neck 806 of the aneurysm 800.

In FIG. 76A an occlusion device 698 comprising a cover 699 detachably coupled to a pusher 1101 at a detachable joint 1102 is delivered through a delivery catheter 685 to an aneurysm 900 extending from an artery 902. The aneurysm 900 includes a dome 904 and a neck 906. The occlusion device 698 is similar to the occlusion device 660, but has a different angle θ and offset distance r, as seen in FIG. 76A. The particular occlusion device 698 (e.g., size, specification, model) may be chosen by the attending physician to fit the aneurysm 900, with the angle θ and offset distance r particularly chosen to aid the delivery through the artery 902 and into the aneurysm 900, and to optimize the geometry of the system (e.g. delivery catheter 685 and occlusion device 698) during detachment. The cover 699 has a concavity 1100 and an outer perimeter 1108, or circumference (FIG. 76C). In FIG. 76B, the cover 699 is detached from the pusher 1101 via the detachable joint 1102 in any one of the manners described in relation to the occlusion device 660. The pusher 1101 and the delivery catheter 685 are then removed from the patient, leaving the occlusion device 698 deployed within the aneurysm 900, as shown in FIG. 76C. The outer facing surface 408 of the cover 699 is seated against a lower wall portion 908 of the aneurysm 900 sac, against the neck 906 of the aneurysm 900. The outer perimeter 1108 extends into the sac, at least at some of its portions, and extends in a direction substantially away from the neck 906 of the aneurysm 900.

Figure 74:
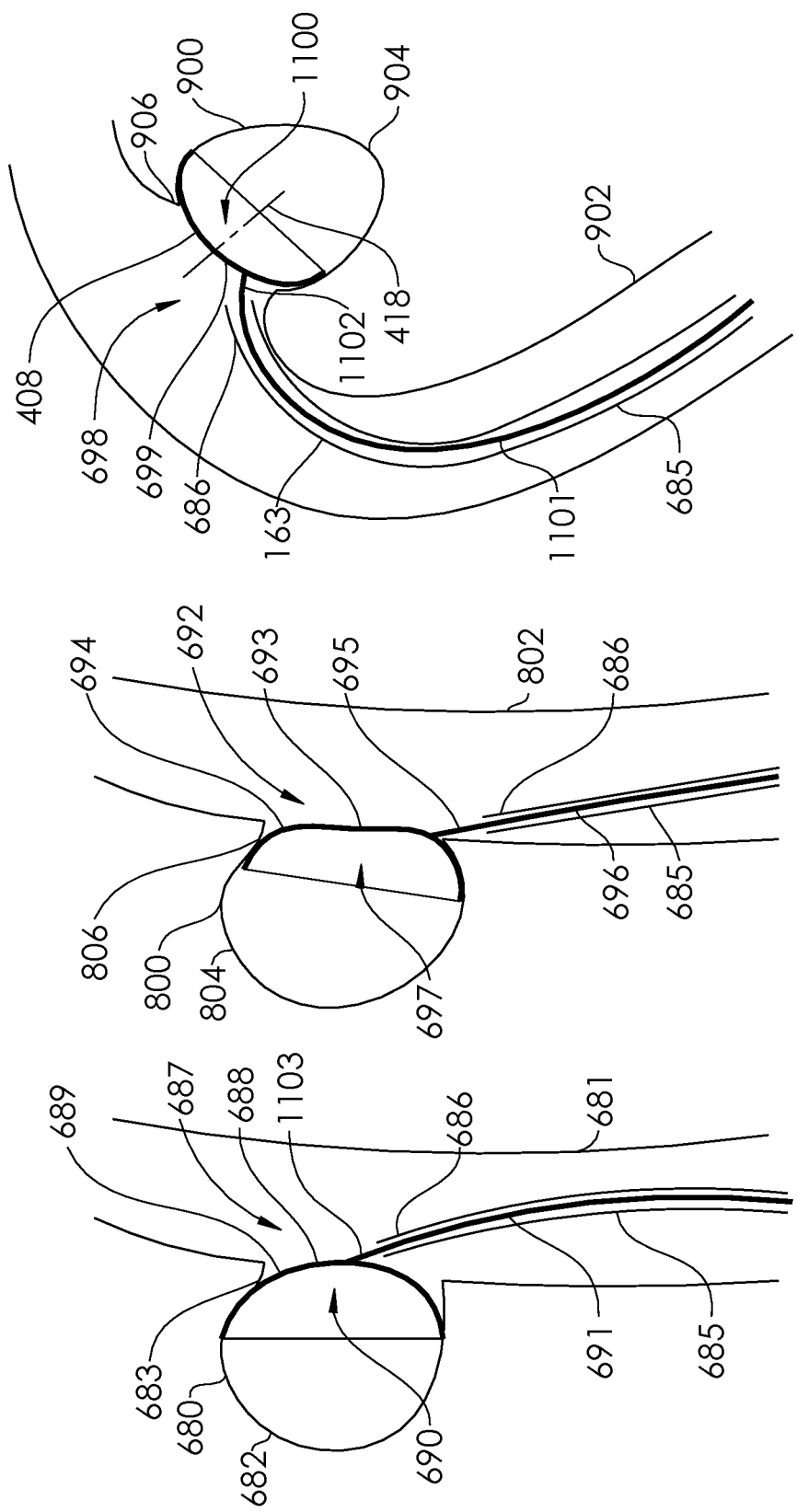
FIGS. 74A-74C are sectional views of the delivery of an occlusion device of an occlusion system into an aneurysm according to an embodiment of the present disclosure.
Figure 75:
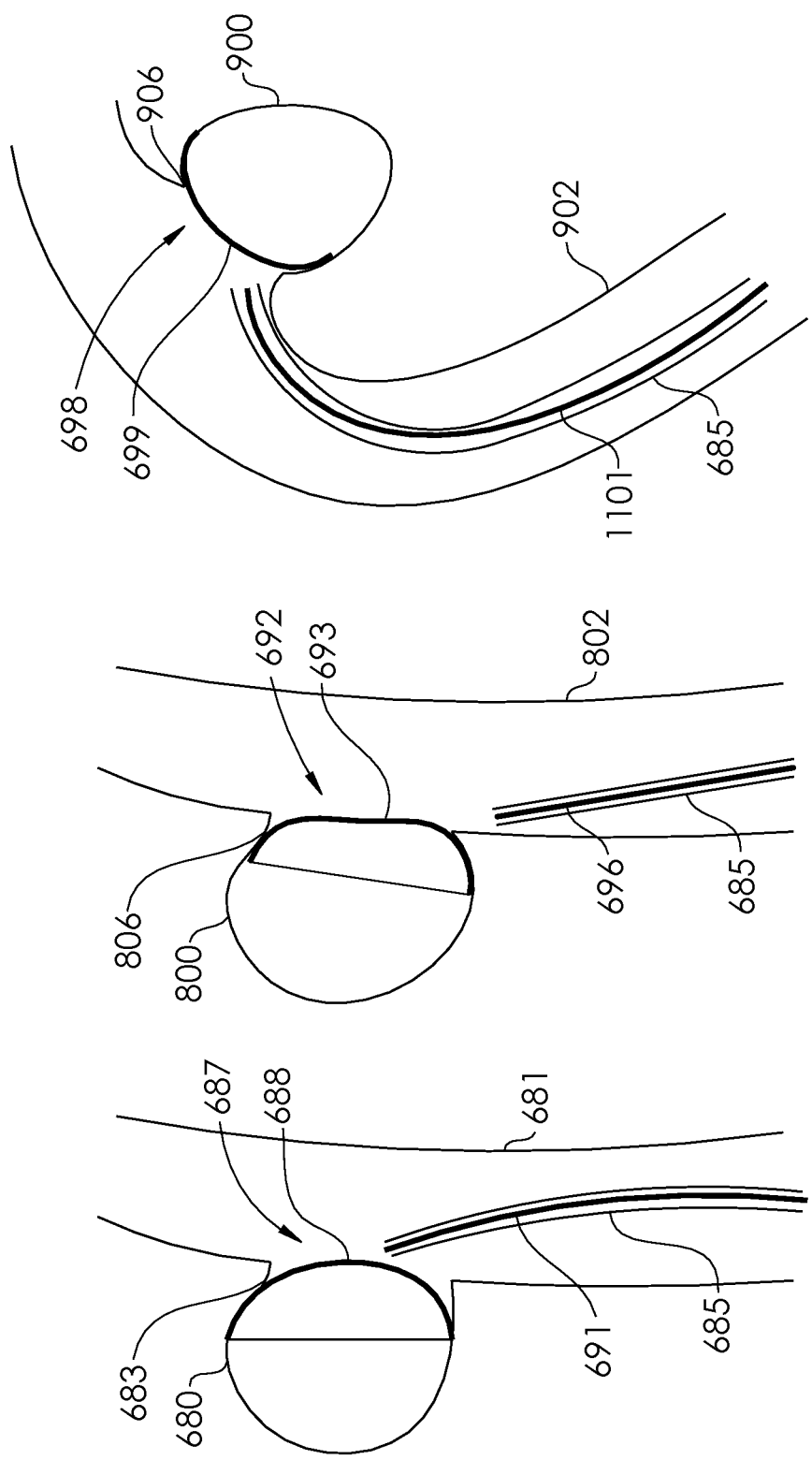
FIGS. 75A-75C are sectional views of the delivery of an occlusion device of an occlusion system into an aneurysm according to an embodiment of the present disclosure.
Figure 76:
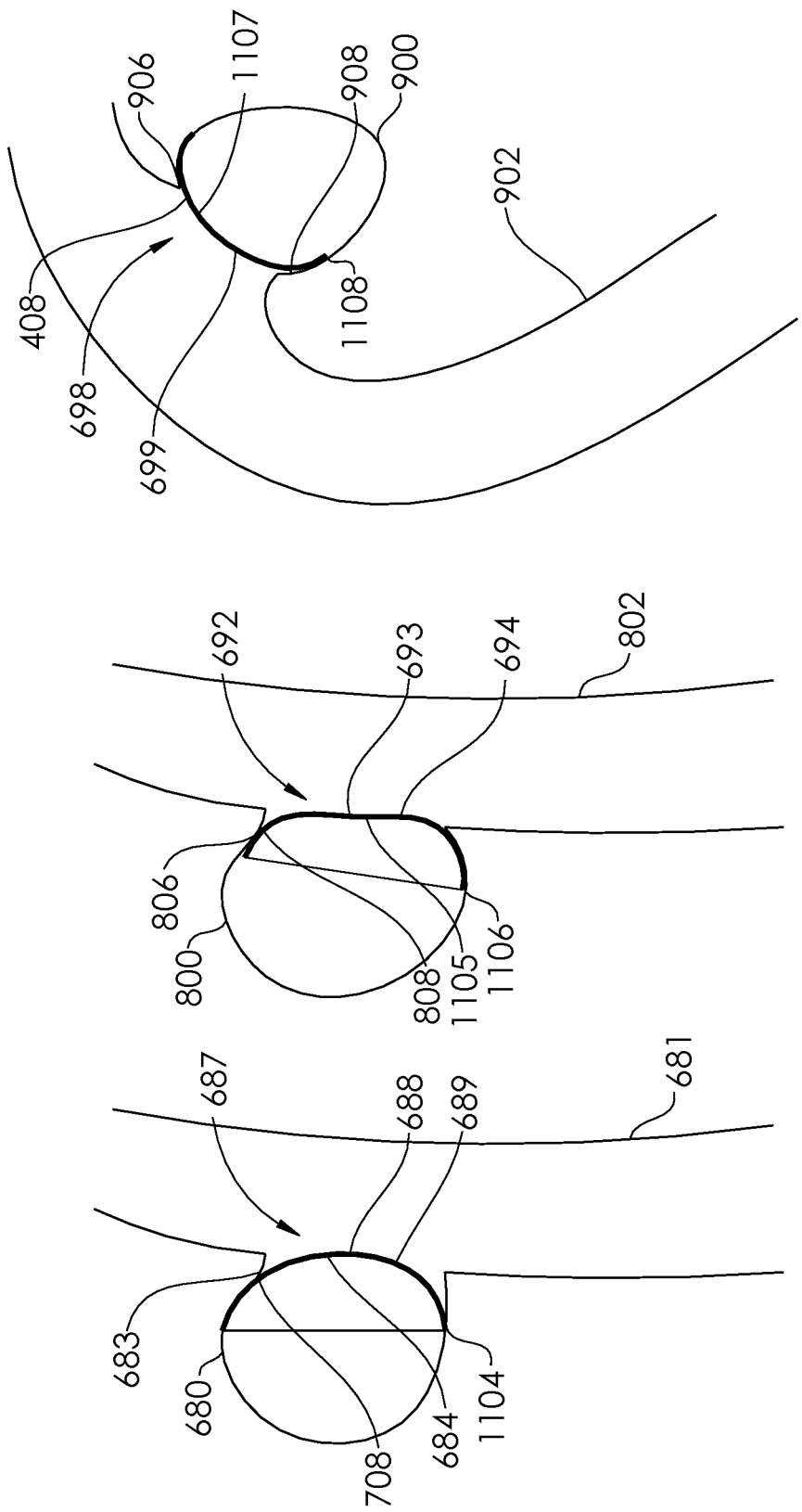
FIGS. 76A-76C are sectional views of the delivery of an occlusion device of an occlusion system into an aneurysm according to an embodiment of the present disclosure.

As can be seen in FIGS. 74A-76C, the particular angle θ and/or offset distance r make possible optimized delivery and deployment of the occlusion devices 687, 692, 698 within the aneurysms 680, 800, 900. In FIGS. 74A and 75A, the delivery catheter 685 is shown having little or no curve formed onto its distal end 686. However, in FIG. 76A, the distal end 686 has a curve 163 preformed or physician-formed, to aid the delivery of the occlusion device 698 into the aneurysm 900. The curve 163 is more or less oriented along the plane of the page, with radius or radii or curvature that are substantially orthogonal to the page (i.e., extend vertically from the page). However, because the occlusion device 698 has a concave shape arrange around a longitudinal axis 418, and because the occlusion device 698 and pusher 1101 together form a structure that is asymmetric to the longitudinal axis 418, it may be desirable to selectively control the oriental rotation of the occlusion device 698 in relation to its longitudinal axis 418, which would thus further control the overall orientation of the occlusion device 698 in relation to the aneurysm 900.

Returning to FIG. 69, the cover 663 may be braided such that the braiding, mesh, etc., is arranged somewhat symmetrically around the longitudinal axis 668. However, it may also be desired in alternative embodiments to asymmetrically form the braiding around the longitudinal axis 668, such that when the cover 663 is compressed into its collapsed configuration, it actually preferentially favors (via structure and sliding mechanics) forming a more linear structure, oriented more along the longitudinal axis 135 (FIG. 73). Thus, while compressed within the lumen 678 of the delivery catheter 677, the longitudinal axis 668 and the "pseudo" longitudinal axis 135 (because the cover 663 is now temporarily deformed) are now forced into an angle θ of substantially 90 degrees (in relation to each other). That is, until the cover 663 is delivered from the lumen 678 of the delivery catheter 677, allowing it to take its expanded configuration, and, via the memory of the braid material, to conform to its true angle θ. The asymmetric braiding may be achieved by using a braiding process or automated braiding machine that varies the braid angle in an oscillating or sinusoidal manner. For example, at a particular clock location around the circumference 659 of the cover 663 (e.g., 6 o'clock) the braid angle may equal a first value X and at another clock location around the circumference 659 of the cover 663 (e.g., 9 o'clock) the braid angle may equal a second value 0.8x. In some embodiments, the second value may be between about 40% and about 95% of the first value, or between about 50% and about 90% of the first value, or between about 60% and about 85% of the first value.

FIG. 77 illustrates an occlusion device 1109 comprising a cover 1110 detachably coupled to a pusher 1113 at a detachable joint 1112. The cover 1110 has an outer perimeter 514. The longitudinal axis 1111 of the cover 1110 is radially offset from the longitudinal axis 535 of the pusher 1113 by a non-zero distance r. There is substantially a zero angle between the longitudinal axis 1111 of the cover and the longitudinal axis 535 of the pusher 1113.

FIG. 78 illustrates an occlusion device 1114 comprising a cover 1115 detachably coupled to a pusher 652 at a detachable joint 658. The cover 1115 has an outer perimeter 1116. The longitudinal axis 1117 of the cover 1115 is angled from the longitudinal axis 635 of the pusher 652 by a non-zero angle θ. There is substantially a zero distance r between the longitudinal axis 1117 of the cover 1115 and the longitudinal axis 635 of the pusher 652.

Though the occlusion devices 660, 687, 692, 698, 1109, 1114 as described according to embodiments disclosed herein are shown generally having a proximal convexity and a distal concavity, and are configured to predominantly being placed in a lower (near the neck) portion of an aneurysm, any other configuration for an aneurysm occlusion device is also contemplated for use in combination with the attachment/detachment geometries taught in the embodiments disclosed. This includes devices configured to be the only device implanted in the aneurysm, as well as devices configured to be one or a plurality of devices implanted in the aneurysm. FIGS. 79-84 illustrate six different occlusion systems 770, 772, 774, 776, 778, 780 being utilized to deliver a braided shell 758 into an aneurysm 750 having a dome 752 and a neck 768. The braided shell 758 has a longitudinal axis 756 and is configured to fill a majority of the aneurysm 750 or in some cases substantially all of the aneurysm 750 sac. The braided shell 758 is braided or woven from filaments 760, and has a proximal end 751, a distal end 753, and an intermediate portion 782. The aneurysm 750 has the geometry of a sidewall aneurysm in relation to left extending artery 762 and right extending artery 764. The aneurysm 750 alternatively has the geometry of a terminal aneurysm in relation to artery 754. An additional vessel 766 may also be present. It may be desired to avoid the embolization of this vessel 766 in the process of embolizing the aneurysm 750.

Figure 79:
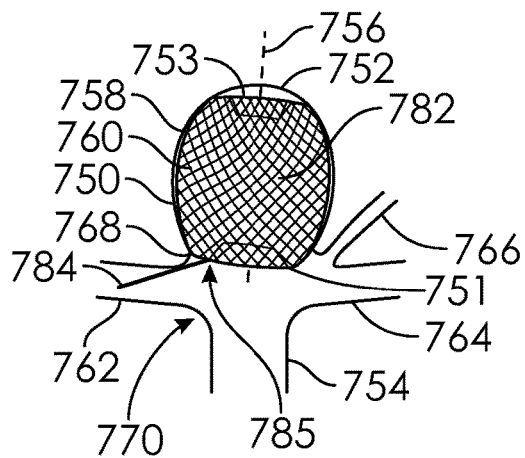
FIG. 79 is a perspective view of the delivery of an occlusion device of an occlusion system into an aneurysm according to an embodiment of the present disclosure.

In FIG. 79, the occlusion system 770 includes a pusher 784 that is detachably coupled to the proximal end 751 of the braided shell 758 at a detachable joint 785. The pusher 784 extends from the detachable joint 785 at a non-zero angle in relation to the longitudinal axis 756 of the braided shell 758. The detachable joint 785 is dimensionally offset a non-zero distance from the longitudinal axis 756 of the braided shell 758. The offset side is the same as the side that the pusher 784 extends. The occlusion system 770 is shown in FIG. 79 being delivered from the artery 762, though it may also be delivered from one or more other arteries.

Figure 80:
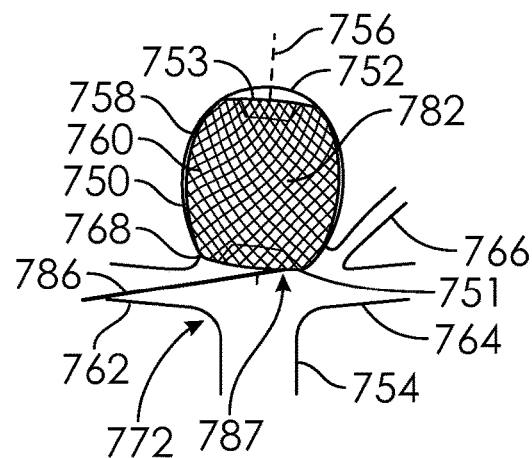
FIG. 80 is a perspective view of the delivery of an occlusion device of an occlusion system into an aneurysm according to an embodiment of the present disclosure.

In FIG. 80, the occlusion system 772 includes a pusher 786 that is detachably coupled to the proximal end 751 of the braided shell 758 at a detachable joint 787. The pusher 786 extends from the detachable joint 787 at a non-zero angle in relation to the longitudinal axis 756 of the braided shell 758. The detachable joint 787 is dimensionally offset a non-zero distance from the longitudinal axis 756 of the braided shell 758, which is located on an opposite side of the longitudinal axis from the side that the pusher 784 extends. The occlusion system 772 is shown in FIG. 80 being delivered from the artery 762, though it may also be delivered from one or more other arteries.

Figure 81:
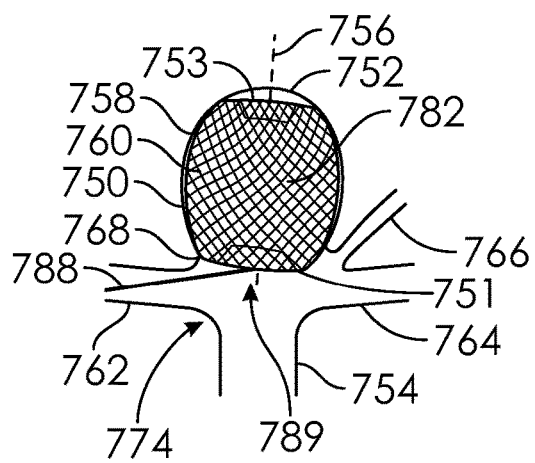
FIG. 81 is a perspective view of the delivery of an occlusion device of an occlusion system into an aneurysm according to an embodiment of the present disclosure.

In FIG. 81, the occlusion system 774 includes a pusher 788 that is detachably coupled to the proximal end 751 of the braided shell 758 at a detachable joint 789. The pusher 788 extends from the detachable joint 789 at a non-zero angle in relation to the longitudinal axis 756 of the braided shell 758. The detachable joint 789 is generally not offset from the longitudinal axis 756 of the braided shell 758, but is instead coupled substantially at the longitudinal axis 756. The occlusion system 774 is shown in FIG. 81 being delivered from the artery 762, though it may also be delivered from one or more other arteries.

Figure 82:
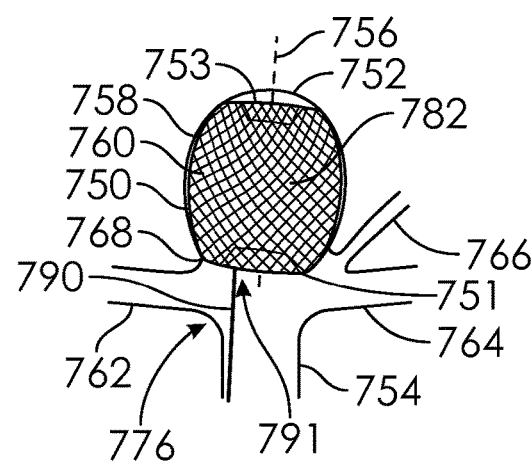
FIG. 82 is a perspective view of the delivery of an occlusion device of an occlusion system into an aneurysm according to an embodiment of the present disclosure.

In FIG. 82, the occlusion system 776 includes a pusher 790 that is detachably coupled to the proximal end 751 of the braided shell 758 at a detachable joint 791. The pusher 790 extends from the detachable joint 791 at a substantially zero angle in relation to the longitudinal axis 756 of the braided shell 758. The detachable joint 791 is dimensionally offset a non-zero distance from the longitudinal axis 756 of the braided shell 758. The occlusion system 776 is shown in FIG. 82 being delivered from the artery 754, though it may also be delivered from one or more other arteries.

Figure 83:
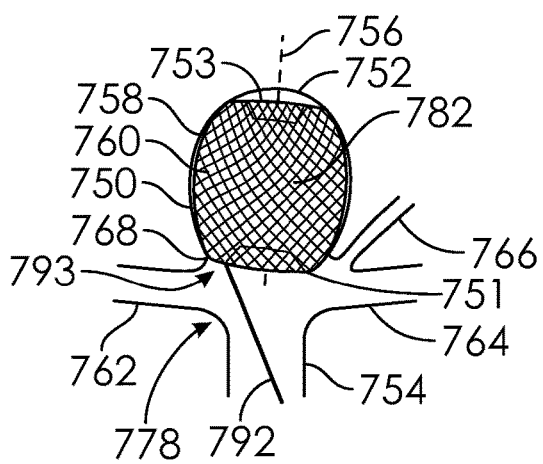
FIG. 83 is a perspective view of the delivery of an occlusion device of an occlusion system into an aneurysm according to an embodiment of the present disclosure.

In FIG. 83, the occlusion system 778 includes a pusher 792 that is detachably coupled to the proximal end 751 of the braided shell 758 at a detachable joint 793. The pusher 792 extends from the detachable joint 793 at a non-zero angle in relation to the longitudinal axis 756 of the braided shell 758. The detachable joint 793 is dimensionally offset a non-zero distance from the longitudinal axis 756 of the braided shell 758. The offset side is opposite of the side that the pusher 792 extends. The occlusion system 778 is shown in FIG. 83 being delivered from the artery 754, though it may also be delivered from one or more other arteries.

Figure 84:
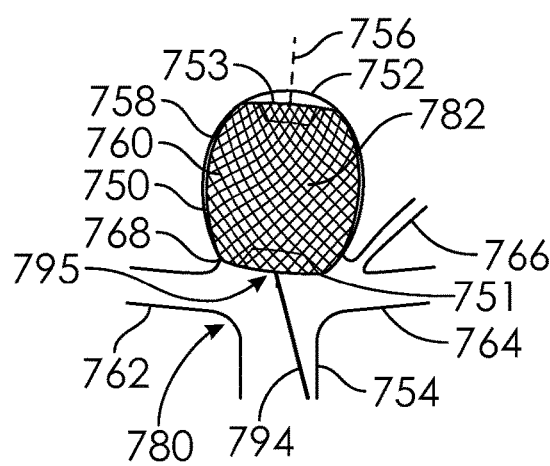
FIG. 84 is a perspective view of the delivery of an occlusion device of an occlusion system into an aneurysm according to an embodiment of the present disclosure.

In FIG. 84, the occlusion system 780 includes a pusher 794 that is detachably coupled to the proximal end 751 of the braided shell 758 at a detachable joint 795. The pusher 794 extends from the detachable joint 795 at a non-zero angle in relation to the longitudinal axis 756 of the braided shell 758. The detachable joint 795 is not offset from the longitudinal axis 756 of the braided shell 758, but is instead coupled substantially at the longitudinal axis 756. The occlusion system 780 is shown in FIG. 84 being delivered from the artery 754, though it may also be delivered from one or more other arteries.

As can be seen in FIGS. 79-84, the angle θ and/or offset distance r make possible optimized delivery and deployment of the occlusion devices (braided shell 758) within the aneurysm 750.

Figure 85:
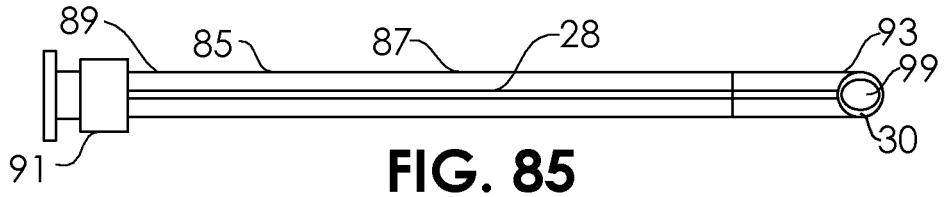
FIG. 85 is a top view of a delivery catheter according to an embodiment of the present disclosure.
Figure 86:
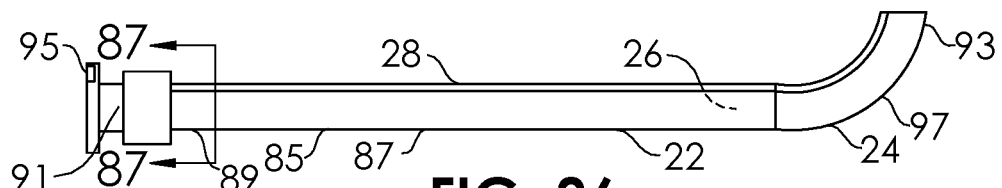
FIG. 86 is a side view of the delivery catheter of FIG. 85.
Figure 87:
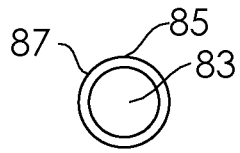
FIG. 87 is a magnified cross-section view taken along line 87 of FIG. 86.

FIGS. 85 and 86 illustrate a delivery catheter 85 comprising a shaft 87 having a proximal end 89, a distal end 93 having a curve 97, and a non-circular lumen 99. A luer hub 91 is bonded to the proximal end 89 of the shaft 87. In some embodiments, the non-circular lumen 99 may extend through the entirety of the shaft 87, but in the embodiment of FIGS. 85 and 86, the non-circular lumen 99 morphs into a circular lumen 83 (FIG. 87) at the proximal end 89. In some embodiments, the shaft 87 may be extruded with a circular lumen 83 its entire length, and then a non-circular cross-section mandrel may be placed in the lumen 83 at the distal end 93, and heat may be applied to reform the lumen 83 at the distal end 93 to have the non-circular lumen 99 shape. In other embodiments, a first tubular portion 22 having a circular lumen 83 may be thermally fused to a second tubular portion 24 having a non-circular lumen 99. The mandrel may be placed from the proximal end, and have smooth transitions between a circular outer cross-section and a non-circular outer cross-section, in order to form a transition zone 26 comprising a continuously smooth luminal wall surface transition between the circular lumen 83 and the non-circular lumen 99. The non-circular lumen 99 is illustrated in FIG. 85 as an ellipse, buy may alternately by an oval, or any type of non-circular cross-sectional shape. For example, a polygonal shape, a dogbone shape, a guitar shape, or a U-shape. Optionally, to further aid visualization on fluoroscopy (e.g., biplane fluoroscopy), a radiopaque stripe 28 may be extruded or otherwise placed on one side of the wall 30 of the shaft 87. Thus, a physician delivering the delivery catheter 85 is able to better judge the orientation (the clock position of rotation) of the curve 97 in relation to an aneurysm. The non-circular lumen 99 allows an occlusion device whose compressed or constrained profile is substantially oval or elliptical, or otherwise non-circular, to be selectively oriented rotationally, for example, such that it can only be placed at 0°, or placed at 180°, or at another angle of rotation. A marking 95 on the luer hub 91 can be used to aid the insertion of the occlusion device such that it is oriented at a particular one of the 0° or 180° orientation, by serving as a comparative visual aid. In some embodiments, longitudinal stripes may be placed on the shaft 87 near the distal end 93 to allow steam shaping of the curve 97 (if not preshaped), or reshaping of the curve 97, along a desired plane. In some embodiments, steam shaping can be done by placing a bendable mandrel within the non-circular lumen 99 to further or alternatively aid the shaping or reshaping of the curve 97 along a desired plane. In some embodiments, the bendable mandrel has a similar cross-section shape as the non-circular lumen 99, such that it substantially fills the non-circular lumen 99.

Figure 88:
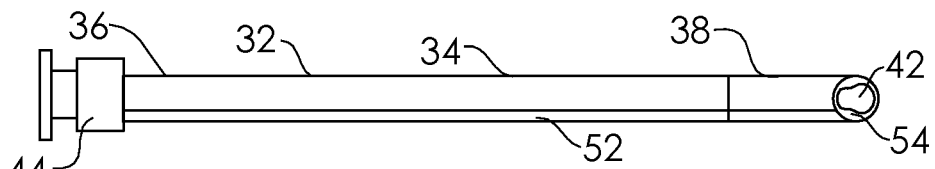
FIG. 88 is a top view of a delivery catheter according to an embodiment of the present disclosure.
Figure 89:
FIG. 89 is a side view of the delivery catheter of FIG. 88.
Figure 90:
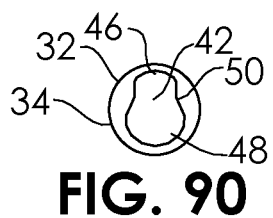
FIG. 90 is a magnified cross-section view taken along line 90 of FIG. 89.

FIGS. 88 and 89 illustrate a delivery catheter 32 comprising a shaft 34 having a proximal end 36, a distal end 38 having a curve 40, and a non-circular lumen 42. A luer hub 44 is bonded to the proximal end 36 of the shaft 34. In this particular embodiment, the non-circular lumen 42 extends through the entirety of the shaft 34. The non-circular lumen 42 is illustrated in FIG. 88 as a guitar shape having a first, smaller lobe 46 and a second, larger lobe 48 that are joined together by a waist 50. The guitar shape thus creates a key for allowing only one particular rotational positional of the occlusion device when it exits from the lumen 42 at the distal end 38 of the shaft 34, and thus, into the aneurysm. In some embodiments, the non-circular lumen 42 may taper down in size near the distal end 38 of the shaft 34. Thus, the occlusion device is held substantially tightly near the distal end 38 of the shaft 34, but there is more space through most of the length of the lumen 42, to minimize axial friction. Any other type of "keyed" shape may alternatively be used for the non-circular lumen 42. Optionally, to further aid visualization on fluoroscopy (e.g., biplane fluoroscopy), a longitudinal radiopaque stripe 52 may be extruded or otherwise placed on one side of the wall 54 of the shaft 34.

Turning to FIGS. 91-94, a loading sheath (or introducer sheath or insertion sheath) 56 is configured to aid in the insertion of an asymmetric occlusion device 58 (or asymmetric occlusion device 58/pusher 59/detachable joint 61 system) into the non-circular lumen 60 (FIG. 94) of a delivery catheter 62. The non-circular lumen 60 may only extend within the shaft 64 of the catheter 62, or the luer hub 66 itself may also have the non-circular lumen 60 (as illustrated in FIG. 94). A removable funnel 68 has a proximal end 70 attached to a distal end 72 of the loading sheath 56. The funnel 68 has a proximal inner diameter 74 (FIG. 93) that matches the diameter 76 at the distal end 72 of the loading sheath 56. The funnel 68 smoothly tapers up to an increased inner diameter 78 at a distal end 80. In use, the occlusion device 58 may be packaged inside the lumen 82 of the loading sheath 56 or may be packaged extending from the loading sheath 56. Prior to insertion into the non-circular lumen 60 of the delivery catheter 62, the occlusion device 58 may be prepared by priming or flushing the lumen 82 (FIG. 91) of the loading sheath 56. The occlusion device 58 may be examined or rinsed in saline or in saline and heparin, external to the loading sheath 56, as shown in FIG. 91. The user then carefully applies traction on (pulls) the pusher 59 to load the occlusion device 58 into the lumen 82 of the loading sheath 56 in the preferred compressed configuration. For example, with folded portions oriented in the most low-profile manner, or with the preferred distally extending portions configured such that they will exit the lumen 82 first. The inner contours of the funnel 68 optimize the ability to preferentially load the occlusion device 58 into the lumen 82. For example, the preferential loading may be done in a manner to obtain the smallest possible compressed or collapsed diameter. The loaded occlusion device 58 is shown in FIG. 92, fully within the lumen 82 of the loading sheath 56. As shown in FIG. 93, the funnel 68 can then be snapped off, unscrewed from, or otherwise removed from the loading sheath 56. The funnel 68 can then be removed and discarded. In some embodiments, the funnel 68 may be reattachable to the loading sheath 56 Turning to FIG. 94, the distal end 72 of the loading sheath 56 is placed close to the entrance of the non-circular lumen 60 such that, for example, a larger profile lobe 84 of the compressed occlusion device 58 can be matched for entry into the larger lobe 86 of the non-circular lumen 60, and a smaller profile lobe 88 of the occlusion device 58 can be matched for entry into the smaller lobe 90 of the non-circular lumen 60. The pusher 59 is then pushed by the user to load the occlusion device 58 in the non-circular lumen 60, and to advance the occlusion device 58 toward the distal end (not shown) of the delivery catheter 62. The loading sheath 56 may be peel-away, or may simply be pulled back to a proximal portion of the pusher 59. The occlusion device 58 can now be reliably delivered to an aneurysm in the chosen orientation. For example, correct-side-up, instead of upside-down. In some embodiments, the loading sheath may have external longitudinal stripes on the tubing to aid the user in applying the desired rotational orientation when inserting the occlusion device 58.

Alternative luminal shapes and occlusion device compressed shapes are shown in FIGS. 95A-95E. In the embodiment of FIG. 95A, the distal end 852 of a delivery catheter 850 has a non-circular lumen 854 having a pentagonal shape. An occlusion device 856 in its compressed configuration favors a substantially pentagonal shape that is keyable to the shape of the non-circular lumen 854. In the embodiment of FIG. 95B, the distal end 858 of a delivery catheter 860 has a non-circular lumen 862 having a diamond shape. An occlusion device 864 in its compressed configuration favors a substantially diamond shape that is keyable to the shape of the non-circular lumen 862. In the embodiment of FIG. 95C, the distal end 866 of a delivery catheter 868 has a non-circular lumen 870 having a U-shape. An occlusion device 872 in its compressed configuration favors a substantially U-shape that is keyable to the shape of the non-circular lumen 870. In the embodiment of FIG. 95D, the distal end 874 of a delivery catheter 876 has a non-circular lumen 878 having an oval shape. An occlusion device 880 in its compressed configuration favors a substantially oval shape that is keyable to the shape of the non-circular lumen 878. In the embodiment of FIG. 95E, the distal end 882 of a delivery catheter 884 has a non-circular lumen 886 having a guitar shape. An occlusion device 888 in its compressed configuration favors a substantially guitar shape that is keyable to the shape of the non-circular lumen 886.

FIGS. 96A and 97A-97C illustrate an occlusion device 2040 comprising a mesh cover 2042 including a distal concavity 2044. A radially offset internal tube 2046 having a lumen 2048 and an outer wall 2050 is secured within the mesh cover 2042, such that its proximal end 2052 is flush or closely adjacent to a proximal end 2054 of the mesh cover 2042. A pusher 2056 comprises a wire having a distal end 2058 including a plurality of radially-extending fingers 2060 which extend from the distal end 2058. The fingers 2060 are configured to be meltable, detachable, unbendable, breakable, ablatable, deformable, or otherwise changeable. Prior to detachment, the radially-extending fingers 2060 create a maximum diameter that is larger than the diameter of the lumen 2048 of the internal tube 2046, such that traction on the wire of the pusher 2056 causes the fingers 2060 to pull on the distal end of the outer wall 2050 of the internal tube 2046, and thus the pull the entire occlusion device 2040. For example, the occlusion device 2040 may be advanced into an aneurysm, and if the user does not believe the fit or configuration of the occlusion device 2040 within the aneurysm is desirable, the user may pull on the pusher 2056 to pull the occlusion device 2040 out of the aneurysm and into the lumen of the delivery catheter. However, then the occlusion device 2040 has been delivered into the aneurysm in an acceptable manner, the user may detach by any detachment manner (to deform, damage, or destroy the fingers 2060), via modes including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. In one embodiment, mechanical detachment is achieved by pushing the distal end of the microcatheter against the proximal end 2054 of the mesh cover 2042 while pulling on the pusher 2056, thus bending the fingers 2060, and removing the pusher 2056 from the occlusion device 2040. The internal tube 2046 provides for a smooth proximal end 2054 of the mesh cover 2042, and thus no remnant wire protruding proximally. Remnant protruding wires could cause thrombosis, which may cause embolic stroke. In some embodiments, the distal end 2058 of the pusher 2056 may taper down to as small as 0.001 inch or 0.002 inch, for example, if the distal end 2058 comprises a stainless steel wire. The internal tube 2046 may comprise a polyimide tube, and may have an internal diameter as small as 0.002 inch to 0.010 inch and an outer diameter of between about 0.003 inch and about 0.014 inch. In some embodiments there may be two fingers 2060, or three fingers 2060, or four fingers 2060, or five fingers 2060, of six fingers, 2060, or more.

The flush or adjacent relation of the proximal end 2052 of the internal tube 2046 to a proximal end 2054 of the mesh cover 2042 assures that there is no detachment remnant extending substantially proximal to the proximal end 2054 of the mesh cover 2042 (and into the parent artery). Thus, any potentially related thromboembolic events may be avoided, in cases wherein such a remnant would be a risk. FIG. 96B illustrates an alternative distal end 2058*b* comprising a ball 2062 having a spherical or globular shape. The detachment may occur at the ball 2062, or at a portion 2064 of the distal end 2058*b* proximal to the ball 2062, or at both. The ball 2064 may be attached to the pusher 2056 by epoxy, adhesive, welding, brazing, or soldering, or may be formed from the material of distal end 2058*b* by welding. FIG. 96C illustrates an alternative distal end 2058*c* comprising a disk 2066 having a flattened, circular shape. The detachment may occur at the disk 2066, or at a portion 2068 of the distal end 2058c proximal to the disk 2066, or at both. The disk 2066 may be attached to the pusher 2056 by epoxy, adhesive, welding, brazing, or soldering, or may be formed from the material of distal end 2058c by welding. FIG. 96D illustrates an alternative distal end 2058d comprising a tip 2070 having a frustoconical shape. The detachment may occur at the tip 2070, or at a portion 2072 of the distal end 2058d proximal to the tip 2070, or at both. The tip 2070 may be attached to the pusher 2056 by epoxy, adhesive, welding, brazing, or soldering, or may be formed from the material of distal end 2058d by welding. FIG. 96E illustrates an alternative distal end 2058e comprising a tip 2076 having a flattened reverse spear shape. The detachment may occur at the tip 2076, or at a portion 2078 of the distal end 2058e proximal to the tip 2076, or at both. The tip 2076 may be attached to the pusher 2056 by epoxy, adhesive, welding, brazing, or soldering, or may be formed from the material of distal end 2058e by welding, or may be a flattened portion of the pusher 2056 wire, e.g., by rolling or pressing. In each of the alternative embodiments, the diameter (or maximum transverse dimension) of the ball 2062, the disk 2066, the proximal end 2074 of the tip 2070, or the distal end 2080 of the tip 2076 are greater than the diameter of the lumen 2048 of the internal tube 2046, thus allowing the occlusion device 2040 to be detachably locked to the pushed 2056. Any of the tip configurations displayed in FIGS. 10A-10E and 96A-96E may be incorporated into a variety of different occlusion devices, including any of the occlusion devices disclosed herein.

The following clauses include examples of apparatus of the disclosure.

Clause 201: In one example, a vaso-occlusive system configured for embolizing an aneurysm, the aneurysm having a neck and a sac, includes an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal face configured to seat against a lower wall portion of the sac of the aneurysm against the neck of the aneurysm and a concavity, opposite the proximal face, and having a perimeter extending into the sac and away from the neck of the aneurysm, the concavity arranged around a longitudinal axis, and wherein the vaso-occlusive device is configured to be releasably coupled to the distal end of the pusher at a releasable joint, the distal end of the pusher extending from the releasable joint at an angle formed with the central longitudinal axis of between about 30 degrees and about 120 degrees.

Clause 202: In some examples, the system includes clause 201, wherein the pusher extends from the releasable joint at an angle formed with the central longitudinal axis of between about 40 degrees and about 100 degrees.

Clause 203: In some examples, the system includes clause 201, wherein the pusher extends from the releasable joint at an angle formed with the central longitudinal axis of between about 45 degrees and about 90 degrees.

Clause 204: In some examples, the system includes clause 201, wherein the pusher extends from the releasable joint at an angle formed with the central longitudinal axis of between about 75 degrees and about 90 degrees.

Clause 205: In some examples, the system includes any one of clauses 201-204, wherein the releasable joint is coupled to the proximal face of the vaso-occlusive device.

Clause 206: In some examples, the system includes clause 205, wherein the releasable joint is coupled at a location on the proximal face of the vaso-occlusive device that is radially offset from the central longitudinal axis.

Clause 207: In some examples, the system includes clause 206, wherein the vaso-occlusive device in its expanded, deployed configuration has a maximum radius, and wherein the location on the proximal face is offset at least 50% of the maximum radius.

Clause 208: In some examples, the system includes clause 206, wherein the vaso-occlusive device in its expanded, deployed configuration has a maximum radius, and wherein the location on the proximal face is offset at least 75% of the maximum radius.

Clause 209: In some examples, the system includes clause 206, wherein the vaso-occlusive device in its expanded, deployed configuration has a maximum radius, and wherein the location on the proximal face is at a radial edge.

Clause 210: In another example, a vaso-occlusive system configured for embolizing an aneurysm, the aneurysm having a neck and a sac, includes an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal face configured to seat against a lower wall portion of the sac of the aneurysm against the neck of the aneurysm and a concavity, opposite the proximal face, and having a perimeter extending into the sac and away from the neck of the aneurysm, the concavity arranged around a longitudinal axis, and wherein the vaso-occlusive device is configured to be releasably coupled to the distal end of the pusher at a releasable joint, and wherein the releasable joint is coupled at a location on the proximal face of the vaso-occlusive device that is radially offset from the central longitudinal axis.

Clause 211: In some examples, the system includes clause 210, wherein the vaso-occlusive device in its expanded, deployed configuration has a maximum radius, and wherein the location on the proximal face is offset at least 50% of the maximum radius.

Clause 212: In some examples, the system includes clause 210, wherein the vaso-occlusive device in its expanded, deployed configuration has a maximum radius, and wherein the location on the proximal face is offset at least 75% of the maximum radius.

Clause 213: In some examples, the system includes clause 210, wherein the vaso-occlusive device in its expanded, deployed configuration has a maximum radius, and wherein the location on the proximal face is at a radial edge.

Clause 214: In some examples, the system includes any one of clauses 201-213, wherein the vaso-occlusive device includes a cover having a first side and a second side, wherein the proximal face includes the first side of the cover and the concavity includes the second side of the cover.

Clause 215: In some examples, the system includes any one of clauses 201-214, wherein the vaso-occlusive device is formed from a mesh material Clause 216: In some examples, the system includes clause 215, wherein the mesh material includes a plurality of filaments.

Clause 217: In some examples, the system includes clause 216, wherein the plurality of filaments includes filaments including a nickel-titanium alloy.

Clause 218: In some examples, the system includes clause 216, wherein the plurality of filaments includes filaments including a radiopaque material.

Clause 219: In some examples, the system includes clause 216, wherein the plurality of filaments includes filaments including drawn filled tubes.

Clause 220: In some examples, the system includes any one of clauses 217-219, wherein the plurality of filament includes filaments including platinum.

Clause 221: In another example, a vaso-occlusive system configured for embolizing an aneurysm, the aneurysm having a neck and a sac, includes an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal face configured to seat against a lower wall portion of the sac of the aneurysm against the neck of the aneurysm and a concavity, opposite the proximal face, and having a perimeter extending into the sac and away from the neck of the aneurysm, the concavity arranged around a longitudinal axis, and wherein the vaso-occlusive device is configured to be releasably coupled to the distal end of the pusher at a releasable joint, and wherein the releasable joint has a characteristic chosen from the list consisting of: (1) the distal end of the pusher extends from the releasable joint at an angle formed with the central longitudinal axis of between about 30 degrees and about 120 degrees, and (2) the releasable joint is coupled at a location on the proximal face of the vaso-occlusive device that is radially offset from the central longitudinal axis.

Clause 222: In another example, a system for embolizing an aneurysm includes an expandable implant configured for placement within an aneurysm, the implant having a collapsed configuration and an expanded configuration, the expanded configuration having an asymmetric shape in relation to a longitudinal axis, and a delivery catheter having a proximal end and a distal end and a lumen extending from the proximal end to the distal end, the lumen having a non-circular cross-section at least at a distal region adjacent the distal end of the delivery catheter, wherein expandable implant in its collapsed configuration is configured to fit into the lumen in the distal region in a keyed manner, such that the expandable implant is deliverable from the lumen at the distal end of the delivery catheter in a particular rotational position in relation to the longitudinal axis.

Clause 223: In some examples, the system includes clause 222, further including an elongate pusher having a distal end, the distal end releasably coupled to the expandable implant.

Clause 224: In some examples, the system includes either one of clauses 222 or 223, wherein the non-circular cross section of the lumen includes an oval.

Clause 225: In some examples, the system includes either one of clauses 222 or 223, wherein the non-circular cross section of the lumen includes an ellipse.

Clause 226: In some examples, the system includes either one of clauses 222 or 223, wherein the non-circular cross section of the lumen includes a dogbone shape.

Clause 227: In some examples, the system includes either one of clauses 222 or 223, wherein the non-circular cross section of the lumen includes a guitar shape.

Clause 228: In some examples, the system includes either one of clauses 222 or 223, wherein the non-circular cross section includes a polygonal shape.

Clause 229: In some examples, the system includes either one of clauses 222 or 227, wherein the lumen of the delivery catheter has a circular cross-section at its proximal end.

Clause 230: In some examples, the system includes clause 229, wherein the circular cross-section extends from the proximal end of the delivery catheter to a proximal end of the distal region.

Clause 231: In some examples, the system includes any one of clauses 222-230, wherein the expandable implant in its collapsed configuration has a first transverse axis in relation to the longitudinal axis and a second transverse axis in relation to the longitudinal axis, the first transverse axis orthogonal to the second transverse axis, wherein a first transverse dimension along the first transverse axis is different from a second transverse dimension along the second transverse axis.

Clause 232: In some examples, the system includes any one of clauses 222-231, further including a introducer having a proximal end and a distal end and an introducer lumen extending between the proximal end of the introducer and the distal end of the introducer, the introducer lumen configured to hold the expandable implant in its collapsed configuration while the expandable implant is introduced into the lumen of the delivery catheter at its proximal end.

Clause 233: In some examples, the system includes clause 232, wherein the introducer includes an outwardly extending collar adjacent its distal end.

Clause 234: In some examples, the system includes clause 233, wherein the collar has a proximal end coupled to the distal end of the introducer and a distal end, wherein the collar has a first inner transverse dimension at its proximal end, the first inner transverse dimension about the same as a transverse dimension of the lumen of the introducer at the distal end of the introducer.

Clause 235: In some examples, the system includes clause 234, wherein the collar has a second inner transverse dimension at its distal end, the second inner transverse dimension greater than the first inner transverse dimension.

Clause 236: In some examples, the system includes clause 235, wherein there is a gradual increase along the collar between the first inner transverse dimension and the second inner transverse dimension.

Clause 237: In some examples, the system includes any one of clauses 233-236, wherein the collar is removable from the introducer.

Clause 238: In some examples, the system includes either one of clauses 229 or 230, further including a continuously smooth transition region between the circular cross section and the non-circular cross-section.

Clause 239: In another example, a method for inserting an expandable implant includes providing an introducer having a proximal end and a distal end and an introducer lumen extending between the proximal end of the introducer and the distal end of the introducer, the introducer lumen configured to hold an expandable implant in its collapsed configuration while the expandable implant is introduced into the lumen of the delivery catheter at its proximal end, wherein the lumen of the delivery catheter has a non-circular shape, and wherein the expandable implant in its collapsed configuration has a substantially non-circular shape, pushing the expandable implant out of the introducer lumen and into the lumen of the delivery catheter such that the substantially non-circular shape of the expandable implant in its collapsed configuration is oriented in a keyed manner with the non-circular shape of the lumen of the delivery catheter, and advancing the expandable implant such that it is entirely within the lumen of the delivery catheter.

Clause 240: In another example, a vaso-occlusive system configured for embolizing an aneurysm, the aneurysm having a neck and a sac, includes an elongate pusher configured to be slidably disposed within a delivery catheter, the delivery catheter having a proximal end, a distal end, and a delivery lumen extending therebetween, an implantable vaso-occlusive device coupled to a distal end of the pusher, the vaso-occlusive device configured for implantation in the aneurysm sac and having a collapsed delivery configuration when restrained within the delivery lumen of the delivery catheter, and an expanded, deployed configuration after being delivered out of the delivery lumen of the delivery catheter and into the aneurysm sac, wherein the vaso-occlusive device includes a proximal end configured to seat against the aneurysm adjacent the neck of the aneurysm, a distal end configured to extend in the sac and away from the neck of the aneurysm, and a central longitudinal axis, and wherein the vaso-occlusive device is configured to be releasably coupled to the distal end of the pusher at a releasable joint, wherein the releasable joint includes either one or both of the configurations in the list consisting of: (1) the distal end of the pusher extends from the releasable joint at an angle formed with the central longitudinal axis of between about 30 degrees and about 120 degrees, and (2) the releasable joint is coupled at a location on the proximal end of the vaso-occlusive device that is radially offset from the central longitudinal axis.

Clause 241: In some examples, the system includes clause 240, wherein the distal end of the pusher extends from the releasable joint at an angle formed with the central longitudinal axis of between about 40 degrees and about 100 degrees.

Clause 242: In some examples, the system includes clause 240, wherein the distal end of the pusher extends from the releasable joint at an angle formed with the central longitudinal axis of between about 45 degrees and about 90 degrees.

Clause 243: In some examples, the system includes clause 240, wherein the distal end of the pusher extends from the releasable joint at an angle formed with the central longitudinal axis of between about 75 degrees and about 90 degrees.

Clause 244: In some examples, the system includes clause 240, wherein the releasable joint is directly attached to the proximal end of the vaso-occlusive device.

Clause 245: In some examples, the system includes clause 240, wherein the vaso-occlusive device in its expanded, deployed configuration has a maximum radius, and wherein the location on the proximal end of the vaso-occlusive device is radially offset from the central longitudinal axis at least 10% of the maximum radius.

Clause 246: In some examples, the system includes clause 240, wherein the vaso-occlusive device in its expanded, deployed configuration has a maximum radius, and wherein the location on the proximal end of the vaso-occlusive device is radially offset from the central longitudinal axis at least 50% of the maximum radius.

Clause 247: In some examples, the system includes clause 240, wherein the vaso-occlusive device in its expanded, deployed configuration has a maximum radius, and wherein the location on the proximal end of the vaso-occlusive device is radially offset from the central longitudinal axis at least 75% of the maximum radius.

Clause 248: In some examples, the system includes clause 240, wherein the vaso-occlusive device in its expanded, wherein the location on the proximal end of the vaso-occlusive device is at a radial edge of the vaso-occlusive device.

Clause 249: In some examples, the system includes clause 240, wherein the vaso-occlusive device includes a cover, and wherein the proximal end of the vaso-occlusive device includes a proximal face of the cover, the cover further including a concavity opposite and distal to the proximal face.

Clause 250: In some examples, the system includes clause 249, wherein the concavity is generally arranged around the central longitudinal axis.

Clause 251: In some examples, the system includes clause 249, wherein the cover has a generally circular outer shape.

Clause 252: In some examples, the system includes clause 240, wherein the vaso-occlusive device is formed from a mesh material Clause 253: In some examples, the system includes clause 252, wherein the mesh material includes a plurality of filaments.

Clause 254: In some examples, the system includes clause 253, wherein the plurality of filaments includes filaments including a nickel-titanium alloy.

Clause 255: In some examples, the system includes clause 253, wherein the plurality of filaments includes filaments including a radiopaque material.

Clause 256: In some examples, the system includes clause 253, wherein the plurality of filaments includes filaments including drawn filled tubes.

Clause 257: In some examples, the system includes clause 252, wherein the mesh material includes an inverted mesh tube having an outer layer and an inner layer, the outer layer transitioning to the inner layer at an inversion fold.

Clause 258: In some examples, the system includes clause 240, further including a selective orientation catheter having a proximal end, a distal end, and a lumen extending from the proximal end to the distal end, wherein the lumen of the selective orientation catheter includes a non-circular cross-section at least at a distal region adjacent the distal end of the selective orientation catheter, wherein the vaso-occlusive device in its collapsed delivery configuration has a substantially non-circular cross-section configured to fit into at least the distal region of the lumen of the selective orientation catheter in a keyed manner, such that the vaso-occlusive device is deliverable from the lumen of the selective orientation catheter in a particular rotational position.

Clause 259: In some examples, the system includes clause 258, wherein the non-circular cross-section of the lumen of the selective orientation catheter includes an oval.

Clause 260: In some examples, the system includes clause 258, wherein the non-circular cross-section of the lumen of the selective orientation catheter includes an ellipse.

Clause 261: In some examples, the system includes clause 258, wherein the non-circular cross-section of the lumen of the selective orientation catheter includes a shape selected from the list consisting of: a dogbone shape, a guitar shape, and a polygonal shape.

Clause 262: In some examples, the system includes clause 258, wherein the lumen of the selective orientation catheter has a circular cross-section located at least at its proximal end.

Clause 263: In some examples, the system includes clause 262, wherein the circular cross-section of the lumen of the selective orientation catheter includes a circular cross-section region extending from the proximal end of the selective orientation catheter and distally toward a proximal end of the distal region.

Clause 264: In some examples, the system includes clause 263, further including a continuously smooth transition region mating the circular cross-section region and the distal region.

Clause 265: In some examples, the system includes clause 258, wherein the vaso-occlusive device in its collapsed delivery configuration has a first transverse axis and a second transverse axis, the first transverse axis orthogonal to the second transverse axis, wherein a first transverse dimension along the first transverse axis is different from a second transverse dimension along the second transverse axis.

Clause 266: In some examples, the system includes clause 258, further including a introducer having a proximal end, a distal end, and an introducer lumen extending between the proximal end of the introducer and the distal end of the introducer, the introducer lumen configured to hold the expandable implant in its collapsed configuration while the expandable implant is introduced into the lumen of the delivery catheter at its proximal end, wherein the introducer includes collar adjacent its distal end having an inner transverse dimension that increases from a proximal collar end to a distal collar end, the collar configured to facilitate the transitioning of the vaso-occlusive device from its expanded, deployed configuration to its collapsed delivery configuration when traction is placed on the elongate pusher by a user.

Clause 267: In some examples, the system includes clause 266, wherein the collar is removable from the introducer by the user, after the vaso-occlusive device has been placed into its collapsed delivery configuration within the introducer lumen of the introducer.

Clause 268: In some examples, the system includes clause 240, further including a connection tube having a proximal end substantially flush with a proximal end of the vaso-occlusive device, a distal end extending within the vaso-occlusive device, and a lumen, wherein the distal end of the pusher extends through the lumen of the connection tube and includes a plurality of radially extending protrusions located distal to the distal end of the connection tube, the plurality of radially extending protrusions forming a maximum transverse dimension that is greater than a maximum diameter of the lumen of the connection tube.

Clause 269: In some examples, the system includes clause 258, further including an activator configured to modify the plurality of radially extending protrusions such that the distal end of the pusher can be fully removed from the lumen of the connection tube.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. An apparatus for treating an aneurysm in a blood vessel, comprising:
    an occlusion device configured to be releasably coupled to an elongate delivery shaft, the occlusion device comprising:
        a cover having a proximal end, a distal end, and a longitudinal axis extending between the proximal end and the distal end, the cover comprising an inverted mesh tube having an outer layer and an inner layer, the outer layer transitioning to the inner layer at the distal end of the cover, the cover further comprising a first plane transverse to the longitudinal axis, wherein the inner layer defines a first inner diameter within the first plane and the outer layer defines a first outer diameter within the first plane, the first inner diameter less than the first outer diameter; and
        a first tubular mesh having a first end, a second end, and a doubled-over shape, the doubled-over shape of the first tubular mesh having an apex between the first end and the second end of the first tubular mesh, wherein the apex defines a distal end of the occlusion device, and wherein the first tubular mesh in its doubled-over shape has a first transverse dimension configured to fit closely within the first inner diameter, and wherein the first end and the second end of the first tubular mesh are secured close to each other within the cover.

2. The apparatus of claim 1, wherein the first tubular mesh in its doubled-over shape is not configured to contact an interior wall of the aneurysm at the first transverse dimension.

3. The apparatus of claim 1, wherein the first tubular mesh in its doubled-over shape has a maximum transverse dimension and wherein the cover has a maximum outer diameter, the maximum transverse dimension less than the maximum outer diameter.

4. The apparatus of claim 1, wherein the occlusion device is configured to be delivered in a collapsed configuration within an inner lumen of a delivery catheter, the occlusion device further having an expanded configuration when advanced to a position outside the inner lumen of the delivery catheter.

5. The apparatus of claim 1, wherein the cover comprises an orifice defined by the first inner diameter, and wherein the cover has a maximum outer diameter, the first inner diameter between about 35% and about 85% of the maximum outer diameter.

6. The apparatus of claim 1, wherein the first tubular mesh in its doubled-over shape comprises a substantially 180 degree turn.

7. The apparatus of claim 6, wherein the doubled-over shape comprises a first leg extending between the first end of the first tubular mesh and the apex and a second leg extending between the second end of the first tubular mesh and the apex.

8. The apparatus of claim 1, wherein the outer layer of the cover comprises a frustoconical shape.

9. The apparatus of claim 1, wherein the cover further comprises a second plane transverse to the longitudinal axis and a maximum outer diameter within the second plane, wherein the second plane is proximal to the first plane.

10. The apparatus of claim 9, wherein the second plane is between the proximal end of the cover and the distal end of the cover.

11. An apparatus for treating an aneurysm in a blood vessel, comprising:
   an occlusion device configured to be releasably coupled to an elongate delivery shaft, the occlusion device comprising:
      a cover having a proximal end, a distal end, and a longitudinal axis extending between the proximal end and the distal end, the cover comprising an inverted mesh tube having an outer layer and an inner layer, the outer layer transitioning to the inner layer at the distal end of the cover, the cover further comprising a first plane transverse to the longitudinal axis, wherein the inner layer defines an orifice having a first inner diameter residing within the first plane, and wherein the outer layer defines a first outer diameter within the first plane, the first inner diameter less than the first outer diameter; and
      a first tubular mesh having a first end, a second end, and a doubled-over shape, the doubled-over shape of the first tubular mesh having an apex between the first end and the second end of the first tubular mesh, wherein the apex defines a distal end of the occlusion device, and wherein the first tubular mesh in its doubled-over shape has a first transverse dimension configured to match the orifice, and wherein the first end and the second end of the first tubular mesh are secured close to each other within the cover.

12. The apparatus of claim 11, wherein the first tubular mesh in its doubled-over shape is not configured to contact an interior wall of the aneurysm at the first transverse dimension.

13. The apparatus of claim 11, wherein the first tubular mesh in its doubled-over shape has a maximum transverse dimension and wherein the cover has a maximum outer diameter, the maximum transverse dimension less than the maximum outer diameter.

14. The apparatus of claim 11, wherein the occlusion device is configured to be delivered in a collapsed configuration within an inner lumen of a delivery catheter, the occlusion device further having an expanded configuration when advanced to a position outside the inner lumen of the delivery catheter.

15. The apparatus of claim 11, wherein the cover has a maximum outer diameter, and wherein the first inner diameter is between about 35% and about 85% of the maximum outer diameter.

16. The apparatus of claim 11, wherein the first tubular mesh in its doubled-over shape comprises a substantially 180 degree turn.

17. The apparatus of claim 16, wherein the doubled-over shape comprises a first leg extending between the first end of the first tubular mesh and the apex and a second leg extending between the second end of the first tubular mesh and the apex.

18. The apparatus of claim 11, wherein the outer layer of the cover comprises a frustoconical shape.

19. The apparatus of claim 11, wherein the cover further comprises a second plane transverse to the longitudinal axis and a maximum outer diameter within the second plane, wherein the second plane is proximal to the first plane.

20. The apparatus of claim 19, wherein the second plane is between the proximal end of the cover and the distal end of the cover.

* * * * *